(12) United States Patent
Gorek et al.

(10) Patent No.: US 9,119,572 B2
(45) Date of Patent: Sep. 1, 2015

(54) MONITORING TRAJECTORY OF SURGICAL INSTRUMENT DURING THE PLACEMENT OF A PEDICLE SCREW

(76) Inventors: Josef Gorek, Ross, CA (US); Eric Finley, Poway, CA (US); Albert C. Kim, San Diego, CA (US); Jeff Barnes, San Diego, CA (US); Rick Eis, San Diego, CA (US)

( * ) Notice: Subject to any disclaimer, the term of this patent is extended or adjusted under 35 U.S.C. 154(b) by 692 days.

(21) Appl. No.: 12/739,950

(22) PCT Filed: Oct. 24, 2008

(86) PCT No.: PCT/US2008/012121
§ 371 (c)(1),
(2), (4) Date: Aug. 23, 2010

(87) PCT Pub. No.: WO2009/055034
PCT Pub. Date: Apr. 30, 2009

(65) Prior Publication Data
US 2010/0312103 A1    Dec. 9, 2010

Related U.S. Application Data

(60) Provisional application No. 61/000,349, filed on Oct. 24, 2007, provisional application No. 61/196,266, filed on Oct. 15, 2008.

(51) Int. Cl.
| | | |
|---|---|---|
| *A61B 6/00* | (2006.01) | |
| *A61B 6/12* | (2006.01) | |
| *A61B 17/17* | (2006.01) | |
| A61B 19/00 | (2006.01) | |
| A61B 5/04 | (2006.01) | |
| A61N 1/05 | (2006.01) | |

(52) U.S. Cl.
CPC . *A61B 6/12* (2013.01); *A61B 6/547* (2013.01); *A61B 17/1703* (2013.01); *A61B 5/04001* (2013.01); *A61B 6/4441* (2013.01); *A61B 19/5225* (2013.01); *A61B 19/5244* (2013.01); *A61B 2019/467* (2013.01); *A61N 1/0551* (2013.01)

(58) Field of Classification Search
CPC .............. A61B 17/17; A61B 2019/202; A61B 17/1703; A61B 17/1757; A61B 2018/2025
USPC ...................................... 600/427; 606/96, 104
See application file for complete search history.

(56) References Cited

U.S. PATENT DOCUMENTS

| | | |
|---|---|---|
| 2,666,430 A | 1/1954 | Gispert |
| 4,164,871 A | 8/1979 | Cole et al. |
| 4,257,411 A | 3/1981 | Cho |
| 4,823,780 A | 4/1989 | Odensten et al. |
| 5,113,953 A | 5/1992 | Noble |
| 5,440,492 A | 8/1995 | Kozah et al. |
| 5,446,548 A | 8/1995 | Gerig et al. |

(Continued)

FOREIGN PATENT DOCUMENTS

| | | |
|---|---|---|
| WO | WO 2007035925 A2 * | 3/2007 |
| WO | 2007/136784 | 11/2007 |

*Primary Examiner* — Unsu Jung
*Assistant Examiner* — Serkan Akar
(74) *Attorney, Agent, or Firm* — Jonathan Spangler; Heather Prado

(57) ABSTRACT

The present invention relates to a system and methods generally aimed at monitoring the trajectory of surgical instruments and especially for monitoring the trajectory of surgical instrument used during pedicle fixation to ensure the proper placement of pedicle screws.

17 Claims, 39 Drawing Sheets

(56) References Cited

U.S. PATENT DOCUMENTS

| | | | |
|---|---|---|---|
| 5,467,532 A | 11/1995 | Ames | |
| 5,481,957 A | 1/1996 | Paley et al. | |
| 5,484,029 A | 1/1996 | Eddison | |
| 5,617,926 A | 4/1997 | Eddison et al. | |
| 5,672,820 A | 9/1997 | Rossi et al. | |
| 5,711,299 A | 1/1998 | Manwaring et al. | |
| 5,799,055 A | 8/1998 | Peshkin et al. | |
| 5,870,832 A | 2/1999 | Slocum | |
| 6,045,508 A | 4/2000 | Hossack et al. | |
| 6,092,928 A | 7/2000 | Mattson et al. | |
| 6,221,082 B1 | 4/2001 | Marino et al. | |
| 6,254,572 B1 | 7/2001 | Knipfer et al. | |
| 6,261,247 B1 | 7/2001 | Ishikawa et al. | |
| 6,263,984 B1 | 7/2001 | Buckman, Sr. | |
| 6,568,850 B2 | 5/2003 | Vallin et al. | |
| 6,621,460 B2 | 9/2003 | Challoner | |
| 6,638,281 B2 | 10/2003 | Gorek | |
| 6,697,664 B2 | 2/2004 | Kienzle, III et al. | |
| 6,725,080 B2 | 4/2004 | Melkent et al. | |
| 6,727,704 B2 | 4/2004 | Brune et al. | |
| 6,843,793 B2 | 1/2005 | Brock et al. | |
| 2002/0095159 A1 | 7/2002 | Deloge et al. | |
| 2002/0161280 A1 | 10/2002 | Chatenever et al. | |
| 2003/0181919 A1* | 9/2003 | Gorek | 606/96 |
| 2003/0199882 A1* | 10/2003 | Gorek | 606/104 |
| 2004/0087962 A1* | 5/2004 | Gorek | 606/96 |
| 2005/0021044 A1* | 1/2005 | Stone et al. | 606/102 |
| 2005/0075578 A1 | 4/2005 | Gharib et al. | |
| 2005/0149054 A1* | 7/2005 | Gorek | 606/104 |
| 2005/0251139 A1* | 11/2005 | Roh | 606/61 |
| 2007/0055291 A1* | 3/2007 | Birkmeyer et al. | 606/130 |
| 2010/0036384 A1 | 2/2010 | Gorek et al. | |

* cited by examiner

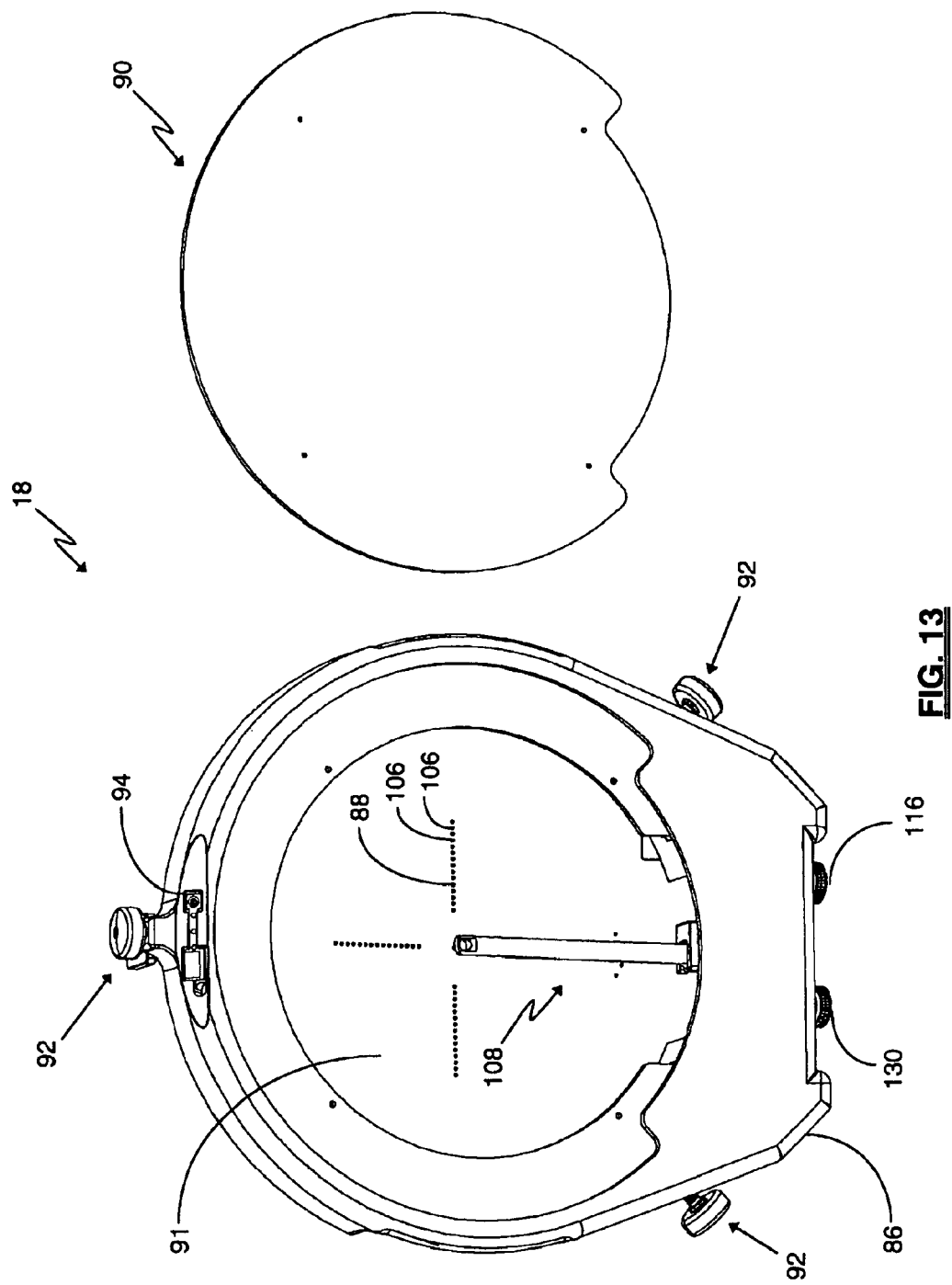

MONITORING TRAJECTORY OF SURGICAL INSTRUMENT DURING THE PLACEMENT OF A PEDICLE SCREW

CROSS-REFERENCE TO RELATED APPLICATIONS

This International Patent application claims the benefit of priority under

This is an International Patent Application claiming the benefit of priority under 35 U.S.C. §119(e) from the following commonly owned and applications: U.S. Provisional Patent Application Ser. No. 61/000,349 entitled "Surgical Trajectory Monitoring System and Related Methods," and filed on Oct. 24, 2007 and U.S. Provisional Patent Application Ser. No. 61/196,266, entitled "Surgical Trajectory Monitoring System and Related Methods," and filed on Oct. 15, 2008, the entire contents each of which are expressly incorporated by reference into this disclosure as if they were set forth in their entireties herein.

BACKGROUND OF THE INVENTION

I. Field of the Invention

The present invention relates generally to determining a desired trajectory and/or monitoring the trajectory of surgical instruments and implants and, more particularly, doing so during spinal surgery, including but not limited to ensuring proper placement of pedicle screws during pedicle fixation procedures and ensuring proper trajectory during the establishment of an operative corridor to a spinal target site.

II. Discussion of the Art

Determining the optimal or desired trajectory for surgical instruments and/or implants and monitoring the trajectory of surgical instruments and/or implants during surgery have presented challenges to surgeons since the inception of surgery itself. One example is pedicle fixation, which is frequently performed during spinal fusions and other procedures designed to stabilize or support one or more spine segments. Pedicle fixation entails securing bone anchors (e.g. pedicle screws) through the pedicles and into the vertebral bodies of the vertebrae to be fixed or stabilized. Rods or other connectors are used to link adjacent pedicle screws and thus fix or stabilize the vertebrae relative to each other. A major challenge facing the surgeon during pedicle fixation is implanting the pedicle screws without breaching, cracking, or otherwise compromising the pedicle wall, which may easily occur if the screw is not properly aligned with the pedicle axis. If the pedicle (or more specifically, the cortex of the medial wall, lateral wall, superior wall and/or inferior wall) is breached, cracked, or otherwise compromised, the patient may experience pain and/or neurologic deficit due to unwanted contact between the pedicle screw and delicate neural structures, such as the spinal cord or exiting nerve roots, which lie in close proximity to the pedicle. A misplaced pedicle screw often necessitates revision surgery, which is disadvantageously painful for the patient and costly, both in terms of recovery time and hospitalization.

The present invention is aimed primarily at eliminating or at least reducing the challenge associated with determining the optimal or desired trajectory for surgical instruments and/or implants and monitoring the trajectory of surgical instruments and/or implants during surgery.

SUMMARY OF THE INVENTION

The present invention facilitates the safe and reproducible use of surgical instruments and/or implants by providing the ability to determine the optimal or desired trajectory for surgical instruments and/or implants and monitor the trajectory of surgical instruments and/or implants during surgery. By way of example only, the present invention may be used to ensure safe and reproducible pedicle screw placement by monitoring the axial trajectory of surgical instruments used during pilot hole formation and/or screw insertion. Neurophysiologic monitoring may also be carried out during pilot hole formation and/or screw insertion. It is expressly noted that in addition to its uses in pedicle screw placement, the present invention is suitable for use in any number of additional surgical procedures where the angular orientation or trajectory of instrumentation and/or implants and/or instrumentation is important, including but not limited to general (non-spine) orthopedics and non-pedicular based spine procedures. It will be appreciated then that while the surgical instruments are generally described below as pedicle access tools, cannulas, retractor assemblies, and imaging systems (e.g. C-arms), various other surgical instruments (e.g. drills, screw drivers, taps, etc. . . . ) may be substituted depending on the surgical procedure being performed and/or the needs of the surgeon.

A surgical trajectory system may include an angle-measuring device (hereafter "tilt sensor") and a feedback device. The tilt sensor measures its angular orientation with respect to a reference axis (such as, for example, "vertical" or "gravity") and the feedback device may display or otherwise communicate the measurements. Because the tilt sensor is attached to a surgical instrument the angular orientation of the instrument, may be determined as well, enabling the surgeon to position and maintain the instrument along a desired trajectory during use.

The tilt sensor may include a sensor package enclosed within a housing. The housing is coupled to or formed as part of a universal clip to attach the tilt sensor to a surgical instrument. The sensor package may comprise a 2-axis accelerometer which measures its angular orientation in each of a sagittal and transverse plane with respect to the acting direction of gravity. The sagittal orientation corresponds to a cranial-caudal angle and the transverse orientation corresponds to a medial-lateral angle. The sensor package is preferably situated such that when the tilt sensor is perpendicular to the direction of gravity, the inclinometer registers a zero angle in both the sagittal and transverse planes. Thus, when the tilt sensor is fixed perpendicularly to the longitudinal axis of the surgical instrument, the angular orientation of the longitudinal axis of the instrument is determined relative to gravity. Alternatively, a 3-axis sensor may be used. The 3-axis sensor may comprise a 2-axis accelerometer to measure sagittal and transverse orientation and either a gyroscope and/or one or more magnetometers (e.g. a single 3-axis magnetometer or a combination of a 1-axis magnetometer and a 2-axis magnetometer) to measure the longitudinal axial rotation of the instrument.

A surgical instrument for use with the surgical trajectory system may comprise, by way of example only, a pedicle access probe. The instrument may generally comprise a probe member having a longitudinal axis and a handle. The probe member may be embodied in any variety of configurations that can be inserted through an operating corridor to a pedicle target site and bore, pierce, or otherwise dislodge and/or impact bone to form a pilot hole for pedicle screw placement. The probe member may be composed of any material suitable for surgical use and strong enough to impact bone to form a pilot hole. In one embodiment, the material may be capable of conducting an electric current signal to allow for the use of neurophysiologic monitoring.

The handle may be permanently or removably attached to the probe member and may be shaped and dimensioned in any of a number of suitable variations to assist in manipulating the probe member. In some embodiments, the handle includes a cutout region for accommodating attachment of the universal clip. In other embodiments, the handle includes an integral cavity for receiving the tilt sensor directly. In still other embodiments the tilt sensor is permanently integrated into the instrument handle.

A control unit may be communicatively linked to the tilt sensor via a hard wire or wireless technology. The feedback device may communicate any of numerical, graphical, and audio feedback corresponding to the orientation of the tilt sensor in the sagittal plane (cranial-caudal angle) and in the transverse plane (medial-lateral angle).

In general, to orient and maintain the surgical instrument along a desired trajectory during pilot hole formation, the surgical instrument is advanced to the pedicle (through any of open, mini-open, or percutaneous access) while oriented in the zero-angle position. The instrument is then angulated in the sagittal plane until the proper cranial-caudal angle is reached. Maintaining the proper cranial-caudal angle, the surgical instrument may then be angulated in the transverse plane until the proper medial-lateral angle is attained. Once the control unit or secondary feedback device indicates that both the medial-lateral and cranial caudal angles are matched correctly, the instrument may be advanced into the pedicle to form the pilot hole, monitoring the angular trajectory of the instrument until the hole formation is complete.

Before the pilot hole is formed, the desired angular trajectory (e.g. the cranial-caudal angle and the medial-lateral angle) must first be determined. Preoperative superior view MRI or CAT scan images are used to determine the medial-lateral angle. A reference line is drawn through the center of the vertebral body and a trajectory line is then drawn from a central position in the pedicle to an anterior point of the vertebral body. The resulting angle between the trajectory line and the reference line is the desired medial-lateral angle to be used in forming the pilot hole.

The cranial-caudal angle may be determined using an intraoperative lateral fluoroscopy image incorporating a vertical reference line. Again, a trajectory line is drawn from the pedicle nucleus to an anterior point of the vertebral body. The resulting angle between the trajectory line and the vertical reference line is the desired cranial-caudal angle to be used in forming the pilot hole. A protractor outfitted with a tilt sensor may be provided to assist in determining the cranial-caudal angle in the operating room. Alternatively, the cranial-caudal angle may be calculated preoperatively using imaging techniques that provide a lateral view of the spine. The medial-lateral and cranial-caudal angles should be determined for each pedicle that is to receive a pedicle screw. Alternate and/or additional methods for predetermining the pedicle angles are also contemplated and may be used without deviating from the scope of the present invention.

According to one embodiment of the present invention, a reticle may be provided to attach the tilt sensor to a standard C-arm. The reticle comprises an integrated sensor and a mount which may attach to the C-arm. The reticle further comprises an adjustable laser. The laser may be aimed along the C-arm axis. In use the laser cross-hair will mark a target incision site on a patient when the C-arm is oriented in line with the pedicle axis. Radiopaque markers are also integrated into the reticle. The markers provide a reference for properly aligning the fluoroscopic images.

To select a starting point for pedicle penetration, the C-arm may be placed in the trajectory lateral position. From the trajectory lateral position the C-arm may be rotated back to the A/P position while maintaining the radial rotation imparted to achieve the trajectory lateral position. A surgical instrument may be advanced to the target site and positioned on the lateral margin of the pedicle, the preferred starting point according to this example. The depth of penetration of the surgical instrument may be checked during advancement by rotating the C-arm back to a trajectory lateral view.

Alternatively, the starting point may be determined using an "owls eye" view. The C-arm may be oriented such that it is aligned with both the medial-lateral and cranial-caudal angles as discussed above. The tip of the pedicle access instrument is placed on the skin so that the tip is located in the center of the pedicle of interest on the fluoroscopic image; and thereafter the instrument is advanced to the pedicle. Another fluoroscopic image is taken to verify that the tip of the instrument is still aligned in the center of the pedicle.

Using the "owls eye" view, a standard surgical instrument may be guided along a pedicle axis without the use of an additional tilt sensor on the surgical instrument. In the "owls eye" image, a surgical instrument properly aligned with the pedicle axis will appear as a black dot. Once aligned, the surgical instrument may be advanced through the pedicle while ensuring that it continues to appear as only a dot on the fluoroscopy image. The depth of penetration may again be checked with a trajectory lateral image.

Neurophysiologic monitoring may be carried out in conjunction with the trajectory monitoring performed by the surgical trajectory system. The surgical trajectory system may be used in combination with neurophysiologic monitoring systems to conduct pedicle integrity assessments before, during, and after pilot hole formation, as well as to detect the proximity of nerves while advancing and withdrawing the surgical instrument from the pedicle target site. By way of example only, a neurophysiology system is described which may be used in conjunction with the surgical trajectory system. By way of further example, the neurophysiology system and the surgical trajectory system may be integrated into a single system. Neurophysiology monitoring and trajectory monitoring may be carried out concurrently and the control unit may display results for each of the trajectory monitoring function and any of a variety of neurophysiology monitoring functions, including, but not necessarily limited to, Twitch Test, Free-run EMG, Basic Screw Test, Difference Screw Test, Dynamic Screw Test, Nerve Detection, Nerve Health, MEP, and SSEP.

The neurophysiology system includes a display, a control unit, a patient module, one or more of an EMG harness and an SSEP harness, a host of surgical accessories (including an electric coupling device) capable of being coupled to the patient module via one or more accessory cables. According to one embodiment, the electric coupling device may be the tilt sensor clip.

To perform the neurophysiologic monitoring, the surgical instrument is configured to transmit a stimulation signal from the neurophysiology system to the target body tissue (e.g. the pedicle). As previously mentioned, the surgical instrument probe members may be formed of material capable of conducting the electric signal. To prevent shunting of the stimulation signal, the probe members may be insulated, with an electrode region near the distal end of the probe member for delivering the electric signal and a coupling region near the proximal end of the probe member for coupling to the neurophysiology system.

According to one exemplary method of using the systems and methods described herein, a pedicle screw may be implanted in a target pedicle according to the following steps.

First, preoperative measurements corresponding to the medial/lateral angle of the pedicle are determined using suitable imaging technology, such as for example, MRI. Level the C-arm and then attach the laser reticle to the C-arm using the integrated tilt sensor and LED indicators to align the laser reticle into proper position and the adjustable clamps to lock the reticle in place. Adjust the laser cross-hairs if necessary such that the center of the cross-hairs align with the calibrated center of the C-arm emitter. Select from the navigated guidance system whether fluoroscopy will be used and indicate which side of the body the C-arm is positioned. Ensure the patient is still aligned properly on the table and then measure the cranial/caudal angles. Use the virtual protractor to determine the cranial/caudal angles and then enter the predetermined medial/lateral angles into the system. Return the C-arm to the A/P position to verify again that the patient hasn't moved. Orient the C-arm into owls eye position. Mark the skin where laser cross-hairs direct and then repeat the steps for each pedicle to be instrumented. Make a hole with a pedicle access probe and advance the probe to the spine. Ensure that the pedicle probe is docked on a good starting point with the C-arm and then advance the probe into the pedicle, repeating again for each pedicle to be instrumented.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 13-19 are exemplary views of a laser reticle equipped with an integrated tilt sensor, radiopaque cross-hairs, and laser light, according to one embodiment of the present invention;

DESCRIPTION OF THE PREFERRED EMBODIMENT

Figure 1:
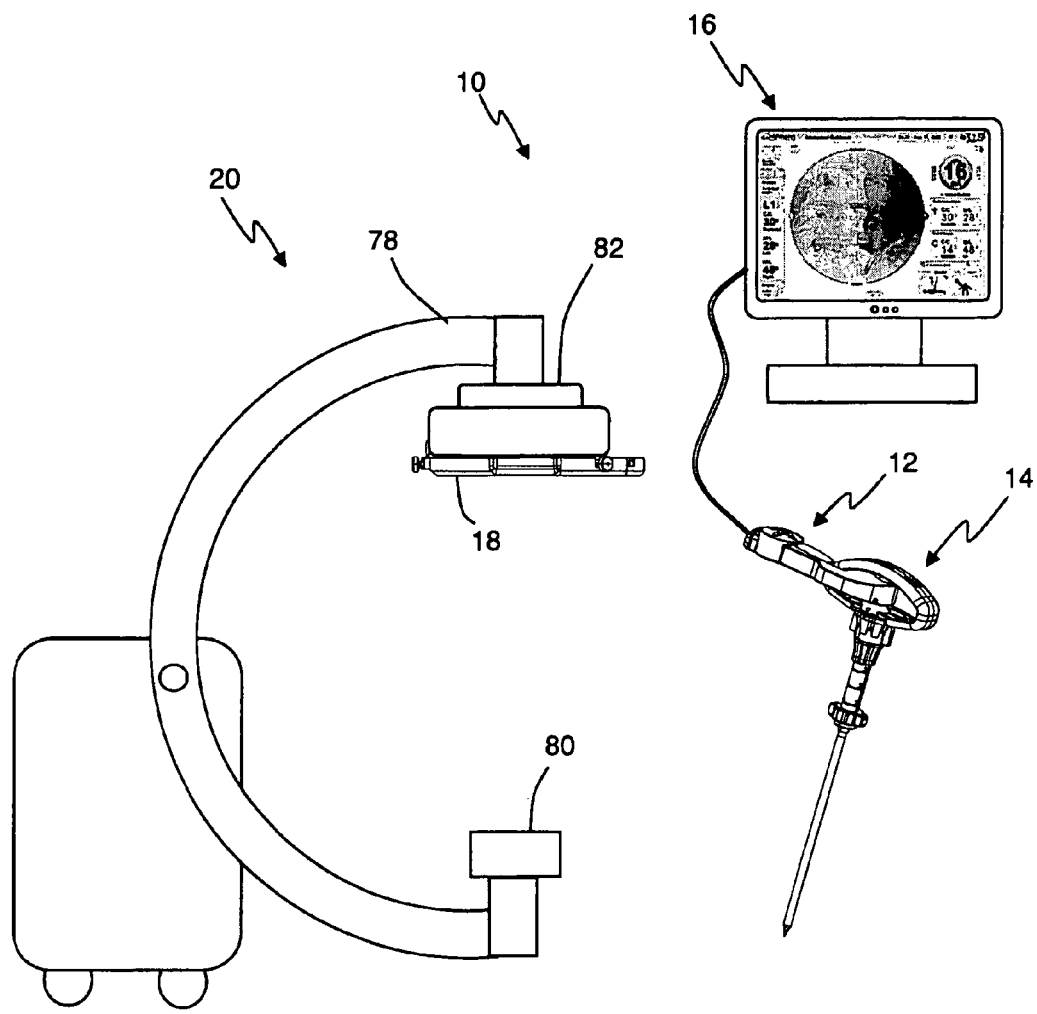
FIG. 1 is an exemplary view of a surgical trajectory system, including a sensor clip, C-arm, laser reticle, surgical instrument and control unit, according to one embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination.

Various embodiments are described of a trajectory monitoring system and surgical uses thereof for enhancing the safety and efficiency of surgical procedures. In one example, set forth by way of example only, the present invention may facilitate safe and reproducible pedicle screw placement by monitoring the axial trajectory of various surgical instruments used during pilot hole formation and/or screw insertion. In another example, set forth by way of example only, intraoperative imaging performance may be improved and radiation exposure minimized by monitoring the precise orientation of the imaging device. In yet another example, monitoring the orientation of surgical access instruments can aid in both the insertion and positioning of the access instruments themselves, as well as, aiding in the later insertion of instruments and/or implants through the surgical access instruments. While the above examples are described in more detail below, it is expressly noted that they are set forth by way of example and that the present invention may be suitable for use in any number of additional surgical actions where the angular orientation or trajectory of instrumentation and/or implants is important. By way of example only, the present invention may be useful in directing, among other things, the formation of tunnels for ligament or tendon repair and the placement of facet screws. Accordingly, it will be appreciated then that while the surgical trajectory system is generally discussed herein as being attached to instruments such as pedicle access tools, C-arms, dilating cannulas, and tissue retractors, other instruments (e.g. drills, screw drivers, taps, inserters, etc. . . . ) may be substituted depending on the surgical procedure being performed and/or the needs of the surgeon. In a further aspect of the present invention, the trajectory monitoring system may be used in conjunction with, or integrated into, a neurophysiology system for assessing one or more of pedicle integrity and nerve proximity, among others functions, as will be described below.

Details of the surgical trajectory system are discussed in conjunction with a first exemplary use thereof for monitoring pilot hole formation (and/or screw insertion) during pedicle screw placement. As used herein, pilot hole formation is meant to encompass any of, or any combination of, creating a hole in bone (such as, for example only, by awling, boring, drilling, etc. . . . ) and preparing a previously formed hole (such as, for example only, by tapping the hole).

With reference now to FIG. 1, there is shown, by way of example only, one embodiment of a surgical trajectory system 10 including a tilt sensor clip 12 (also referred to as "tilt sensor") engaged with a surgical instrument 14, a feedback and control device comprising a control unit 16, and a laser reticle 18 coupled to a C-arm 20. The tilt sensor clip 12 measures its own angular orientation with respect to a reference axis, such as vertical or gravity. The control unit 16 provides feedback related to the angle measurements obtained by the tilt sensor clip 12 for reference by a practitioner and receives user input. The tilt sensor clip 12 attaches to surgical instrument 14 in a known positional relationship such that the angular orientation of the instrument 14 may be determined with respect to the same reference axis. This enables the surgeon to position and maintain the instrument 14 along a desired trajectory path during use. For example, during pilot hole formation, surgical instrument 14 may be aligned and advanced along a pre-determined pedicle axis, thereby decreasing the risk of breaching the pedicle wall.

Figure 2:
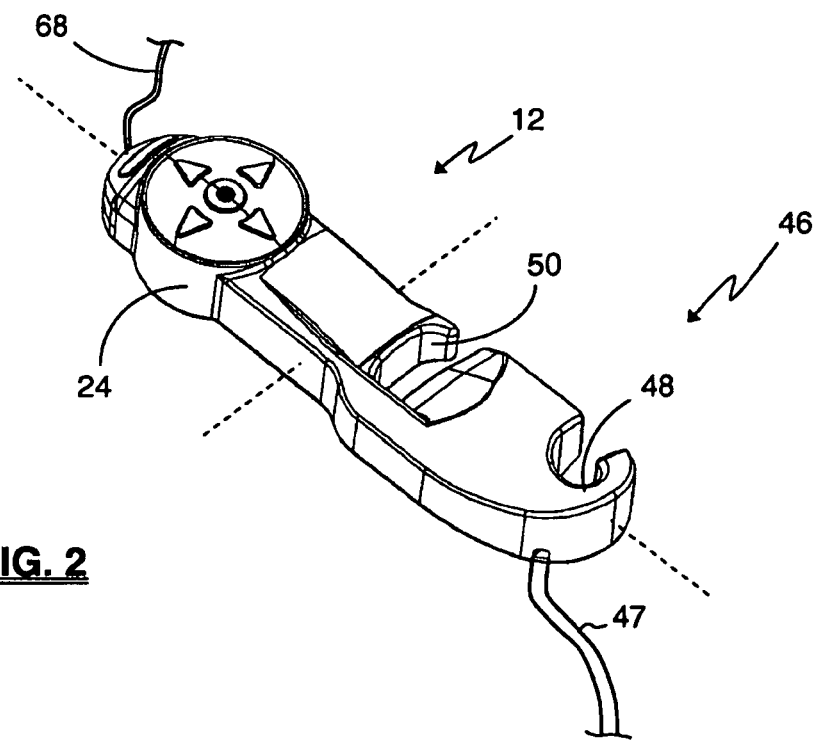
FIG. 2 is a perspective view of a tilt sensor clip of the surgical trajectory system of FIG. 1, according to one embodiment of the present invention.
Figure 3:
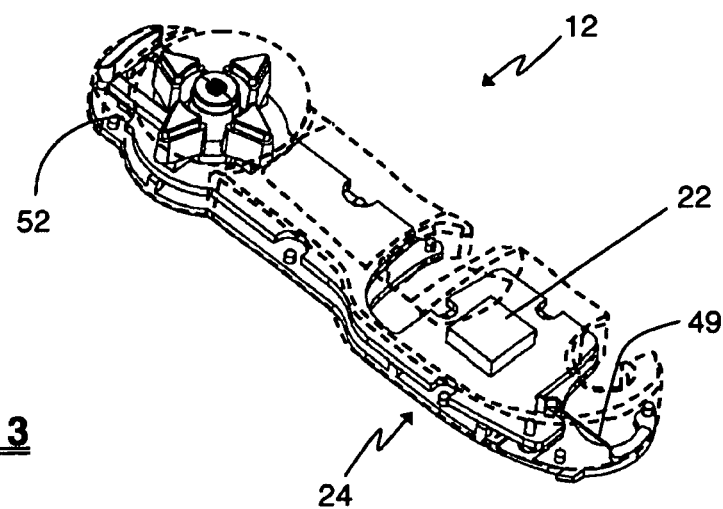
FIG. 3 is a perspective view of a tilt sensor, the outer housing shown in dashed lines to make visible the sensor situated within the housing, according to one embodiment of the present invention.
Figure 4:
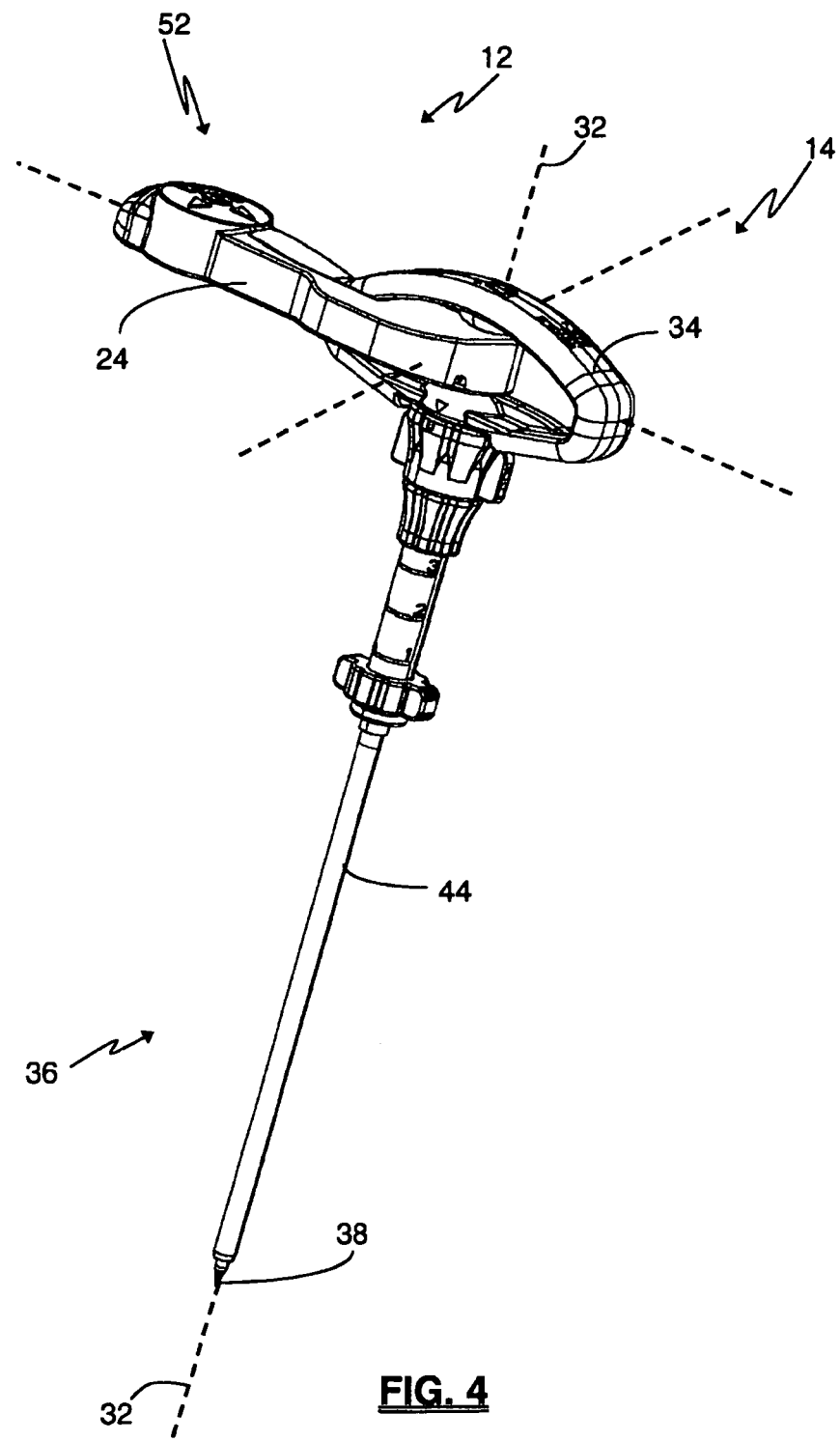
FIG. 4 is a perspective view depicting the bottom of the tilt sensor, according to one embodiment of the present invention.
Figure 5:
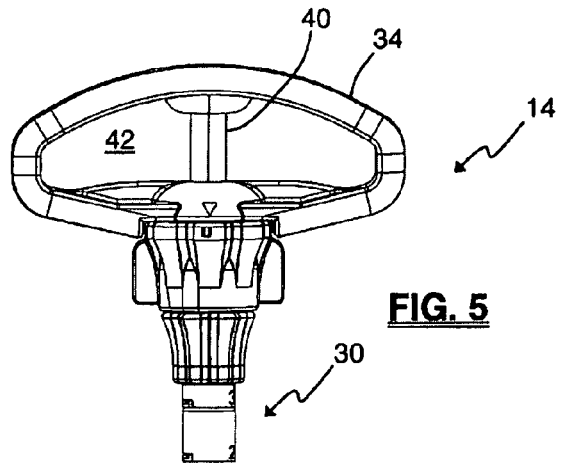
FIG. 5 is a close up view of a handle portion of a surgical instrument, according to one embodiment of the present invention.

Tilt sensor 12, illustrated in FIGS. 2-4, includes a sensor package 22 (FIG. 3) enclosed within a housing 24. The housing 24 may be made from a surgical grade plastic, metal, or any material suitable for use in the surgical field. Housing 24 is configured to snugly couple with the surgical instrument 14 in a known positional relationship, as will be described below.

In one embodiment, sensor package 22 comprises a 2-axis accelerometer that measures angular orientation with respect to the acting direction of gravity. The angular orientation of tilt sensor 12 is measured in a sagittal plane and a transverse plane. By way of example, the orientation of the tilt sensor 12 in the transverse plane represents a medial-lateral angle $A1(i)$ with respect to a patient and the direction of gravity. Orientation in the sagittal plane represents a cranial-caudal angle $A2(i)$ with respect to the direction of gravity and the patient. Sensor package 22 is preferably situated within housing 24 such that when housing 24 is perpendicular to the direction of gravity, the accelerometer registers zero angle in both the sagittal and transverse planes (i.e. the zero-angle position or $A1(i)=0$ and $A2(i)=0$). In other words, both the cranial-caudal angle and medial-lateral angle are equal to zero. Thus, when tilt sensor 12 is fixed perpendicular to the longitudinal axis of the surgical instrument 14, the angular orientation of the instruments longitudinal axis may be determined relative to gravity.

Utilizing only a 2-axis accelerometer, the accuracy of the tilt sensor 12 may be affected by movement around the third, rotational axis. To counter this, measurements should preferably be taken only when at least one of the longitudinal axis 26 and transverse axis 28 tilt sensor 12 are aligned with a selected reference frame, such as for example, the longitudinal axis of the patient's spine (i.e. the tilt sensor 12 should be in approximately the same rotational alignment for each measurement). In one embodiment, this may be accomplished effectively using visual aids to help keep the tilt sensor 12 in line with the reference frame and/or ensure measurements may be taken when the tilt sensor 12 appears to be in this correct rotational position. By way of example only, the sensor clip 12 attaches to the instrument 14 such that a free end of the clip may "point" to the patients feet when the sensor 12 is in the correct rotational position. In the event the surgical instrument 14 is inadvertently or purposely rotated during use, the practitioner need only continue, or reverse rotation until the tilt sensor 12 again appears to be perpendicular to the long axis of the spine. Alternatively (or in addition to), various markings or other indicia (not shown) may be included on one or more of the tilt sensor 12 and the surgical instrument 14 to ensure proper alignment prior to obtaining measurements.

In an alternative embodiment, the sensor package 22 may be configured such that it may account for, or at least measure, rotation (e.g. a "3-axis sensor"). In one embodiment, the sensor package 22 includes a 2-axis accelerometer augmented by a gyroscope (not shown), which may comprise any number of commercially available gyroscopes. While the accelerometer again measures the angular orientation of the tilt sensor 12 with respect to gravity, the gyroscope detects movement about the rotational or z-axis. By monitoring the rate of rotation and time, the system 10 may determine the degrees of rotation imparted on the surgical instrument 14 (and tilt sensor 12). The control unit 16 may indicate to the user that the sensor 12 is not aligned in the correct reference frame such that the user may take steps to correct the alignment prior to taking measurements. The control unit 16 may display feedback according to any number of suitable methods. By way of example, the feedback may utilize numeric indicia to indicate the degree of misalignment, color indicia, such as red or green indicating the rotational status (e.g. aligned or misaligned), audible alert tones (e.g. low frequency tones for non-alignment and high frequency tones for proper alignment or visa versa or any combination thereof), etc. . . . . Alternatively, the system 10 may be configured to correct the angle data output based on the degree of rotation detected. In this manner, angle data from the tilt sensor 12 may be acquired from any rotational position. A button (not shown) may be provided on the tilt sensor 12 and/or control unit 16 to initially zero the sensor package 22 when it is aligned with the reference frame.

In another embodiment, the sensor package 22 accounts for rotational movement by utilizing magnetometers (not shown) in conjunction with the 2-axis accelerometers, where the magnetometer may comprise any number of commercially available magnetometers. The sensor package 22 includes a triplet of magnetic sensors oriented perpendicular to each other, one pointing in the x-axis, one in the y-axis, and third pointing in the z-axis. The magnetic sensors in the x and y axis act as a compass and calculate a heading of tilt sensor 12 relative to magnetic north. The third magnetometer in the z-axis and the x and y axis accelerometers monitor the tilt permitting the "compass" to work when it is not level to the ground. Since the sensor package 22 monitors for angular orientation in the x-axis and y-axis and maintains a constant heading reference, the system 10 may calculate the amount of axial rotation relative to an established reference frame (i.e. the patient). The control unit 16 may again be configured to indicate the rotational status of the tilt sensor 12 to the user, allowing them to realign the sensor 22 with the proper reference frame prior to establishing a reading. The feedback device 16 may again utilize numeric indicia to indicate the degree of misalignment, color indicia, such as red or green indicating the rotational status (e.g. aligned or misaligned), audible alert tones (e.g. low frequency and/or volume tones for non-alignment and high frequency and/or volume tones for proper alignment or visa versa or any combination thereof), etc. . . .

A surgical instrument 14, according to one embodiment, is illustrated in FIG. 4. Surgical instrument 14 may comprise a pedicle access probe. By way of example only, instrument 14 may be any of the insulated pedicle access probes described in detail in the commonly owned and co-pending U.S. patent application Ser. No. 11/448,237, entitled "Insulated Pedicle Access System and Related Methods," and filed on Jun. 6, 2006, the entire contents of which is incorporated by reference as if set forth herein in its entirety. Instrument 14 comprises generally a probe member 30, having a longitudinal axis 32, and a handle 34. Probe member 30 may be embodied in any variety of configurations that can be inserted through an operating corridor to a pedicle target site and bore, pierce, or otherwise dislodge and/or impact bone to form a pilot hole for pedicle screw placement. Probe member 30 may be generally cylindrical in shape, however, probe member 30 may be provided in any suitable shape having any suitable cross-section (e.g. generally oval, polygonal, etc. . . . ). A distal region 36 of probe member 30 may have a shaped tip 38 formed of any number of shapes generally suited to effect pilot hole formation, such as, by way of example only, a beveled point, double diamond, drill bit, tap, and a generally tapered awl. A proximal region 40 of probe member 30, accessible via a cutout 42 in the handle 34, may be configured to couple the housing 24 of sensor clip 12. Probe member 30 may be composed of any material suitable for surgical use and strong enough to impact bone to form a pilot hole. In one embodiment, the material may also be capable of conducting an electric current signal to allow for the use of neurophysiologic monitoring. By way of example only, probe member 30 may be composed of titanium, stainless steel, or other surgical grade alloy. The distal region 36 may also be equipped with a retractable insulation sheath 44. The sheath 44 ensures maximum efficiency of an electrical stimulation signal that may be delivered to the shaped tip 38 during neurophysiologic monitoring that may be conducted in conjunction with the surgical trajectory monitoring of system 10, as described below.

Handle 34 may be permanently or removably attached to probe member 30 along the proximal region 40. Handle 34 may be shaped and dimensioned in any of a number of suitable variations to assist in manipulating probe member 30. By way of example only, the handle 34 may be generally T-shaped such as the handle pictured in FIG. 4. Other suitable shapes for handle 34 may include, but are not necessarily limited to, generally spherical, ellipsoidal, and egg-shaped. Sensor clip 12 forms a sturdy connection with probe member 30 such that the tilt sensor 12 is maintained in a position perpendicular to the longitudinal axis 32 of probe member 30. When the longitudinal axis 32 of probe member 30 is parallel to the direction of gravity, the tilt sensor 12 is perpendicular to the direction of gravity (i.e. the zero-angle position). In other words, when the longitudinal axis 32 of probe member 30 is parallel to the acting direction of gravity, both the cranial-caudal angle and the medial-lateral angle will be zero-degrees.

Figure 6:
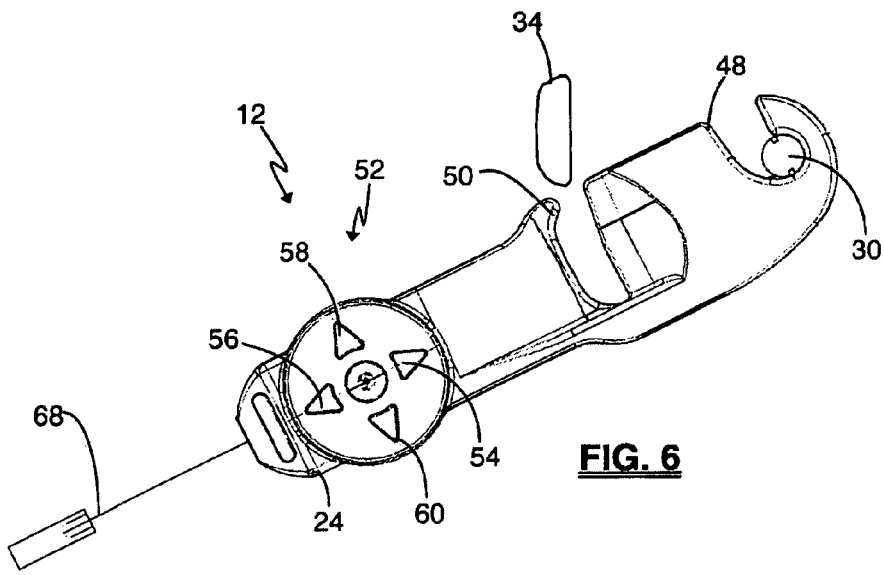
FIGS. 6-7 illustrate a sensor clip connector used to attach the tilt sensor to a surgical instrument, according to one embodiment of the present invention.
Figure 7:
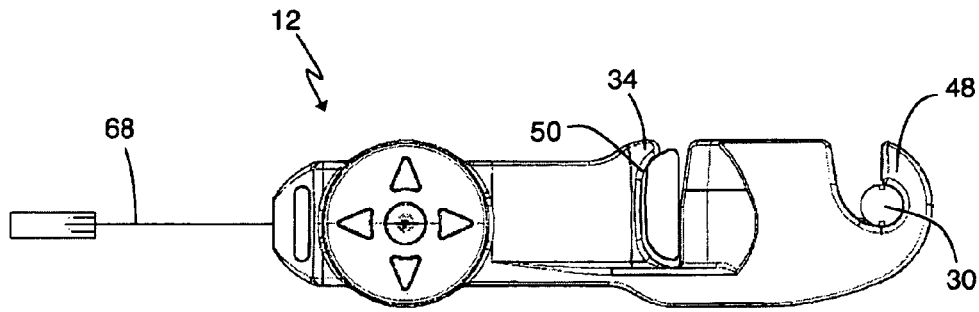

With reference to FIGS. 2-7, sensor clip 12 will be further described. To secure the sensor clip 12 to surgical instrument 14, housing 24 includes a fastener end 46 dimensioned to snugly receive at least a portion of instrument 14. By way of example only, fastener end 46 comprises an end hook 48, and a handle receiver 50. To maintain a snug fit with the instrument 14, the end hook 48 is configured to snap on and tightly grasp the proximal region 40, as illustrated in FIG. 4. To attach the clip 12 to instrument 14, the end hook 48 is fitted onto the proximal end 40 of the instrument 14. Thereafter the housing 24 is rotated until the handle receiver 50 fully engages with the handle 34 of the instrument 14 (FIGS. 6-7). FIG. 6 illustrates, by way of example only, a the proximal end 40 (shown in cross-section) tightly positioned within the end hook 48 and before engaging the handle 34 (also shown in cross-section) in the handle receiver 50. FIG. 7 illustrates the handle 34 (again in cross-section) after the clip 12 has been rotated into position with the handle 34 fully engaged in the handle receiver 50. Once fully engaged, fastener end 46 is dimensioned to prevent the unintentional disengagement of instrument 14 from the sensor clip 12. When engaged, sensor clip 12 extends perpendicular to the longitudinal axis 32 of instrument 14. To release the surgical instrument 14, the clip 12 may be rotated to disengage the handle receiver 50 from the handle 34, and the end hook 48 may be released.

Also illustrated in FIGS. 2-4 and 6-7 is a secondary feedback system 52, integrated into the sensor clip 12. By way of example only, secondary feedback system 52 comprises a collection of LED light indicators to provide an indication of the angular orientation of surgical instrument 14 relative to a reference orientation. The collection of LED's includes four LED directional lights 54-60, a central LED light 62, and a function LED light 64. The four LED directional lights 54-60 are independently operated to provide an indication to the user of the sensors 12 (and hence, the instrument 14) angular position relative to a desired position (as determined, for example, by predetermined angle measurements captured by or inputted into the system 10). By way of example only, two opposing LED lights 54 and 56 may correspond to the orientation of the sensor 12 in the cranial-caudal direction and the other two opposing LED lights 58 and 60 may correspond to the orientation in the medial-lateral directions. According to one example, the LED directional lights 54-60 will light to indicate the direction in which the instrument 14 needs to be adjusted to align with the desired trajectory. Thus, (by way of example) if the instrument is properly aligned in the medial-lateral direction but not in the cranial-caudal direction then one if lights 54 and 56 will light up to indicate that the instrument needs to be moved in the direction of the lighted LED (either 54 or 56 depending upon whether the instrument needs to be adjusted in the cranial direction or the caudal direction), if however, the instrument 14 is not aligned in either the cranial-caudal direction or the medial-lateral direction, one each of LEDS 54-56 and 58-60 will light to indicate which direction (i.e. either cranial or caudal and either left or right, respectively) that the instrument 14 needs to be adjusted to align with the desired trajectory.

The control unit 16 is communicatively linked to tilt sensor clip 12 and functions to provide feedback to the surgeon regarding the angle of the tilt sensor 12 and instrument 14 relative to the desired angles (e.g. predetermined medial-lateral and cranial-caudal angles) as well as receive user input related to various aspects of the trajectory system 10. By way of example only, the control unit 16 includes a display 66 which may show one or more or alpha-numeric, graphic, and color indicia indicative of the sensor 12 trajectory, imported fluoroscopic or other images, patient and or user information, and other system related information. The control unit 16 may also receive user input, such as by way of example, user selectable parameters and/or preferences, procedure related data (including but not necessarily limited to predetermined medial-lateral angles, predetermined cranial-caudal angles), etc. . . . By way of further example, the control unit 16 display 66 may include tools which may be utilized by the user, such as by way of example only, a virtual protractor for predetermining angles. Various features and aspects of the control unit 16 and display 66 functionality are discussed in more detail below. In addition to display 66, the control unit 16 may be configured to utilize audio indicators as well. By way of example, the control unit 16 may utilize a code based on the emission of audio tones to indicate the angular orientation of the tilt sensor 12 relative to predetermined reference angles corresponding to the desired trajectory. One method for implementing an audio code involves varying one or more of the volume, pitch, frequency, pulse rate, and length of the audio tone based on the determined orientation of the sensor 12 relative to the predetermined orientation ranges. Audio feedback may be used alone, or in combination with one or both of the alpha-numeric, graphic, and color indicia previously described. In one embodiment, a first audible signal may be indicative of an optimal variance between the trajectory of the instrument and at least one of the first and second determined angular relationships between the sensor 12 and the reference direction. A second audible signal may be indicative of an unacceptable variance between the trajectory of the instrument and at least one of the first and second determined angular relationships between the sensor 12 and the reference direction. A third audible signal may be indicative of an acceptable yet not optimal variance between the trajectory of the instrument and at least one of the first and second determined angular relationships between the sensor 12 and the reference direction.

The communication link between the sensor clip 12 and may be accomplished via hard-wire (e.g. data cable 68 of FIG. 1) and/or via wireless technology, in which case the tilt sensor 12 and control unit 16 may include additional hardware commonly used for enabling such wireless communication. If communicatively linked to the feedback device 16 via hard-wire, the position of the feedback device 16 should be such that the tilt sensor 12 may move freely without tensioning the data cable 68.

According to another aspect of the present invention, the laser reticle 18 is attached to C-arm 20 (fluoroscope) to aid in orienting the C-arm 20 into an advantageous position. By way of example only, it may advantageous during pedicle screw placement to orient the C-arm 20 in an owl's eye or oblique position (i.e. the trajectory of the x-ray beam is directly in line with the angular trajectory of the pedicle). The reticle 18 is equipped with an integrated sensor package 70. Sensor package 70 comprises an accelerometer similar to the sensor package 22 of clip 12 (such that a repeat discussion is not necessary). Including a tilt sensor package 70 in the reticle allows the system 10 to determine the angular position of the reticle 18, and hence the C-arm 20 to which it is attached, with respect to gravity. The C-arm 20 and laser reticle 18 will now be discussed in more detail.

Figure 8:
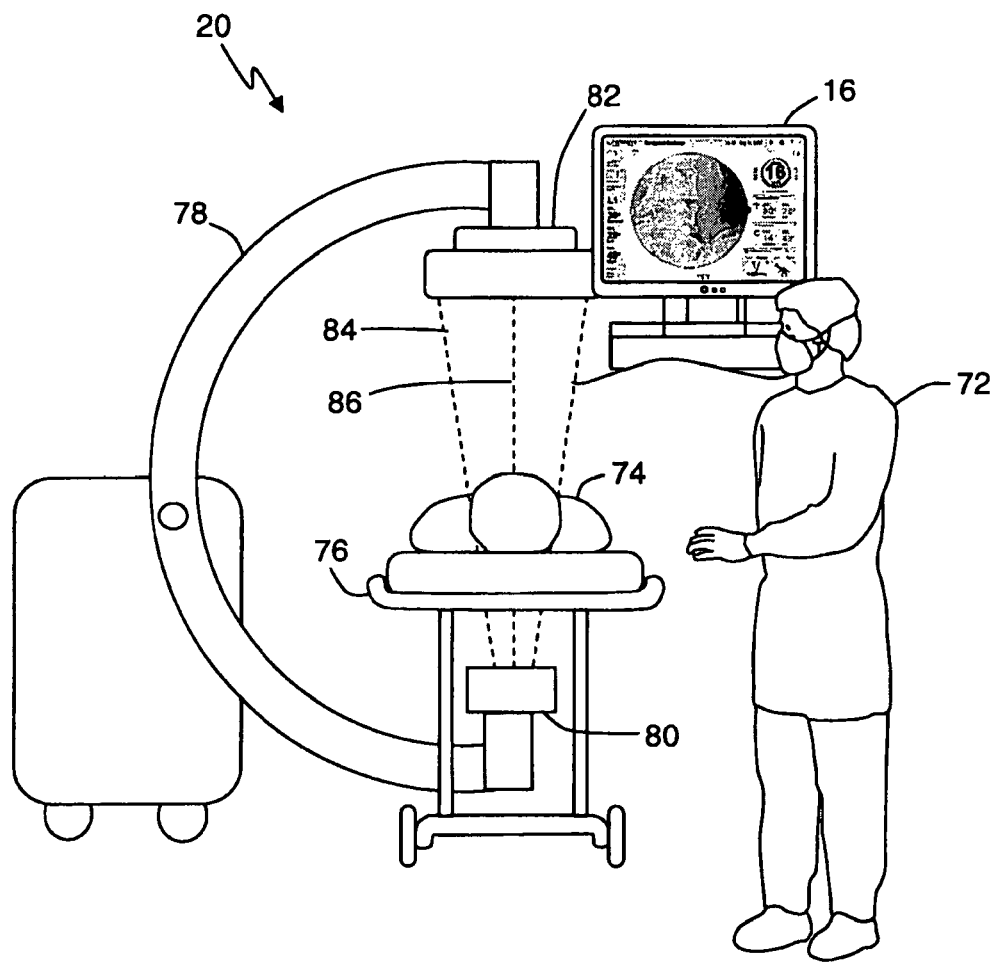
FIG. 8 is an illustration of an operating theater equipped with a surgical table, C-arm fluoroscope, fluoroscope monitor, practitioner, and patient.

With reference to FIG. 8 there is shown a typical operating theatre in which a practitioner 72 may perform surgical procedures on a patient 74. The patient 74 is positioned on a radiolucent operating table 76. Arrayed around the table 76 are a standard C-arm 20, comprising a frame 78, a signal transmitter 80, and a signal receiver/image intensifier 82, and the control unit 16 which receives and displays video feed from the C-arm 20, allowing live fluoroscopic images to be integrated with the trajectory monitoring system 10. In use, an x-ray beam 84, having a central axis 86, may be directed from the signal transmitter 80 through a desired area of patient 74 and picked up by the signal receiver 82. An image of the patient's 74 body tissue located in the path of beam 84 may be generated and displayed on the display 66. It should be appreciated that while the C-arm 20 is discussed herein generally for use during spine surgery to capture images of the spine, such discussion is for exemplary purposes only. It will be understood that the C-arm 20 and laser reticle 18 combination may be utilized for imaging in a wide variety of surgical procedures.

Figure 9:
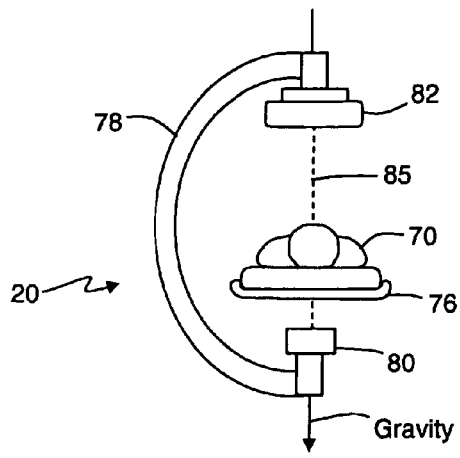
FIG. 9 is a front view of the C-arm of FIG. 8 oriented in an A/P position for generating an A/P fluoroscopic image.
Figure 10:
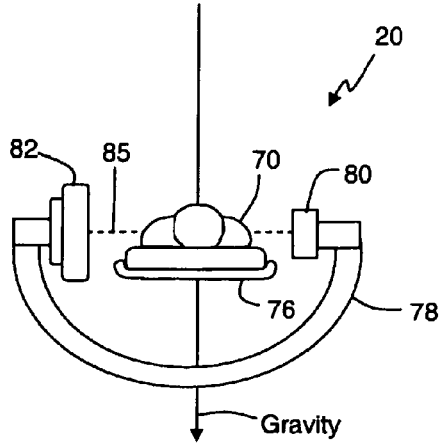
FIG. 10 is front view of the C-arm of FIG. 8 oriented in a lateral position for generating a lateral fluoroscopic image.
Figure 11A:
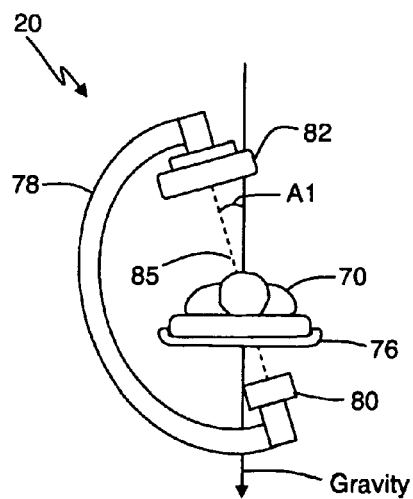
FIGS. 11A-11B are front views of the C-arm of FIG. 8 oriented according to desired medial-lateral angles between the A/P position of FIG. 9 and the lateral position of FIG. 10.
Figure 11B:
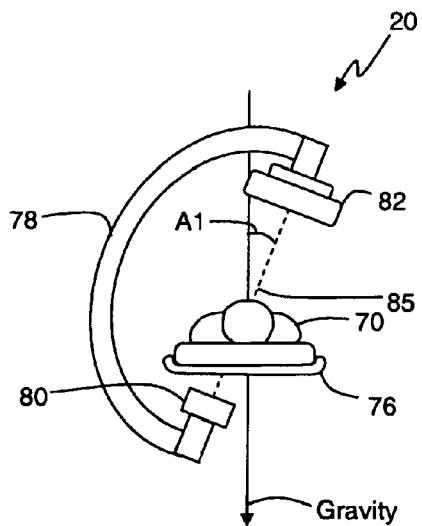
Figure 12A:
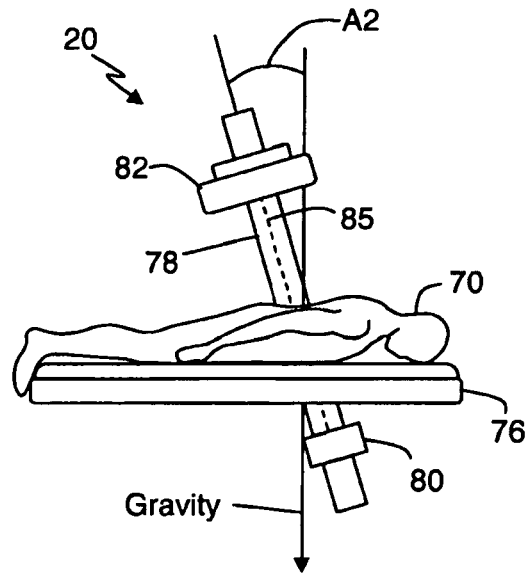
FIGS. 12A-12B are side views of the C-arm of FIG. 8 oriented according to various cranial-caudal angles.
Figure 12B:
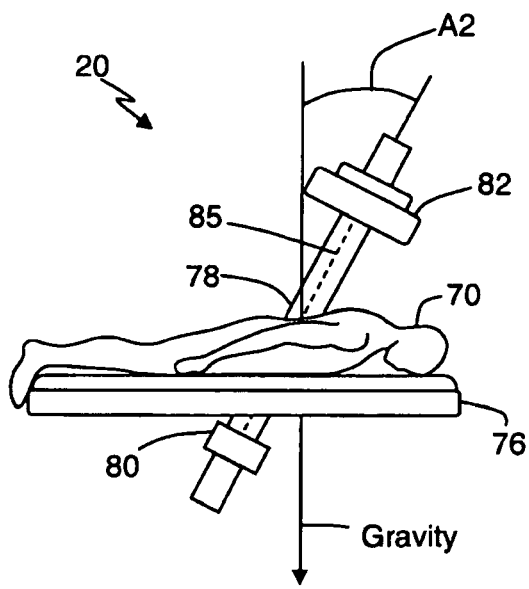

As illustrated in FIGS. 9-12, the C-arm frame 78 may be adjusted to alter the path of the beam 84, and thus the image that is generated. In FIG. 9 the frame 78 is oriented such that beam 84 travels parallel to the direction of gravity. With the patient in the prone position, as shown herein, this position of frame 78 generates an anterior-posterior (A/P) image. This position of C-arm 20 is referred to hereafter as the A/P position. Rotating the frame 90° in a medial-lateral direction (through a transverse plane), as depicted in FIG. 10, directs the beam 84 perpendicular to the direction of gravity and generates a lateral image. This position of the C-arm 20 is referred to as the lateral position. A/P and lateral images may both be useful during a spinal procedure and the C-arm may be adjusted between the A/P and lateral positions numerous times during the procedure. As illustrated in FIGS. 11A-11B, the frame 78 may also be oriented in any position within the transverse plane between the A/P and lateral positions, such that the beam 84 forms an angle $A1(c)$ (the medial-lateral angle) between zero and 90° with respect the direction of gravity. Furthermore, as illustrated in FIGS. 12A-12B, the frame 78 may also be rotated in a cranial-caudal direction (within a sagittal plane) such that the beam 84 forms another angle $A2(c)$ (the cranial-caudal angle) with respect to the direction of gravity. By way of example only, the C-arm 20 may be oriented such that one or both of angles $A1(c)$ and $A2(c)$ correspond to the desired axis of trajectory of a pedicle bone, i.e. angles A1 and A2 (owl's eye or oblique view), as will be discussed in more detail below.

By attaching the reticle 18 with integrated tilt sensor package 70 to the C-arm 20 in a known positional relationship, the angular orientation of the C-arm with respect to the reference axis (gravity) may be determined. This enables the practitioner to quickly position the C-arm 20 in a known orientation, such as, by way of example only, the precise orientation in which a previous image was acquired. Doing so may eliminate the time and extra radiation exposure which is often endured while acquiring numerous images while "hunting" for the right image. Attaching the sensor 70 (via reticle 18) to the C-arm may further enable the practitioner to determine the angular orientation of anatomical structures within the patient (e.g. vertebral pedicles), as will be described below. This may be advantageous, for example only, when the practitioner is performing pedicle fixation and preoperative images (such as the MRI or CAT images which may be used to determine the pedicle axis angle A1) are not available for preoperative planning, as described above.

Figure 14:
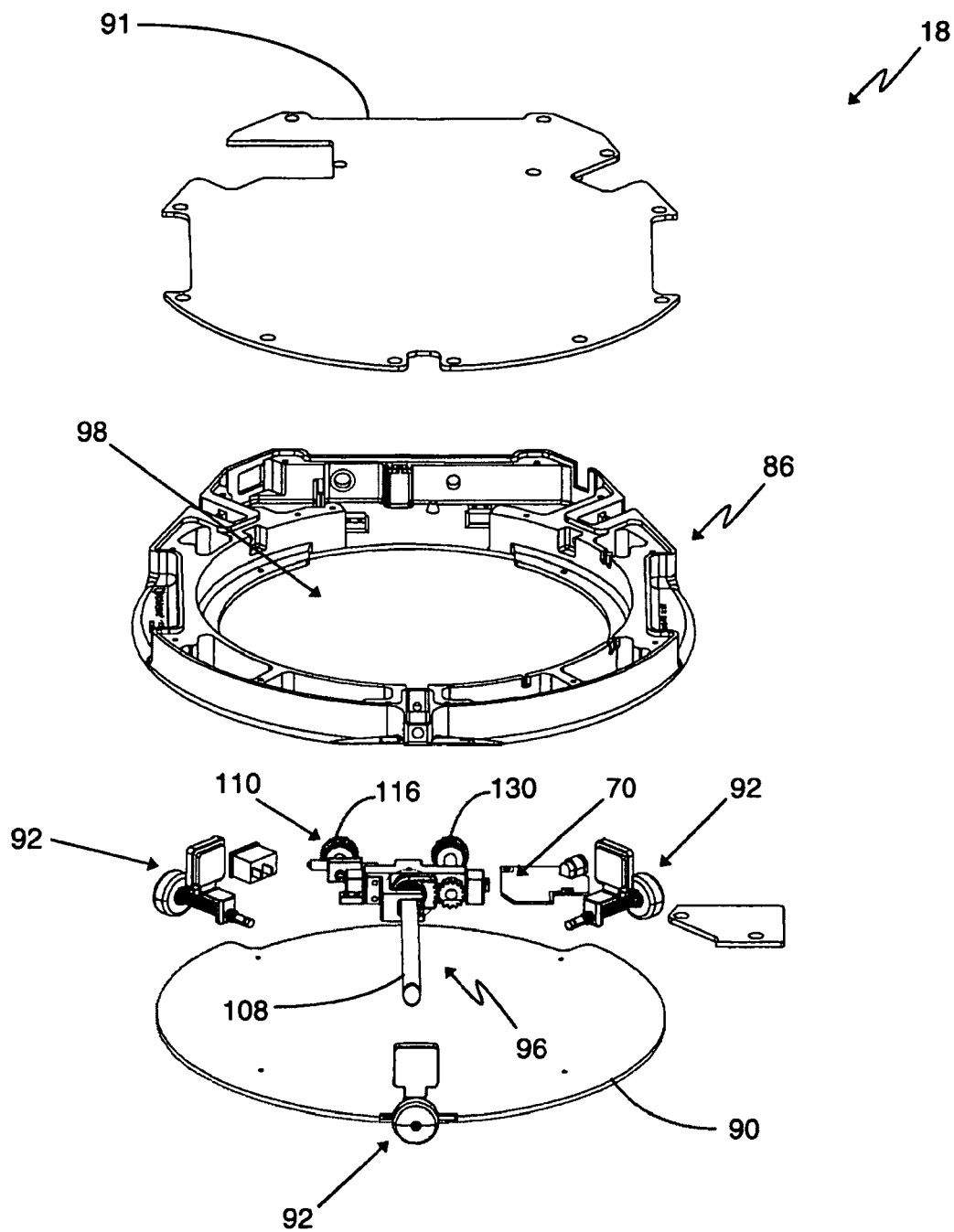

According to one embodiment laser reticle 18 may be attached to the receiver 82 of the C-arm 20, as pictured in FIG. 1. FIG. 13 illustrates one embodiment of laser reticle 18 comprising a reticle frame 1152, radiopaque cross hair marker 1154, radiolucent front cover 1158, radiolucent back plate 1159, adjustable clamps 1160, sensor tilt LED indicators 1164, and an adjustable laser emitter system 96. FIG. 14 illustrates an exploded view of laser reticle 18. The reticle 18 is configured to generate a reference cross-hair viewable in fluoroscopic images generated by C-arm 20. Other benefits may also be gained by using laser reticle 18, such as the benefit of producing a laser cross-hair target on the skin of the patient. This benefit will be discussed in greater detail below. FIG. 13 illustrates one embodiment of laser reticle 18 comprising a reticle frame 86, radiopaque cross hair marker 88, radiolucent front cover 90, radiolucent back plate 91, adjustable clamps 92, sensor tilt LED indicators 94, and an adjustable laser emitter system 96. FIG. 14 illustrates an exploded view of laser reticle 18.

Reticle frame 86 may be made of aluminum material in a generally circular configuration with an inner window opening 98. The purpose of window opening 98 is to allow a fluoroscopic image to pass through window 98 unobstructed by the metal material of frame 86. It should be understood that various other suitable materials and configurations may be used in place of, or in addition to, the reticle frame described above. Other reticle frames may include, but are not necessarily limited to, a generally rectangular configuration with square window opening. With reference to FIGS. 13-14, reticle frame 86 has a front, leading edge 100 and a back edge 102.

Figure 15:
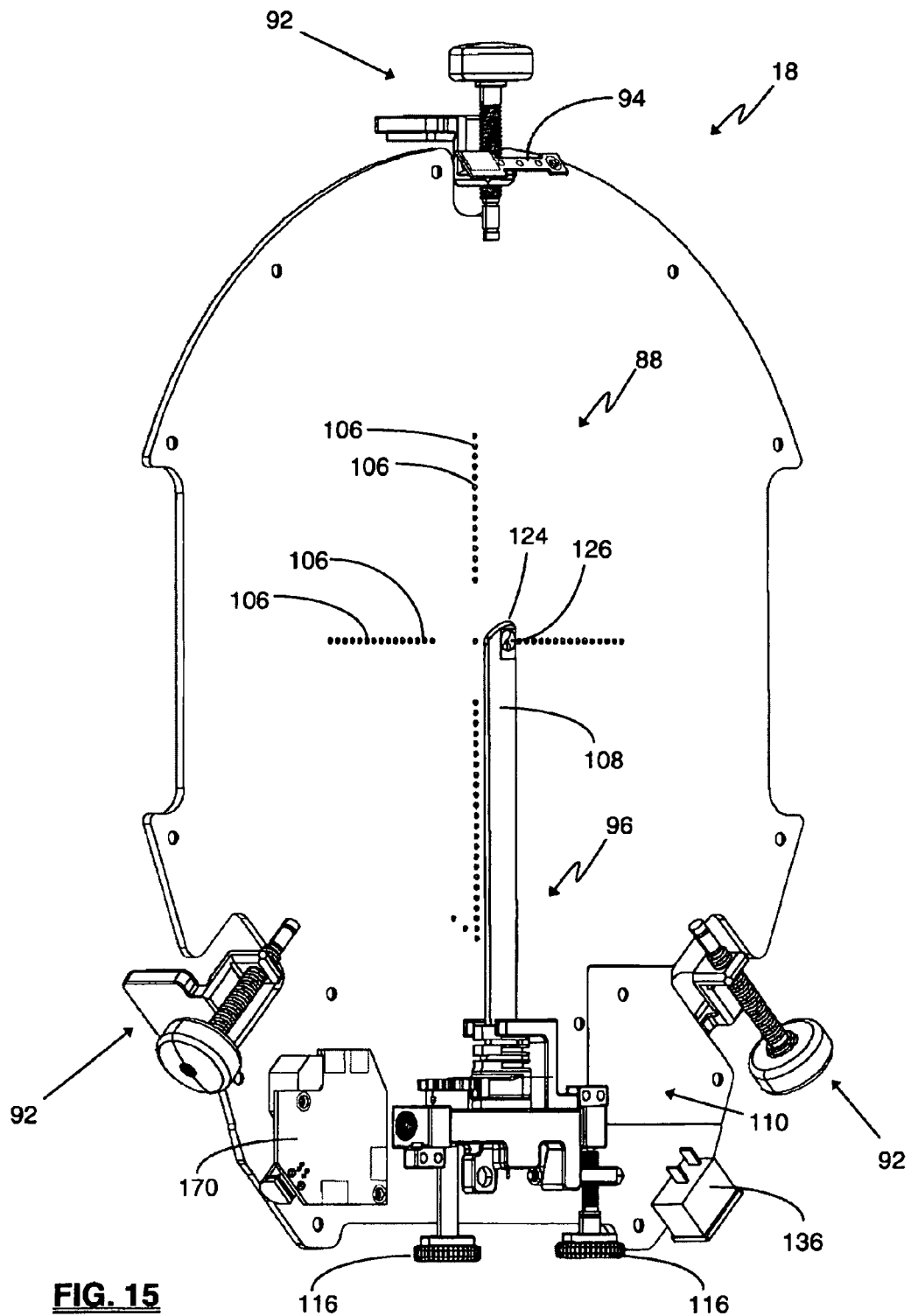
Figure 16:
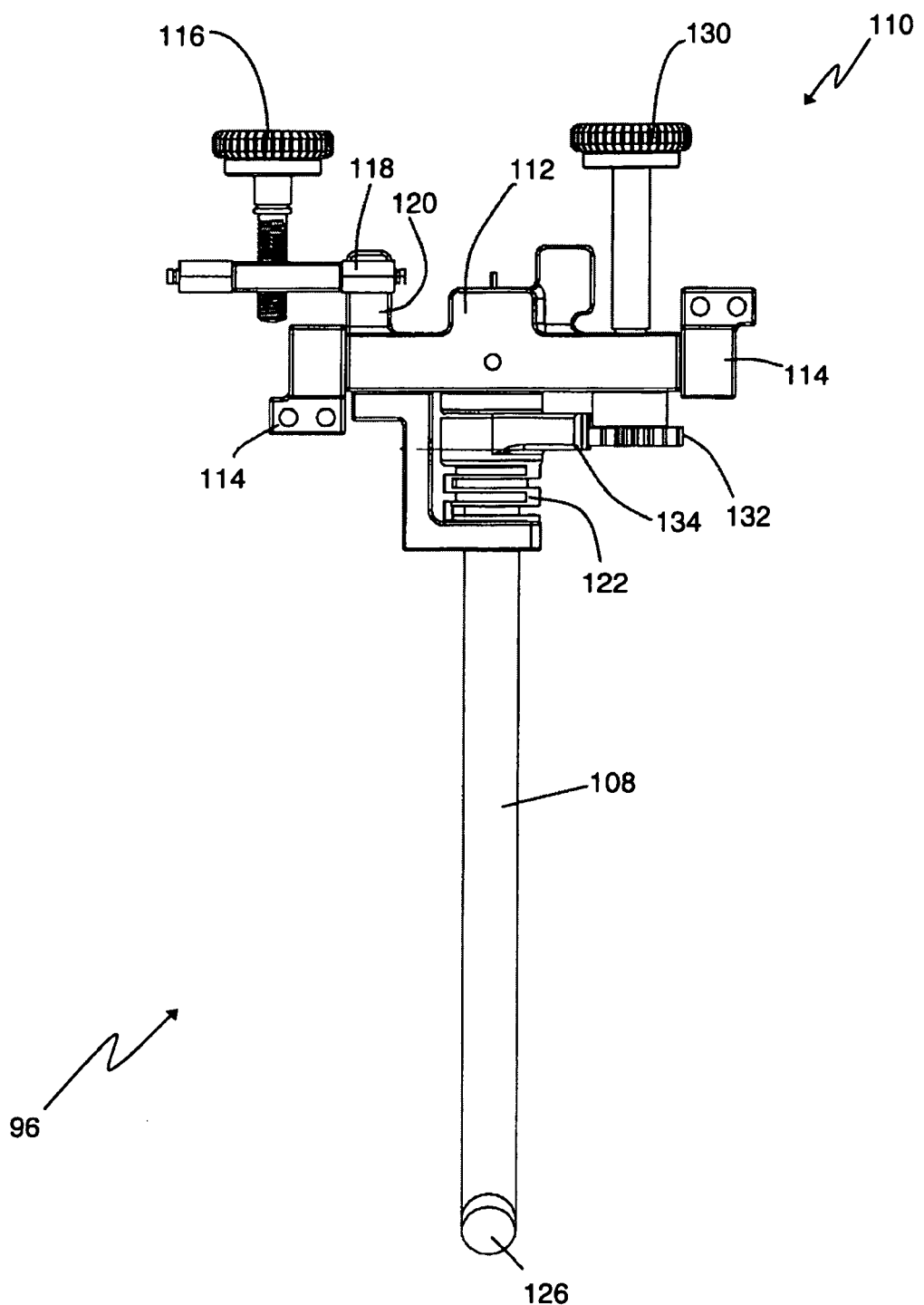
Figure 17:
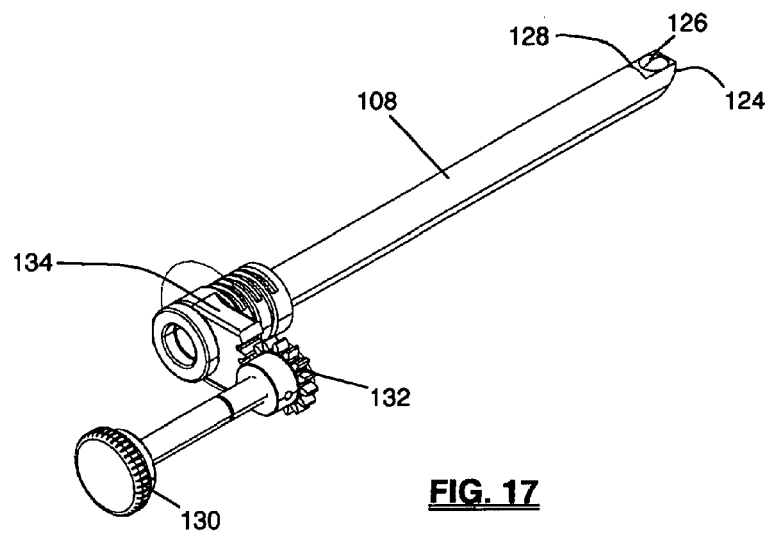
Figure 18:
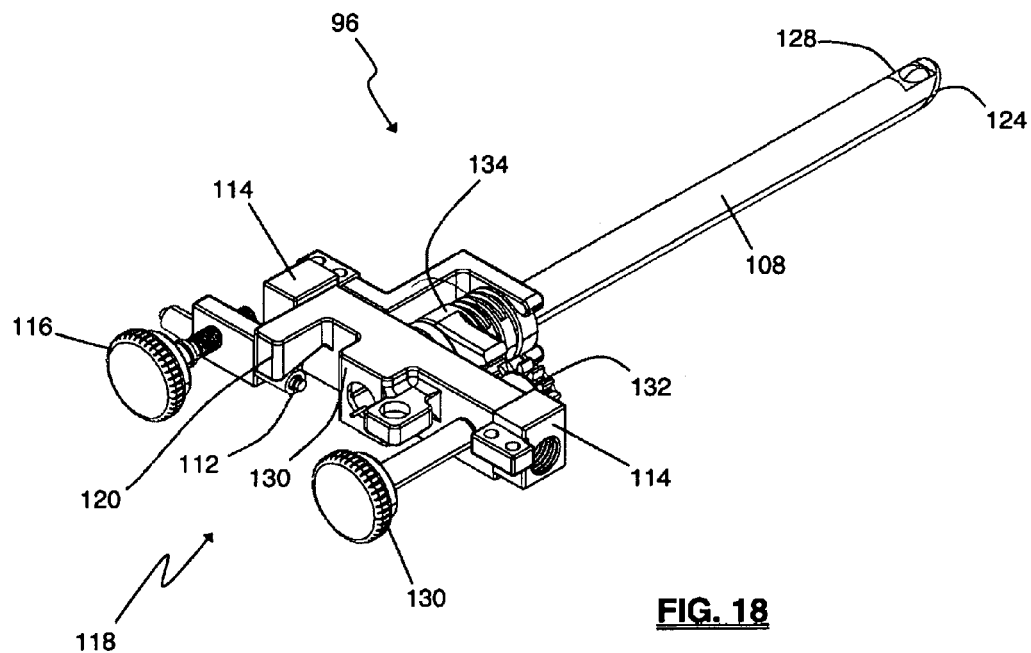
Figure 19:
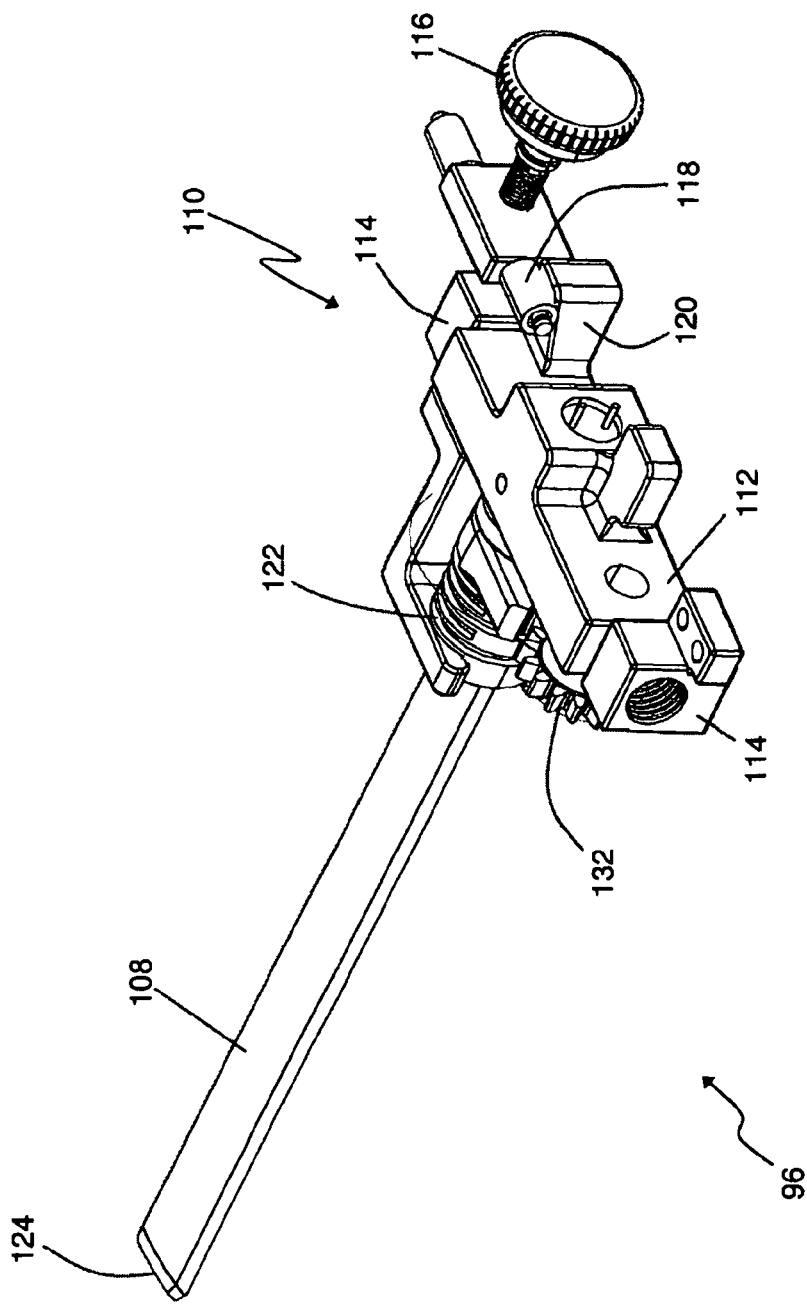

FIG. 15 illustrates, by way of example only, one embodiment of radiopaque cross hair marker 88. When attached to the receiver 82 of the C-arm 20, radiopaque cross hair 88 is captured in the fluoroscopic image, giving the operator a reference point to the center of the receiver 82. Moreover, the cross-hairs 88 provide vertical reference line in the fluoroscopic image, as discussed below. By way of example only, the radiopaque cross hair marker 88 may be produced from metal BB's 106 fixed onto the radiolucent back plate 91. With reference to FIG. 15, the cross-hair pattern may comprise a single radiopaque BB 106 as the exact center, with four lines of BB's extending out from the center, along the vertical and horizontal axis of reticle 18. Radiopaque cross hair marker 88 may also comprise a longer, vertical arrow which points to gravity when the reticle is properly mounted and the C-arm is in the lateral position. Although the radiopaque marker 88 is described as being formed by metal BB's fixed in a cross-hair pattern onto a radiolucent case, it can be appreciated that other suitable materials and configurations may be used to produce the same radiopaque target effect.

Laser reticle 18 is preferably mounted to the C-arm 82 with the C-arm in the lateral position, which allows gravity to help correctly position the laser reticle 18 and the corresponding radiopaque cross-hair marker 88. Laser reticle 18 includes a set of adjustable clamps 92, a sensor package (70), and sensor tilt LED indicators 94 to assist in the positioning of laser reticle 18 on to C-arm 82. As mentioned, a sensor package 70, similar to sensor package 22 is integrated within the housing of the laser reticle 18. The sensor package 70 is preferably situated such that it is orthogonal to the reference markers 88, and when the tilt sensor 70 is perpendicular to the direction of gravity, the sensor registers a zero angle in both the sagittal and transverse planes. The sensor package is communicatively linked to sensor tilt LED indicators 94, located near the superior edge of the laser reticle 18, and the center LED indicator will light up when the tilt sensor is perpendicular to the direction of gravity. If the tilt sensor is not perpendicular to the direction of gravity, the sensor tilt LED indicators 94 will prompt the operator to tilt the laser reticle 18 in the direction of the lit LED indicator until the center LED indicator lights up, indicating that the sensor package 70 is perpendicular to the direction of gravity. Once the laser reticle 18 is leveled out in this position, the operator may tighten the adjustable clamps 92 to securely attach the laser reticle 18 on to the C-arm receiver 82. The use of adjustable clamps 92 allows laser reticle 18 to attach to nearly any C-arm. Laser reticle 18 may be shaped in a generally circular pattern to correspond to the circular shape of the receiver 82. However, laser reticle 18 may be shaped and dimensioned in any of a number of suitable variations including, but not necessarily limited to, generally rectangular, triangular, ellipsoidal, and polygonal.

Laser reticle 18 also includes an adjustable laser cross hair emitter, which may generate a cross-haired target onto the patient's skin at the surgical access site. Adjustment knobs may be used to adjust the laser emitter along the sagittal and transverse planes. The laser is generated from the center of the laser reticle 18, and when looking down the axis protruding from the center of the reticle 18 the point of laser generation directly overlaps the center point of the radiopaque cross hair 88. An advantage of providing an adjustable laser emitter is to allow the operator to point the laser down any desirable path (and thus correct for deformities in the C-arm frame that occur over time). In particular, the operator may adjust the laser emitter so that it propagates directly towards the center of the C-arm signal transmitter 80 and down the central axis 85 of the x-ray beam 84. Thus, a perfect vector will be created down the central axis 85 of the x-ray beam 85, which may assist the surgeon in determining a preferred starting point for skin penetration when performing, by way of example only, a pedicle screw placement procedure, as it will precisely mark with the laser cross hair the skin incision site above and in line with the pedicle axis when the C-arm 20 is oriented in the owls eye position When properly adjusted, the laser cross-hairs will be aligned with the radiopaque cross-hairs 88. It will be appreciated that the perfect vector benefit may be suitable for use in any number of additional surgical actions where the angular orientation or trajectory of instrumentation and/or implants is important. It is also appreciated that although the laser emitter is described as emitting a cross-haired pattern, the emitted laser may be shaped in any of a number of suitable variations including, but not necessarily limited to, a bulls-eye, or a single point.

FIGS. 16-19 illustrate an adjustable laser emitter system 96 of the laser reticle 18 that allows the laser emitter to move both up and down and left and right. The laser emitter system comprises a plastic (and radiolucent) light tube 108 extending to the center of the reticle 18 from an adjuster assembly 110 coupled to backplate 91. To adjust the laser emitter 96 up and down, the light tube 108 is coupled to a rocker bar 112 forming part of adjuster assembly 110. A pair of circular apertures (not shown), one in each end of rocker bar 112, pivotally couple the rocker bar to circular set screws (also not shown) extending inward from anchors 114. A vertical adjustment knob 116 translates a roller 118 along an incline ramp 120 extending from the rocker bar 112. As the roller 116 engages the incline ramp 120 the rocker bar 112 pivots around the set screws coupling the rocker bar to anchors 114 and the light tube 108 moves along a vertical plane. A tensioned spring 122 causes the rocker bar 112 to return to its natural position when the roller 118 is translated back down the ramp 120. A laser emitter situated in rocker bar 112 and coaxial with the light tube 108 directs laser light through the light tube 108. An angled plastic mirror 124 at the distal end of the light tube 108 redirects the laser light though a hole 126 in the tube. Overlying hole 126 is a defractive optical element 128 (DOE). In a preferred embodiment, the DOE 128 is square shaped such that the laser light exits the DOE 128 in two perpendicular lines, forming a cross-hairs on the laser target. To adjust the laser emitter 96 laterally, the light tube 108 is rotated about its longitudinal axis. To accomplish this, a lateral adjustment knob 130 turns a gear 132 coupled to a complementary gear 134 associated with the proximal end of the light tube 108. In a preferred embodiment, the laser reticle 18 is equipped with an internal power source to power the laser and the LED indicators 94. According to one embodiment, the internal power source is a disposable battery 136.

Having described the various components of the surgical trajectory monitoring system 10, exemplary methods for utilizing the system 10 during surgery will now be described. By way of example, the system 10 is described herein for use in guided formation of one or more pedicle screw pilot holes for safe and reproducible pedicle screw implantation. It will be appreciated however, that the surgical trajectory monitoring system 10 may be used during any of a number of surgical procedures without deviating from the scope of this invention. In accordance with a first general aspect of the present invention, the surgical trajectory monitoring system may be used to orient and maintain surgical instrument 14 along a desired trajectory, for example, during pilot hole formation. The distal end of surgical instrument 14 may first be placed on the pedicle target site in the zero-angle position. The instrument 14 is rotated to the desired reference position, preferably with the longitudinal axis 26 of sensor clip 12 in line with the longitudinal axis of the spine. The surgical instrument 14 may then be angulated in the sagittal plane until the desired cranial-caudal angle is reached. Maintaining the proper cranial-caudal angle, the surgical instrument 14 may then be angulated in the transverse plane until the proper medial-lateral angle is attained. Control unit 16 and/or secondary feedback system 52 will indicate to the user when the instrument 14 is aligned with the desired angles. Once the angular orientation of the instrument is correct, the instrument 14 may be advanced into the pedicle to form the pilot hole. The instrument 14 may be rotated back and forth to assist in the formation of the pilot hole. To keep the proper trajectory throughout formation, the instrument 14 may occasionally be realigned with the longitudinal axis 26 of the sensor clip 26 in line with the long axis of the spine and the angle measurements rechecked. This may be repeated until the pilot hole is complete.

To form a pilot hole in a vertebral pedicle with the aid of the surgical trajectory system 10, the surgical instrument 14 is advanced to the pedicle target site where the pilot hole is to be formed. This may be done through any of open, mini-open, or percutaneous access. The precise starting point for pilot hole formation may be chosen by the practitioner based upon their individual skill, preferences, and experience. Methods for determining a starting point with the aid of surgical trajectory system 10 are described below.

Figure 20:
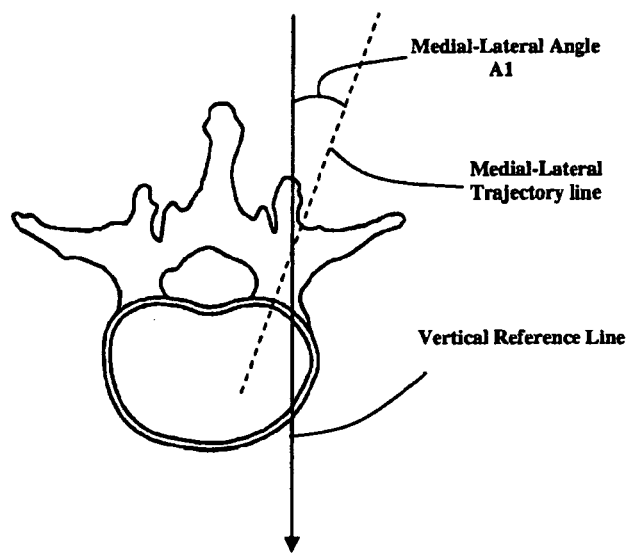
FIG. 20 is a top view of a vertebral body showing the medial-lateral angle A1 of the pedicle axis.
Figure 21:
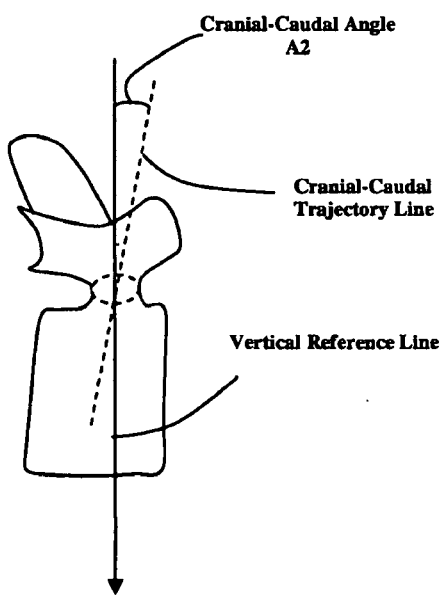
FIG. 21 is a side view of a vertebral body showing the cranial-caudal angle A2 of the pedicle axis.
Figure 22:
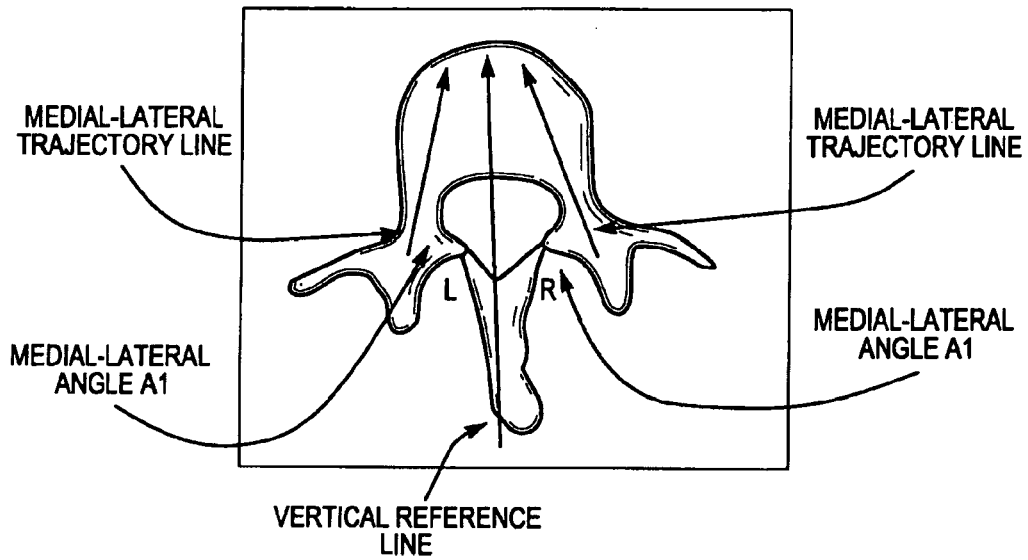
FIG. 22 illustrates a superior view preoperative MRI image used to determine the proper medial-lateral angle for hole formation, according to one embodiment of the present invention.
Figure 23:
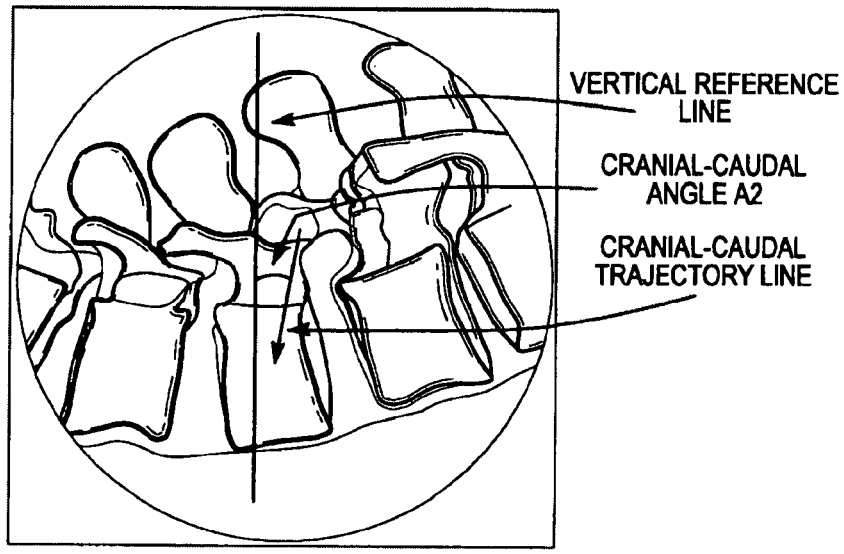
FIG. 23 illustrates an intraoperative lateral fluoroscopy image used to determine the proper cranial-caudal angle for hole formation, according to one embodiment of the present invention.

Upon safely reaching the pedicle target site, the surgical instrument 14 is manipulated into the desired angular trajectory. By way of example the pedicle axis, defined by a medial-lateral angle A1 (illustrated in FIG. 20) and a cranial-caudal angle A2 (illustrated in FIG. 21), may be determined and the pedicle screw and/or related instruments may be advanced through the pedicle along the desired trajectory. FIGS. 22-23 illustrate one exemplary method for manually determining the desired trajectory angles, wherein a series of measurements are used to determine the pedicle axis of the pedicle (or more likely, pedicles) which will receive a pedicle screw. As shown in FIG. 22, preoperative superior view MRI or CAT scan images are obtained and used to determine the medial-lateral angle A1. A vertical reference line is drawn through the center of the vertebral body (in the A-P plane). A medial-lateral trajectory line is then drawn from a central position in the pedicle (e.g. a position within the soft cancellous bone, as opposed to the harder cortical bone forming the outer perimeter of the pedicle) to an anterior point of the vertebral body for the target pedicle. The resulting angle between the medial-lateral trajectory line and the reference line is measured and the result correlates to the medial-lateral angle A1 of the pedicle axis of the target pedicle, and thus also the medial-lateral angle to be used in forming the pilot hole. The measurement is repeated for each pedicle and the results may be noted and brought to the operating room for reference during the surgery. Preferably the angles may be input into control unit 16 of system 10 during, as will be described below, for easy retrieval and application later.

As shown in FIG. 23, the cranial-caudal angle A2 may be determined using an intraoperative lateral fluoroscopy image from C-arm 20. A vertical reference line is preferably captured in the lateral fluoroscopy image to ensure measurements are performed with respect to the direction of gravity. In a preferred embodiment, this is accomplished through the use of laser reticle 18. The vertical reference line is important as the fluoroscopy image outputs can generally be rotated 360° such that the image can appear on the monitor in any orientation and a vertical reference line prevents measurements from inadvertently being calculated from an incorrect reference position.

Once the desired trajectory angles are determined for the necessary pedicles, pilot holes may be formed and screws inserted using the tilt sensor 12 to ensure the instruments and implants are aligned with the determined angles. As mentioned above, the safety and reproducibility of pilot hole formation may be further enhanced by employing neurophysiologic monitoring, as will be described in detail below, in conjunction with the trajectory monitoring performed by the surgical trajectory system 10.

Without limiting the scope of the present invention, specific examples will be described for determining the axis of a vertebral pedicle, or in other words, the angles A1 and A2 described above and for directing pedicle pilot hole formation along the pedicle axis, utilizing various features of the trajectory monitoring system 10. It will be appreciated that various other methods may be utilized to carryout guided pedicle screw pilot hole formation in accordance with the various components of the present invention. By way of example only, various features, components, methods and/or techniques that may be used with the surgical trajectory monitoring system 10 are shown and described within the PCT Patent App. No. PCT/2007/011962, entitled "Surgical Trajectory Monitoring System and Related Methods," filed May 17, 2007, the entire contents of which are hereby incorporated by reference as if set forth fully herein.

Figure 24:
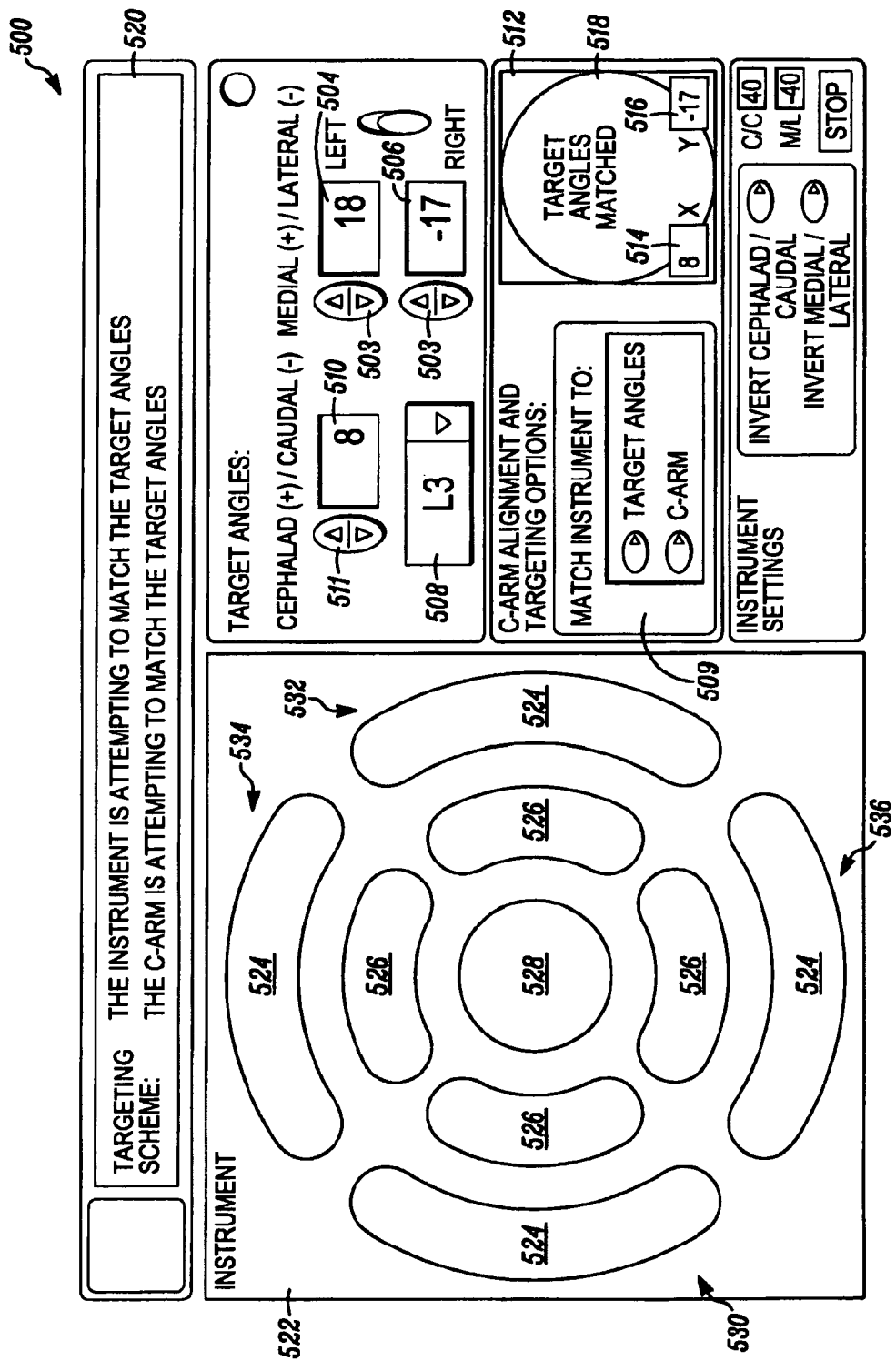
FIG. 24 is an exemplary screen display of the surgical trajectory system 10 incorporating both alpha-numeric and graphical indicia, according to one embodiment of the present invention.
Figure 25:
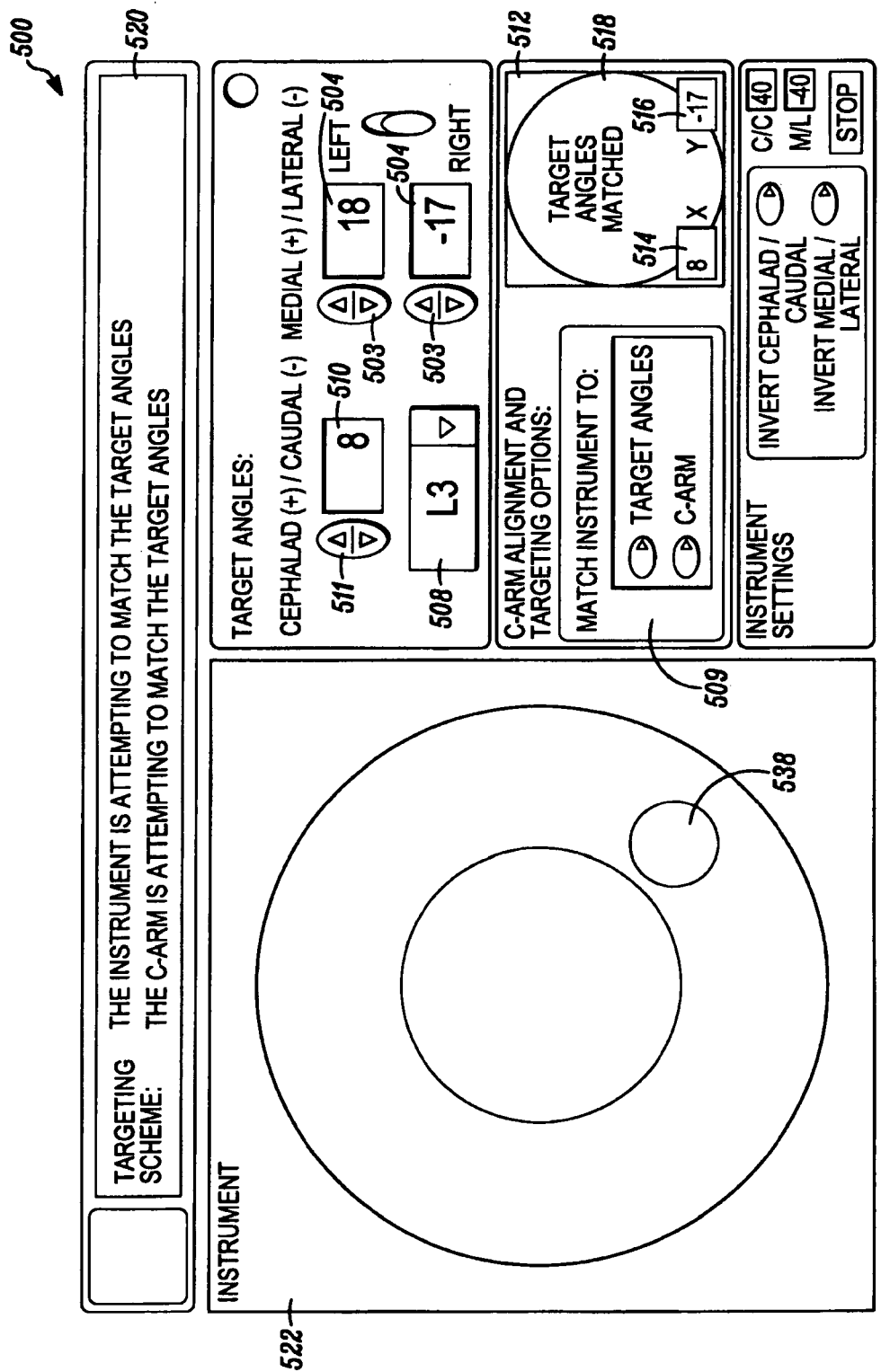
FIG. 25 is an exemplary screen display of the surgical trajectory system 10 incorporating both alpha-numeric and graphical indicia, according to another embodiment of the present invention.

FIGS. 24-25 illustrate, by way of an example only, one embodiment of screen display 500 of control unit 16 capable of receiving input from a user in addition to communicating feedback information to the user. The screen display 500 incorporates both alpha-numeric and color indicia as described above. In this example (though it is not a necessity) a graphical user interface (GUI) is utilized to enter data directly from the screen display. In a surgical procedure of pedicle screw placement, for example, it is advantageous to determine and record the medial-lateral (A1) and cranial-caudal (A2) angle of each pedicle at the different levels of the spinal, i.e. A1 and A2 of L1, A1 and A2 of L2, etc. The GUI of display 500 allows the user to enter the predetermined A1 and A2 angles of each spinal level and save this information into surgical system 10. By saving such information, the system 10 may advantageously recall the predetermined angles (A1 and A2) for each spinal level at any given time. It is appreciated that the current integrated control system may also be utilized to determine the pedicle access angles (A1 and A2). This process is described below. It is also appreciated that in addition to its uses in pedicle screw placement, the current embodiment may be suitable for use in any number of additional surgical procedures where the angular orientation or trajectory of instrumentation and/or implants and/or instrumentation is important, including but not limited to general (non-spine) orthopedics and non-pedicular based spine procedures With reference to FIGS. 24-25, measurements obtained for a pre-defined medial-lateral (M-L) angle A1 may be entered into input boxes 504 and 506 for (for left and right pedicles, respectively). Multiple adjustment buttons may be used to set the pre-defined angles. FIG. 24 illustrates a method, by way of example only, of adjusting the left and right M-L angles A1 by using the angle adjustment button sets 503. FIG. 25 illustrates another method, by way of example only, of increasing or decreasing the M-L angles in increments of 10° using the angle adjustment buttons 505 labeled (by way of example only) "+10" and "−10". More precise angle adjustments may be made by increasing or decreasing the pre-defined angle in increments of 1° using the angle adjustment buttons 507 labeled (by way of example only) "+1" and "−1". Measurements obtained for the cranial-caudal (C-C) angle A2 may also be entered into input box 510 and adjusted using the angle adjustment button set 511. Level selection menu 508 allows the user to input the predetermined angle A1 and A2 for each spinal level. The entered values may be saved by the system such that during the procedure selecting the spinal level from level selection menu 508 automatically recalls the inputted values.

Control unit 16 display screen 500 may provide feedback information from multiple tilt sensors 12 associated with different devices (e.g. instruments 14, C-arm 20, laser reticle 18, etc. . . . ). By displaying feedback information from multiple devices, the information may be used in conjunction with each other to assist a surgeon in safely performing complicated surgical procedures (e.g. pedicle screw implantation, etc. . . . ). It is appreciated that further advantages may be gained by combining the tilt sensor data with other relevant data (e.g. neurophysiologic monitoring data, fluoroscopic images, etc. . . . ) to provide an integrated system and/or methods for assisting in the performance of the surgical procedure. With reference to FIGS. 24-25, display screen 500 provides a C-arm angle window 512 containing data pertaining to a second tilt sensor 12 positioned on a fluoroscopic imager. By way of example, numeral boxes 514 and 516 display the numeric values of the medial-lateral and the cranial-caudal angles as determined by the C-arm tilt sensor 12. Numeric values 514 and 516 may be referenced by the user to help match the M-L and C-C values corresponding to the C-arm sensor within an accepted range of the pre-defined target angles A1 and A2 for each spinal level. If the C-arm is aligned with the pedicle axis (placed in the owls eye view) the C-arm values A1($c$) and A2($c$), indicated in windows 514 and 516, should approximate the pedicle axis angles A1 and A2. In another example, the C-arm window 512, or a portion there of (such as the circle 518) may be saturated with the color green when the numeric values corresponding to the C-arm sensor matches within an accepted range of the predetermined target angles.

Display screen 500 may also provide feedback information from another tilt sensor 12 coupled with surgical instrument 14. With reference to FIGS. 24-25, by way of example only, the angular orientation of instrument 14 may be communicated to the user in the instrument window 522. Instrument window 522 may employ different embodiments to assist the user in matching the angular orientation of the instrument 14 to the predefined target angles for each level. With reference to FIG. 24, the control system display 500 employs a color coded target to provide feedback information of the angular orientation of surgical instrument 14. The outer rings 524 of the target may be red, the middle rings 526 of the target may be yellow, and the inner circle 528 may be green. When the instrument is aligned with the predetermined target angles, the center circle may be saturated green, indicating that both the medial-lateral angle A1 and cranial-caudal angle A2 have been matched, or A1=A1($i$) and A2=A2($i$). If the user wishes to match the angular orientation of the instrument 14 to the angular orientation of the C-arm, the user may make that selection in the "match instrument to" window 509. When instrument 14 is matched to the C-arm (A1($c$)=A1($i$) and A2($c$)=A2($i$)) the center circle 528 may be saturated green. The middle 526 and outer 524 rings may be divided into quadrants 530, 532, 534, and 536 corresponding to right, left, cranial, and caudal, respectively. By way of example, if the instrument is aligned too far left of the target, the outer 524 or middle 526 ring in the left quadrant 530 will be saturated depending upon how misaligned the instrument is (i.e. whether it falls into the yellow or red range). Similarly, if the instrument is aligned too far cranially, the outer 524 or middle 526 ring in the upper quadrant 534 will be saturated depending upon how misaligned the instrument is. If the instrument has matched one of the targeted angles but not the other, only the quadrant corresponding to the misaligned angle will be saturated.

In another embodiment of instrument window 522, FIG. 25 employs a color coded display, approximating the look of a bubble level, to provide feedback of the angular orientation of the surgical instrument 14. A free floating ring 538 moves relative to the movement of the instrument. The closer the bubble is to the center, the closer the instrument is to matching the target angle. When the instrument is within the range indicating proper alignment, the ring 538 may be saturated green. Similar to the embodiment of FIG. 30, the user may also have the option to match the angular orientation of the instrument 14 to the C-arm sensor values, rather than the predetermined target values. This option may be exercised, by way of example only, by selecting the appropriate button in the "match instrument to" window 509. A status bar 520 may be provided to indicate the relative status of both the instrument 14 and C-arm tilt sensors. By way of example only, the status bar 520 depicted in FIGS. 24 and 25 indicate that both the instrument 14 and the C-arm sensors are attempting to match the targeted angles. Other messages (not shown) may indicate for example, that the instrument 12, 80 is trying to target the C-arm angles, that the target angles are matched, or that a sensor is not in use.

Figure 26:
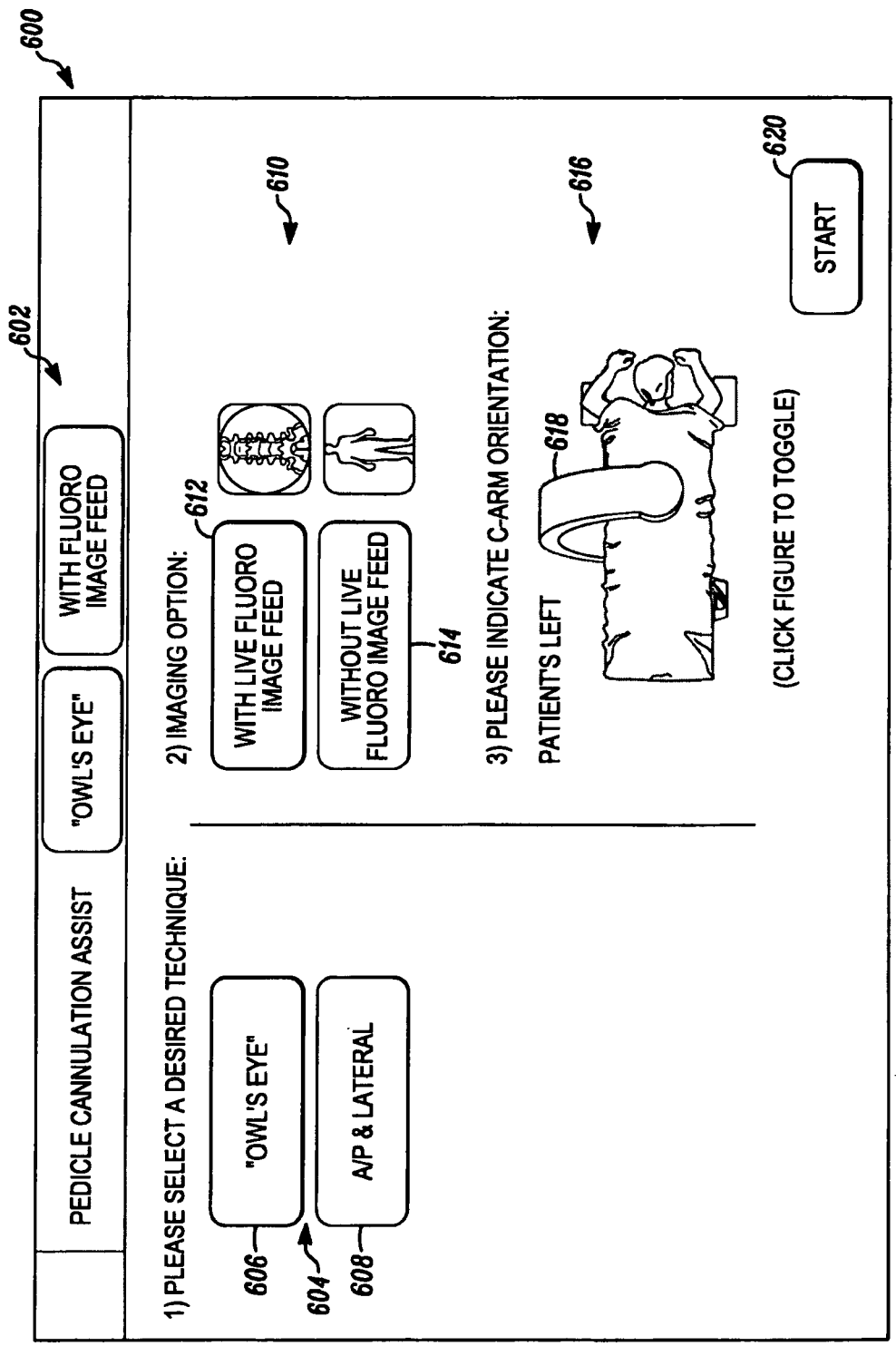
FIGS. 26-36 are exemplary screen displays of the surgical trajectory system 10 incorporating alpha-numeric, graphical indicia, and fluoroscopic image data, and various control features according to another embodiment of the present invention.

FIGS. 26-36 illustrate, by way of example only, another embodiment of screen display 600 of an integrated control unit 16. FIGS. 26-36 illustrate multiple screen displays of an example embodiment of a "Pedicle Cannulation Assist" (PCA) program designed to integrate data from multiple sources. The PCA program may be utilized with an embodiment of the feedback device 16 comprising a computer or similar type processing unit (not shown) capable of receiving input from a user as well as communicating feedback to the user. In similar fashion to the display screen 500, this example utilizes (though it is not necessary) a graphical user interface (GUI) to enter data directly on the screen displays. The exemplary screen display 600 represents a setup screen from which the user may select the desired technique (e.g. "owls eye" or "A/P& Lateral"—described below) to be performed, as well as various configurations utilized within the technique (e.g. integration of live fluoroscopic images, orientation of the C-arm, etc. . . . ). Screen display 600 includes a header 602 that identifies the program and indicates the current configuration as selected by the user (e.g. Owls eye technique with integrated live fluoroscopy as depicted in FIG. 26). Buttons in the technique field 604 may be used to select the desired technique to be applied. By way of example, the "Owl's Eye" button 606 may be touched to select the Owls Eye technique (described below) and the "A/P & Lateral button" may be touched to select the A/P & Lateral technique. In the imaging field 610, buttons 612 and 614 may be touched to select between the options of integrating live fluoroscopic images or proceeding without integrated images, respectively. In the orientation field 616, the user may set the orientation of the C-arm (i.e. whether the C-arm is positioned on the right or left side of the patient) that is to be utilized during the procedure. By way of example, the user may simply touch the C-arm depiction 618 to toggle from one orientation option to the next. The start button 620 locks in the selected configuration and advances the program.

Figure 27:
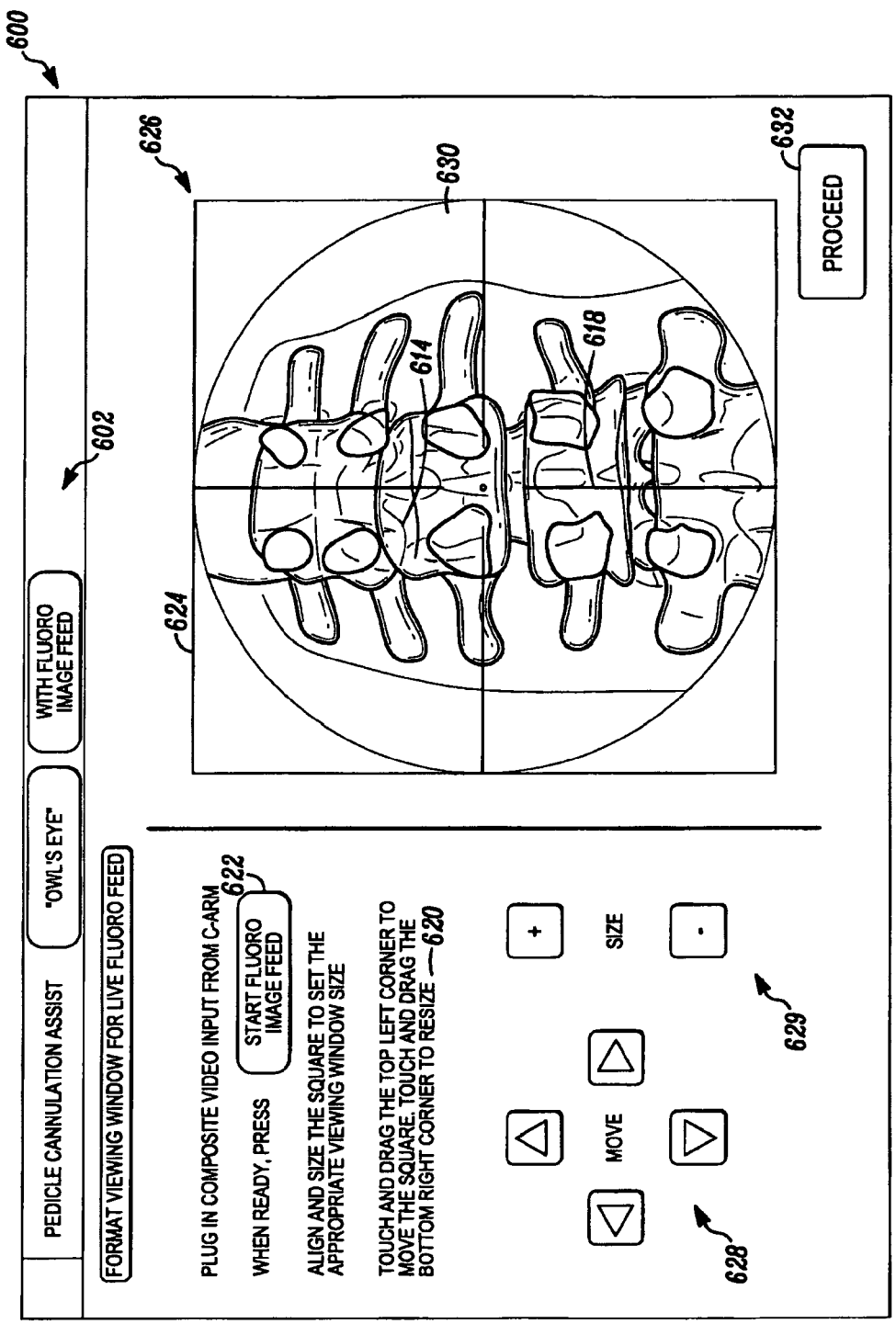

In this embodiment, the feedback device 16 utilizes an image capture system (not shown) preferably incorporated within the hardware and/or software in order to retrieve images from the C-arm. When the live fluoroscopic image option is selected display screen 600 may be advance to a format viewing window to format the image (if necessary), as shown in FIG. 27. The instruction field 620 provides instructions for formatting the image into the appropriate size and/or alignment. Upon selecting the image feed button 622, the fluoroscopic image 630 is retrieved and displayed in the viewing window 624 located in the image field 626. As indicated by the instructions in the instruction field 620, the image may be resized by, for example only, touching and dragging the bottom right corner of the viewing window 624. The image may be aligned by touching (by way of example only) the top left corner of the viewing window 624 and dragging it until the image is aligned. Button sets 628 and 629 may be provided and utilized as alternative ways to align and resize the image 630, respectively. The proceed button 632 locks in the viewing window 624 formatting and advances the program.

Figure 28:
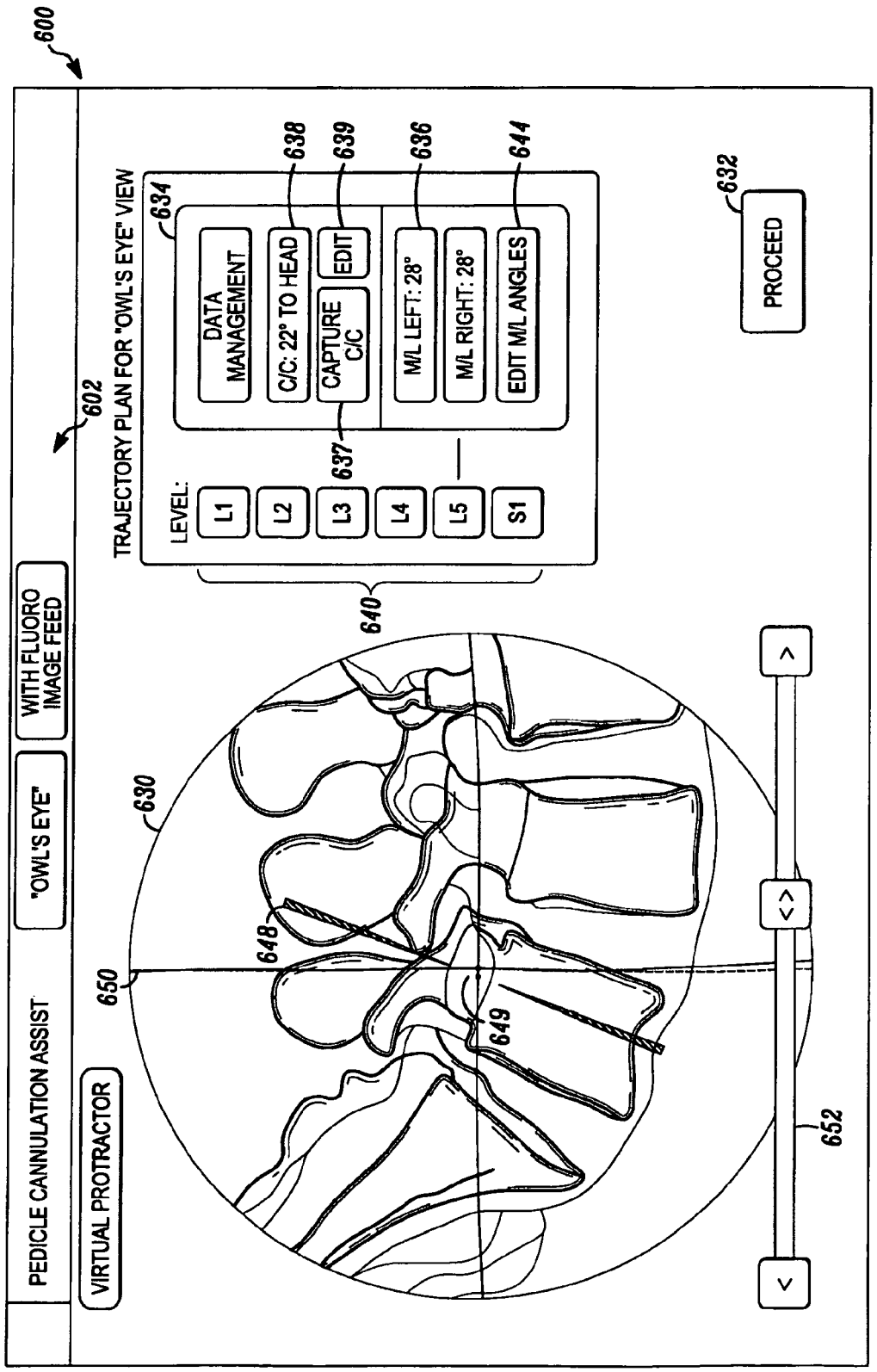
Figure 29:
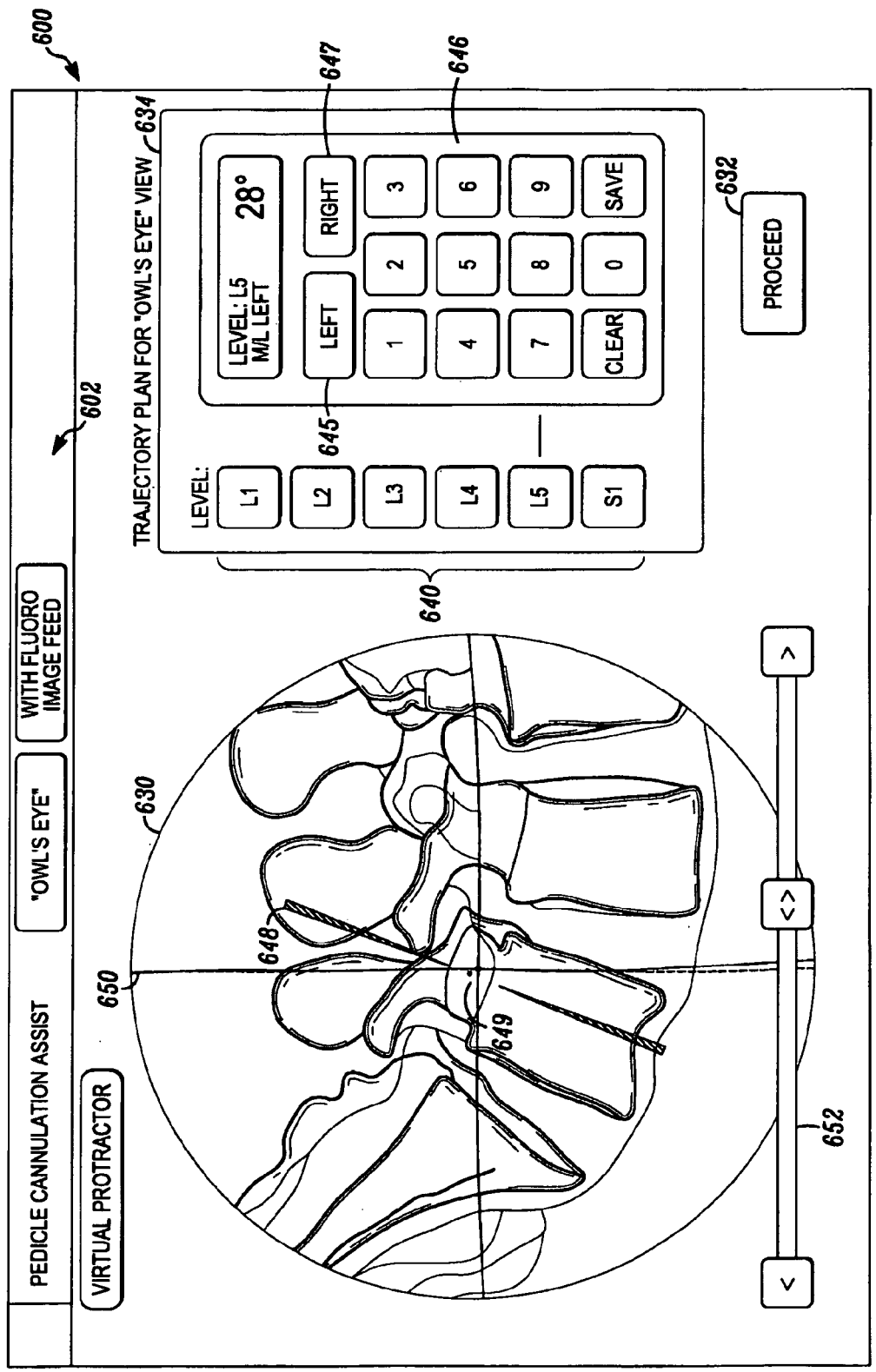
Figure 30:
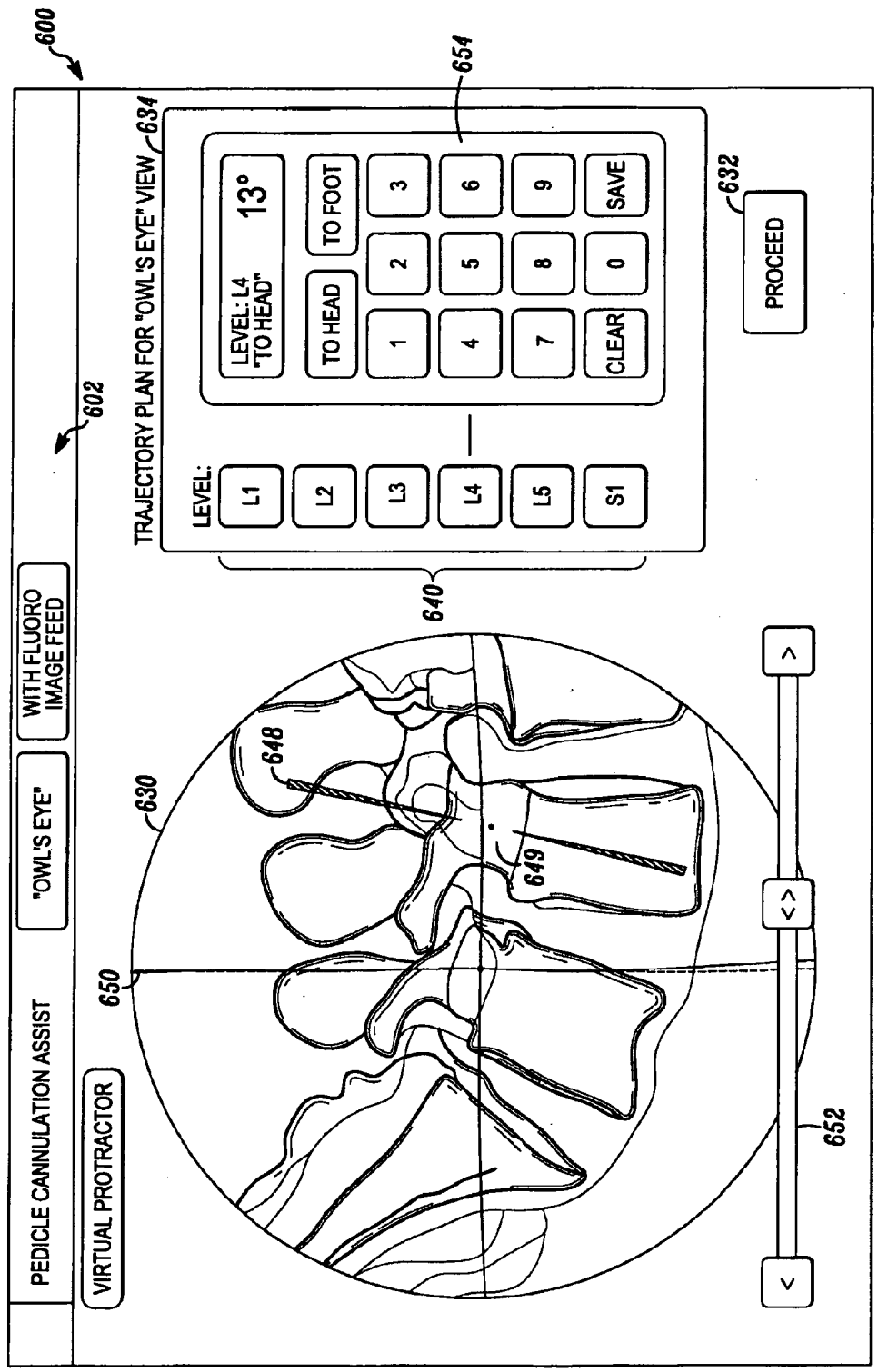
Figure 31:
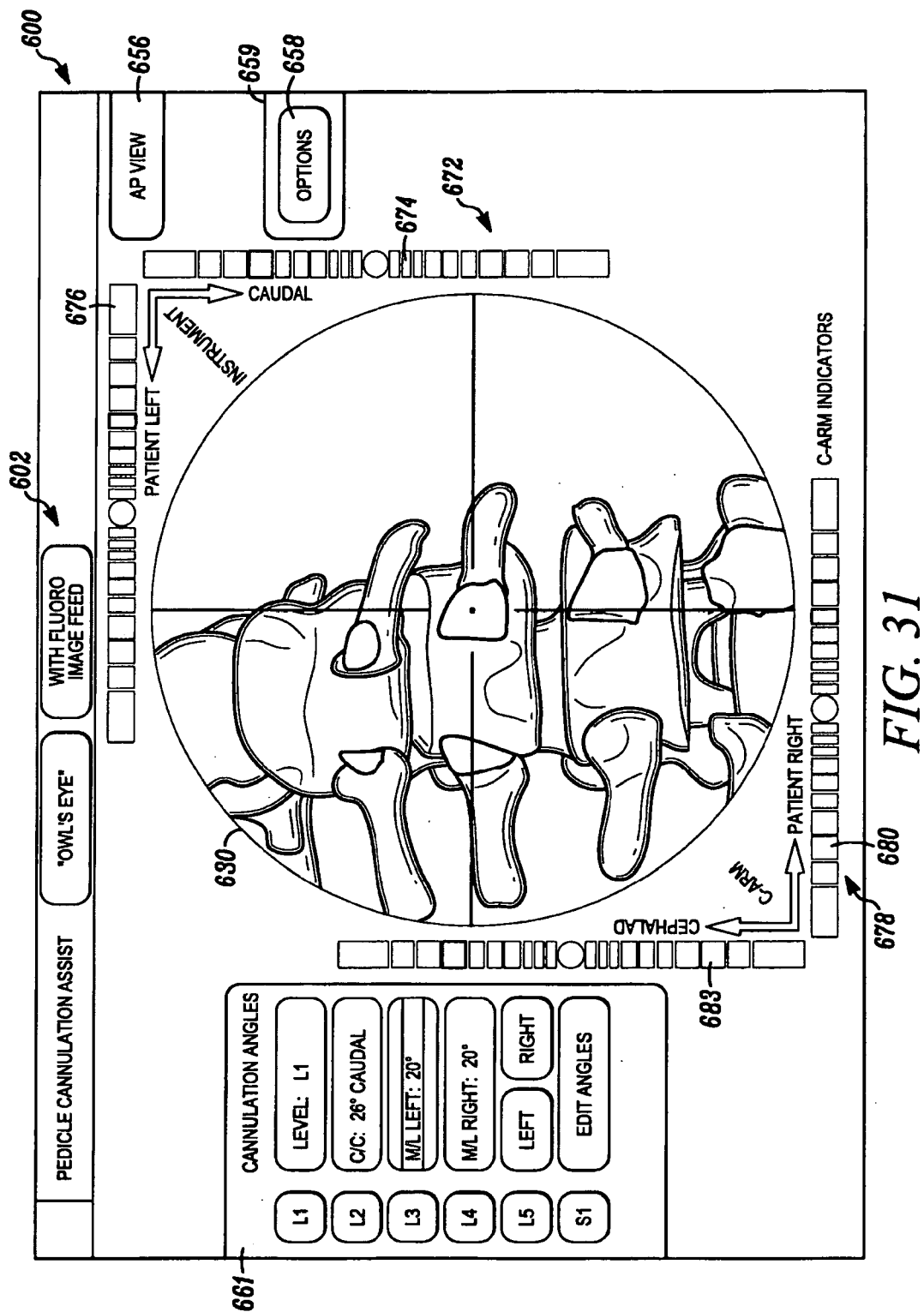
Figure 32:
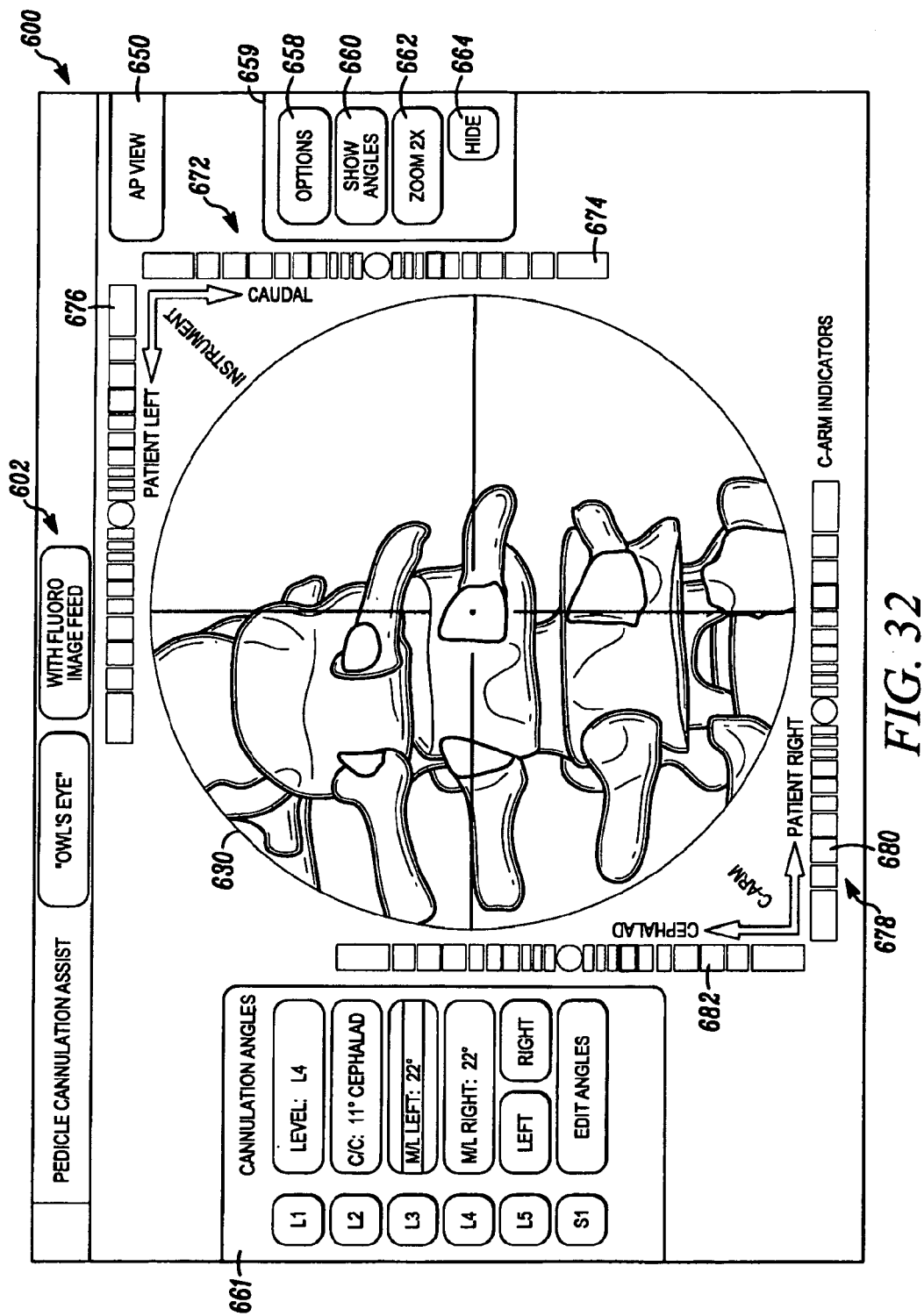

A "virtual protractor" display screen is illustrated in FIGS. 28-30. The virtual protractor screen may be utilized to input and/or determine the angles to be used during pilot hole formation (i.e. the cranial-caudal and medial-lateral angles discussed elsewhere herein). Data management field 634 may be used to view and input angle data in the integrated screen. The data management field includes an M/L window 636, a C/C window 638, and spinal level buttons 640. Spinal level buttons 640 may be used to select and indicate the spinal level which corresponds to the data being input or displayed in the M/L and C/C windows 636 and 638 (e.g. level L5 in FIGS. 28 and 29, level L4 in FIG. 30). As previously described, the medial-lateral angles for each pedicle to be instrumented are preferably determined preoperatively. The data may be taken to the OR and entered using the M/L window 636. To enter the data, the proper spinal level is selected and the edit M/L angles button 644 is selected. As shown in FIG. 29, a keypad 646 appears in the data management field 634 and the angles may be entered and saved (or cleared and reentered) for the left and right pedicles. Toggling between the left and right pedicles may be done by selecting the appropriate buttons labeled, by way of example only, "left" 645 and "right" 647. This may be done in turn for each applicable pedicle. Alternatively, the data may be input into the system prior to surgery or entered onto an external memory device (e.g. memory cord, USB flash drive, etc. . . . ) and transferred to the system in the OR in order to reduce the overall surgical time.

Figure 37:
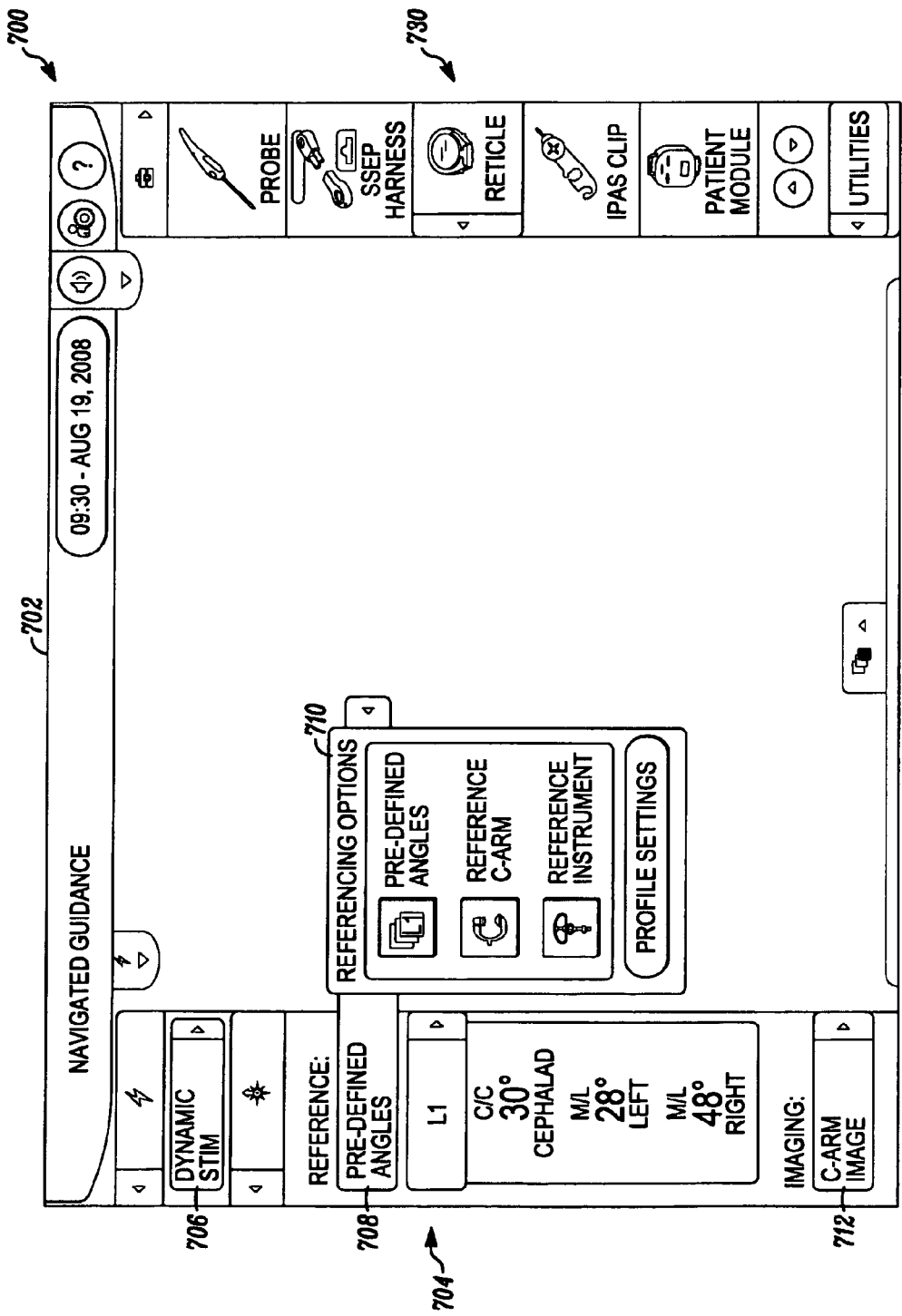
FIGS. 37-46 are exemplary screen displays of the surgical trajectory system 10 incorporating alpha-numeric, graphical indicia, and fluoroscopic image data, and various control features according to yet another embodiment of the present invention.

The cranial-caudal angles for each pedicle to be instrumented may be determined using the virtual protractor 648 superimposed on the fluoroscopic image 630. To accomplish this, the C-arm is oriented in the lateral position such that the image 630 shown on the screen is a lateral image. A zero line 650 may be rotated into alignment with the vertical reference line generated in the fluoroscopic image (as previously described) by selecting (e.g. touching) and dragging it into position. The center point 649 of the virtual protractor 648 may then be centered over the appropriate pedicle by touching the image at the desired position. The protractor 648 will then position itself, centered on the position touched. Once positioned over the center of the pedicle, the virtual protractor may be rotated using the control bar 652 until it is aligned with the axis of the pedicle. Selecting the capture C/C button 637 will automatically input and save the angle into the integrated system as determined by the rotation of the virtual protractor 648 relative to the zero line 650. With reference to FIG. 37, the user may also enter the C/C angle manually by selecting the edit button 639 in the C/C window 638. After selecting the edit button 639, a C/C keypad 654 appears and the user may select the appropriate "to foot" or "to head" button to finalize the angle input for the selected level. The C/C angles may be determined and entered for each applicable spinal level. The proceed button 632 will advance the program into the appropriate technique screen.

Figure 33:
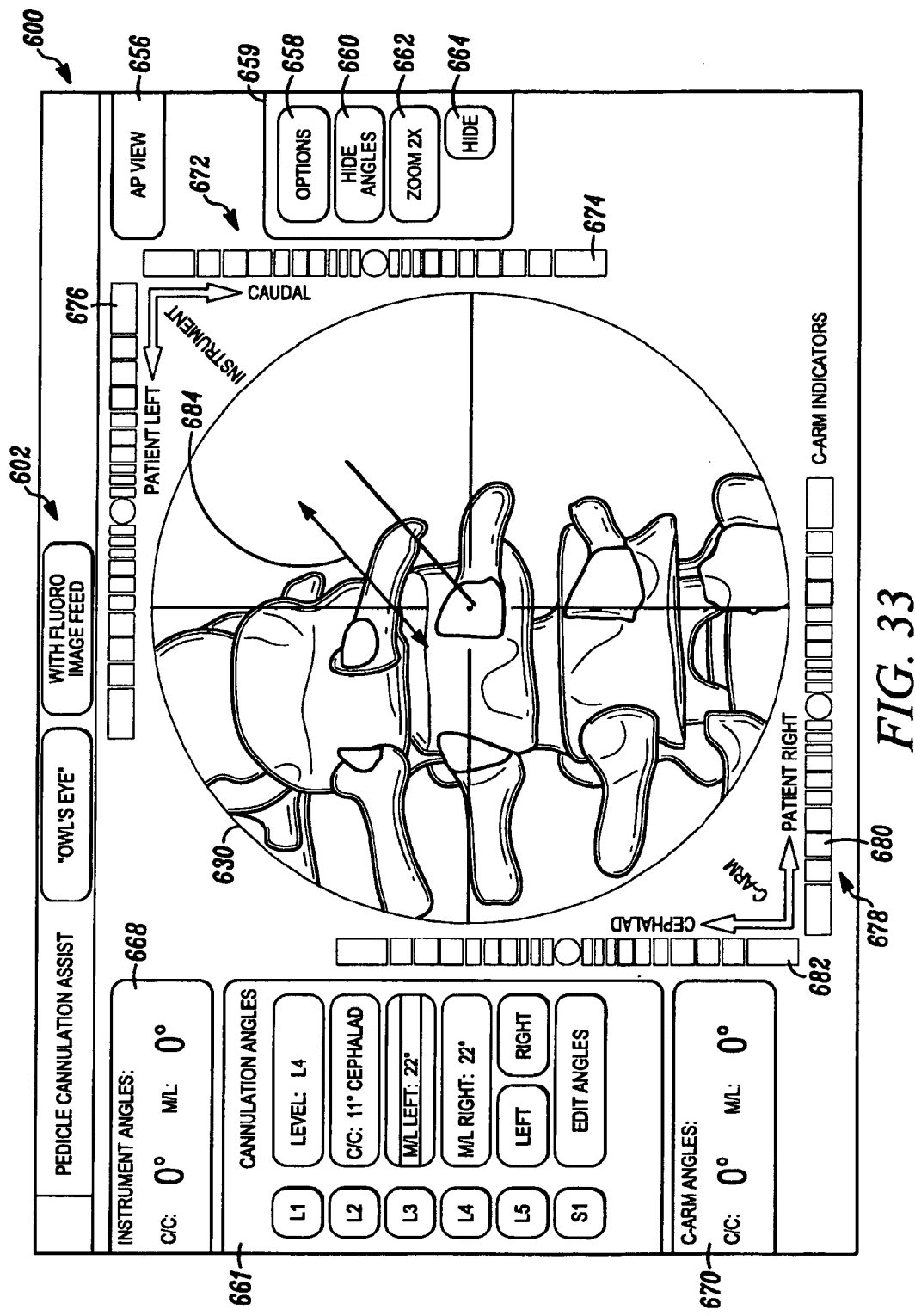
Figure 34:
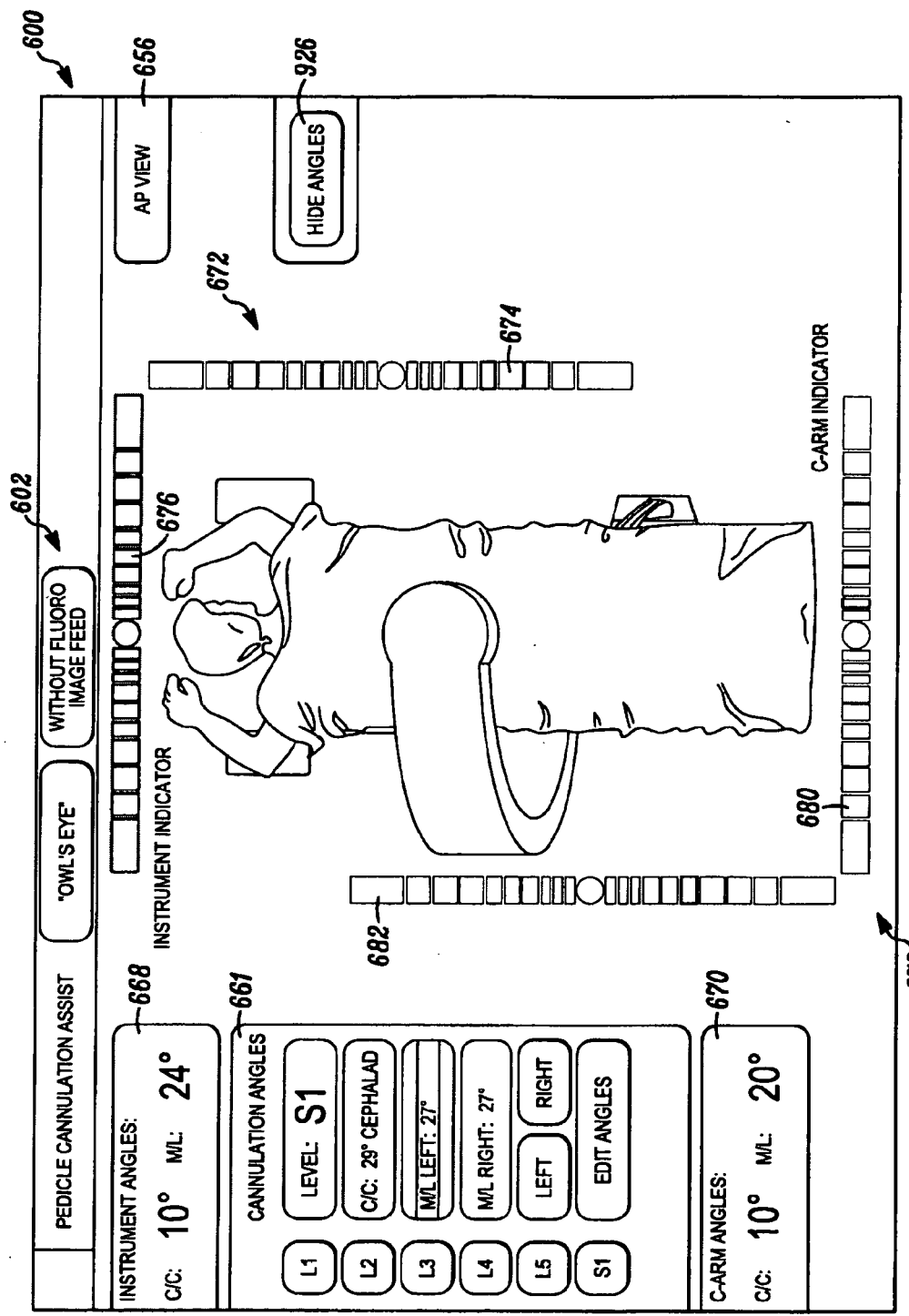
Figure 35:
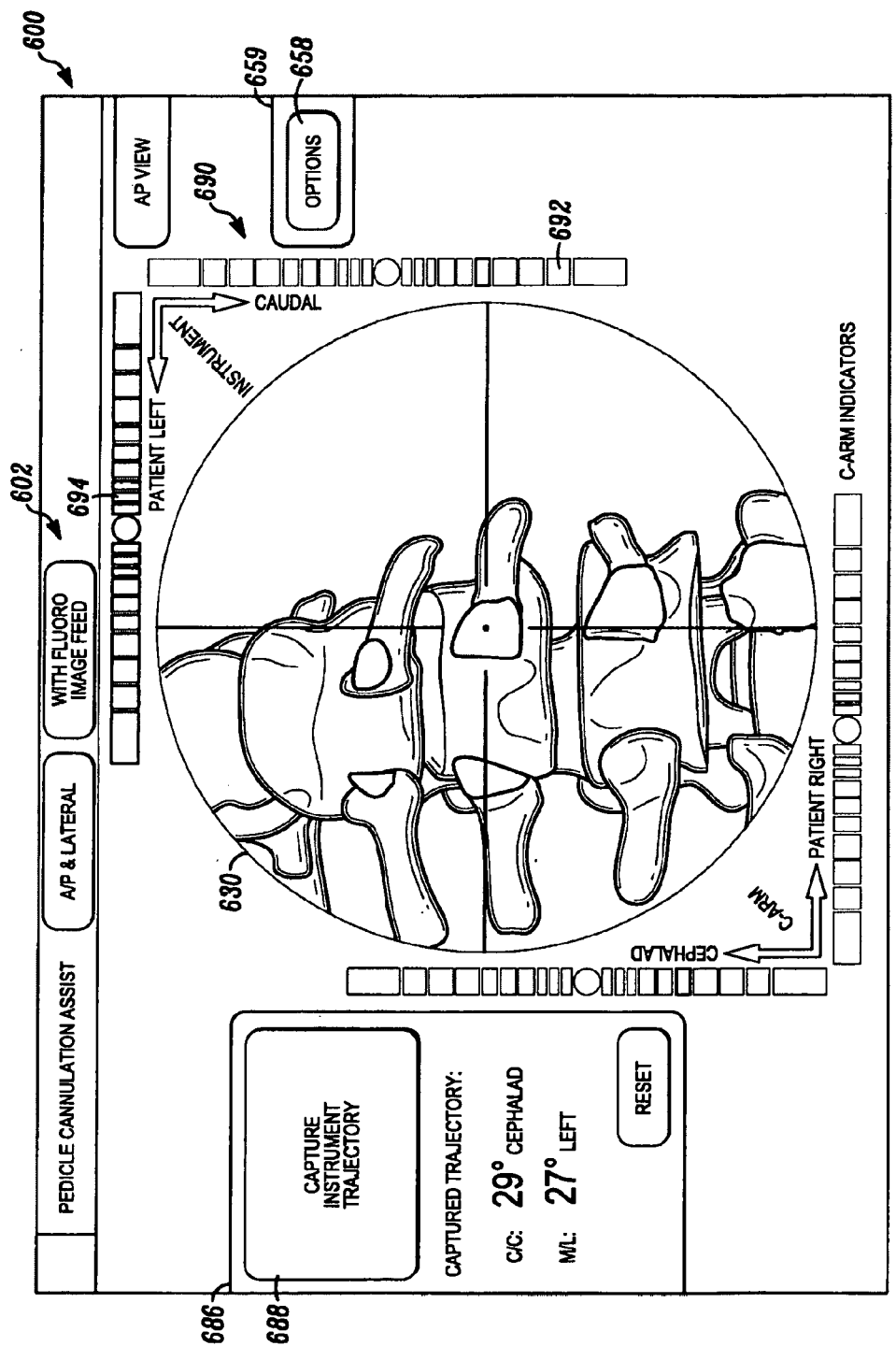
Figure 36:
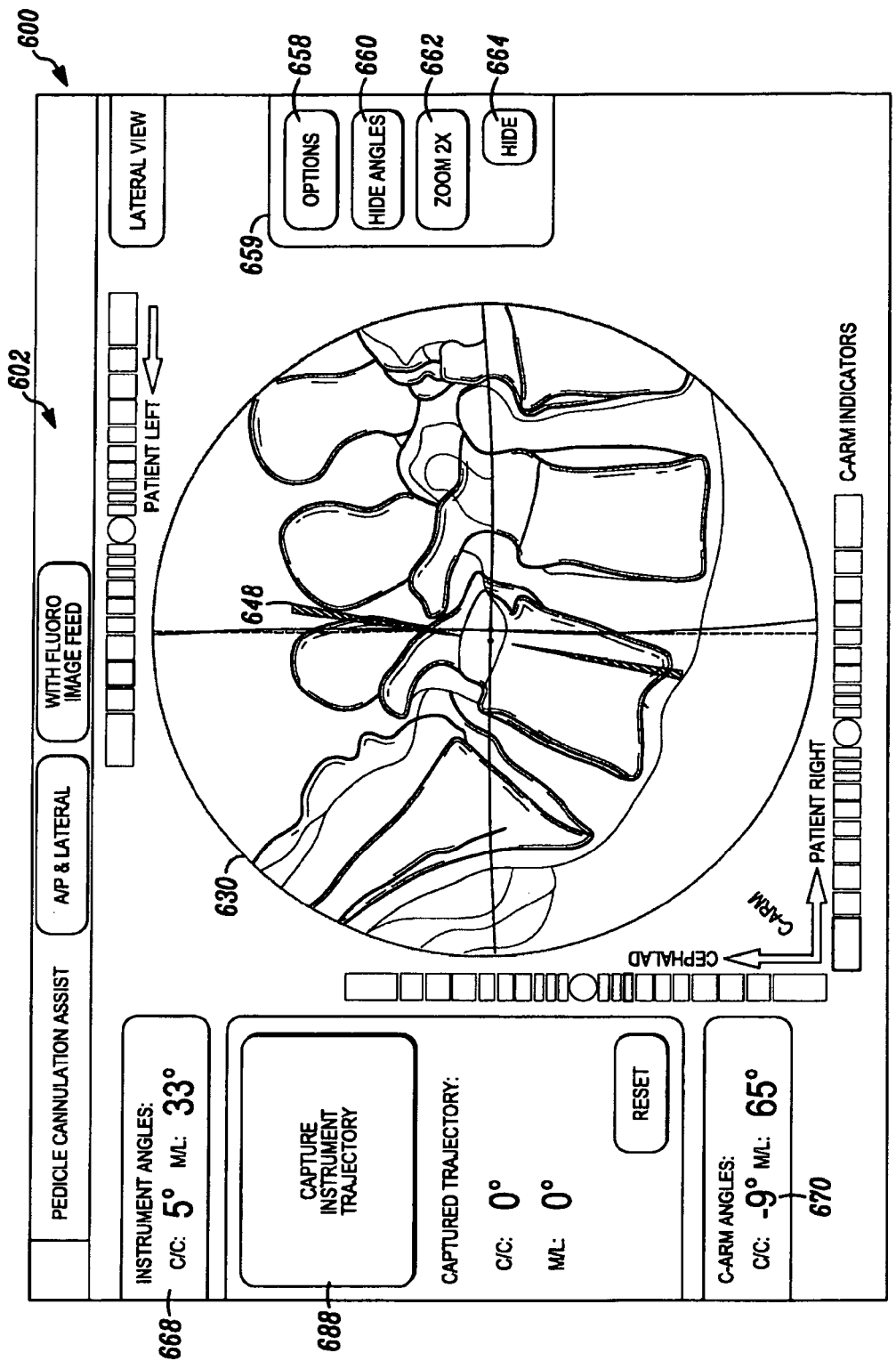

By way of example only, FIGS. 31-34 illustrate a main screen display for the owls eye technique according to one exemplary embodiment. An indicator 656 shows the relative orientation of the C-arm 20, either AP view or lateral view. The indicator 656 does not necessarily correspond to the true AP or true lateral orientations but is rather just a general indication. For example, as shown here the C-arm is oriented in the owl's eye position which is not a true AP view but is generally closer to a true AP view than a true lateral view. If the C-arm is rotated past a certain point, by way of example, 60 degrees, the indicator will change to indicate the opposite view (e.g. lateral). Selecting the option button 658 expands an option menu 659, illustrated in FIGS. 32-33, which may include but is not necessarily limited to, a show or hide angle button 660, a zoom button 662, and a hide button 664. The show or hide angle button 660 either opens or closes an instrument angle window 668 and C-arm angle window 670 (FIGS. 33 and 34). The zoom button 662 zooms in on the fluoroscopic image 630. The hide button 664 contracts the options menu 659. A data management field 661 illustrates the selected spinal level and the cranial-caudal and medial-lateral angels previously input for the selected level. The angles may be edited in the data management field 661 via controls similar to those previously described with reference to virtual protractor screen of FIGS. 28-30. Instrument and C-arm target indicators, 672 and 678 respectively, are positioned opposite each other around the fluoroscopic image 630. By way of example only, FIG. 34 illustrates the main screen display 600 for the owls eye technique when the live fluoroscopy option is not selected. The display in FIG. 34 is generally the same except that the fluoroscopic image 630 is replaced by a graphic representing the patient.

The instrument target indicator 672 includes a medial-lateral bar 676 and a cranial-caudal bar 674. Individual segments of the target indicator 672 may be colored to represent the position of the instrument and relative to the previously determined target angles (displayed in the data management window 661). The indicator bar 672 may, for example, be shown generally as neutral color (e.g. gray). A single segment on each of the medial-lateral bar 676 and cranial-caudal bar 674 may be highlighted by a color (e.g. green) to indicate the relative position instrument to the target angle. By way of example, the closer the lighted segment is to the target circle, the closer the instrument is to being aligned with the corresponding predetermined angle. The size of the individual segments may be different and correspond to the range of values encompassed by the segment. By way of example only, the larger segments situated farthest from the target circles correspond to larger ranges. In one example, set forth by way of example only, the target circle has a range of 3° such that the cranial-caudal target circle will be highlighted when the instrument is aligned within 3° of the corresponding cranial-caudal target angle and the medial-lateral target circle will be highlighted when the instrument is aligned within 3° of the predetermined medial-lateral angle. In one embodiment, the entire medial-lateral bar 676 is highlighted in the appropriate color (e.g. green) when the instrument is aligned within the range of the target circle (e.g. 3 in this example). Similarly, the entire cranial-caudal bar 674 is highlighted in the appropriate color (e.g. green) when the instrument is aligned within the range of the target circle (e.g. again 3° in this example). Thus, when the instrument is aligned within 3° of the target medial-lateral angle and 3° of the target cranial-caudal angle, the entire instrument target indicator 672 may be highlighted in the appropriate color (e.g. green in this example).

In another method, the user may also match the angular orientation of instrument 14 to a predefined angular orientation is illustrated using the "ball and stick" target indicator 684 of changing length, illustrated in FIG. 33. The length and position of the ball and stick will indicate to the user the desired orientation of surgical instrument 14 in reference to a predefined angular orientation. As illustrated in FIG. 33, one end of the stick is positioned in the center of fluoroscopic image 630 and the other end extends outwards from the center into the top-left quadrant. This illustration indicates to the user that the orientation of instrument 14 is not matched up with the predefined angular orientation. Specifically, indicator stick 684 in FIG. 33 specifies to the user that the angular orientation of instrument 14 is too far right in the M-L direction and too far towards the head of the patient in the cranial-caudal direction. By way of example only, the user will adjust instrument 14 in accordance to the position of the indicator stick. As the user adjusts the angular orientation of instrument 14 towards the desired angles, the stick indicator will shorten in length. Once the desired angular orientation is found, fluoroscopic image 630 may produce an image of a single dot at the center of the image. In another example, the entire fluoroscopic image 630, or a portion there of, may be saturated with the color green angular values corresponding to the instrument sensor matches within an accepted range of the predetermined target angles. It is appreciated that any suitable combination of the methods described, whether alone or in combination with another, may be used to indicate to the user the angular orientation of instrument 14 in reference to predefined angles.

Like the instrument target indicator 672, the C-arm target indicator 678 includes a medial-lateral bar 680 and a cranial-caudal bar 924. Individual segments of the target indicator 678 may be colored to represent the orientation of the C-arm relative to the previously determined target angles (displayed in the data management window 661). The C-arm target indicator 678 may, for example, be shown generally as neutral color (e.g. gray). A single segment on each of the medial-lateral bar 680 and cranial-caudal bar 682 may be highlighted by a color (e.g. purple) to indicate the relative position C-arm to the target angles. By way of example, the closer the lighted segment is to the target circle, the closer the C-arm is to being aligned with the corresponding predetermined angle. The size of the individual segments may be different and correspond to the range of values encompassed by the segment. By way of example only, the larger segments situated farthest from the target circles correspond to larger ranges. In one example, set forth by way of example only, the target circle has a range of 3° such that the cranial-caudal target circle will be highlighted when the C-arm is aligned within 3° of the corresponding cranial-caudal target angle and the medial-lateral target circle will be highlighted when the C-arm is aligned within 3° of the predetermined target medial-lateral angle. In one embodiment, the entire medial-lateral bar 680 is highlighted in the appropriate color (e.g. purple) when the C-arm is aligned within the range of the target circle (e.g. 3 in this example). Similarly, the entire cranial-caudal bar 682 is highlighted in the appropriate color (e.g. purple) when the instrument is aligned within the range of the target circle (e.g. again 3° in this example). Thus, when the instrument is aligned within 3° of the target medial-lateral angle and 3° of the target cranial-caudal angle, the C-arm target indicator 678 may be highlighted in the appropriate color (e.g. purple in this example).

In use, the C-arm is easily oriented into the owls eye position using the C-arm target indicator 678 as a guide. Again, when the owls eye position is reached, both the medial-later bar 680 and cranial-caudal bar 682 will fully highlighted in the appropriate color (e.g. purple). Once the C-arm is in the owls eye position, the starting point for instrument insertion may be determined according to the owls eye method for starting point determination previously described above. If the live fluoroscopy option is not chosen, the starting point may be determined using the fluoroscopic image monitor 216 as previously described. When the instrument is positioned on the desired starting point, the instrument may be aligned with the pedicle axis by adjusting the instrument until both the medial-lateral indicator bar 676 and the cranial-caudal indicator bar 674 of the instrument target indicator are fully highlighted, indicating that the instrument is aligned with the target angles which preferably correspond to the pedicle axis. When the target indicator 672 shows correct alignment, the instrument may be advanced into and through the pedicle into the vertebral body. The process may be repeated for each pedicle to be instrumented.

Figure 41:
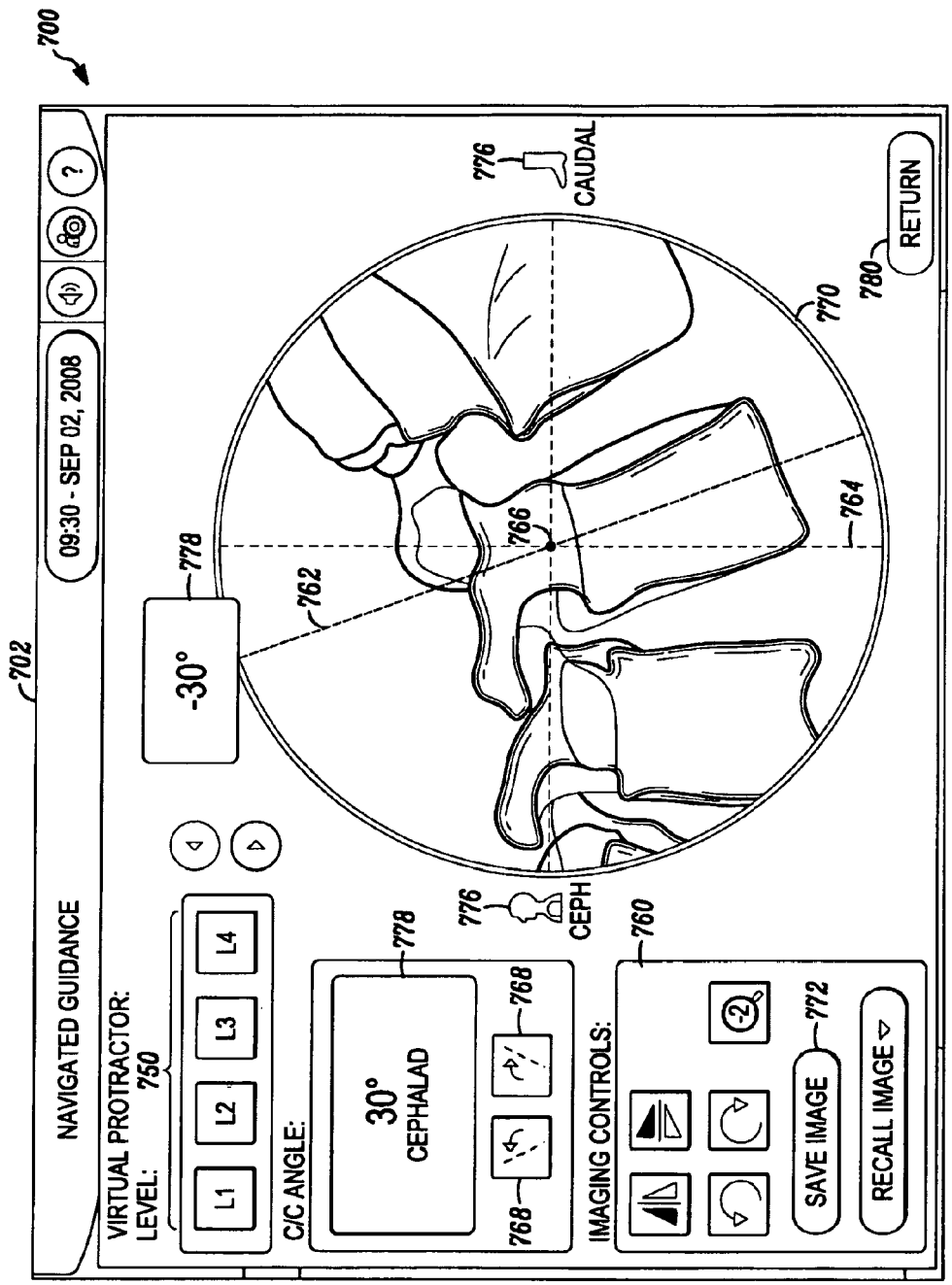
Figure 42:
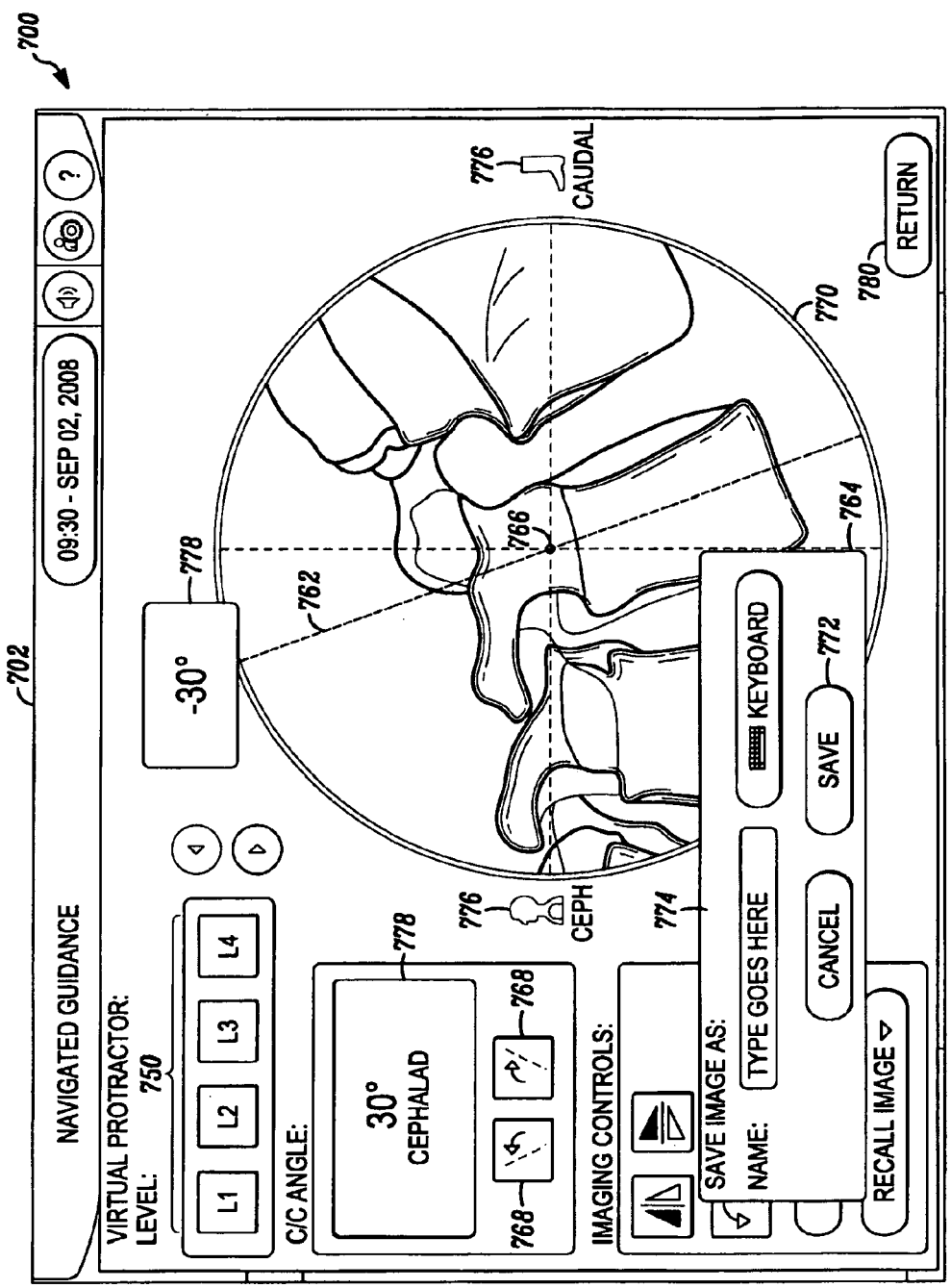

With reference now to FIGS. 41-42, there is shown, by way of example only, main screens display for the A/P & lateral technique option, respectively. The A/P & lateral technique main display is generally similar to the owls eye main display above. The A/P & lateral technique does not utilize predetermined target angles and thus the data management field from the owl's eye main display is replaced with a data capture window 686. Selecting the capture instrument trajectory button 688 locks in the medial-lateral and cranial-caudal angles associated with the position of the instrument when the button is selected. Thereafter, the instrument target indicator 690 functions as described above with the "captured" angles filling the role of the predetermined target angles. Thus, the surgeon is free to determine a desired trajectory through any desired means. The instrument target indicator 690 will assist the surgeon in maintaining the selected trajectory thereafter. If the C-arm is rotated into the lateral orientation, as depicted in FIG. 42, the cranial-caudal bar 692 of the instrument indicator 690 disappears and a protractor 648 is superimposed on the fluoroscopic image 630. The cranial-caudal orientation of the instrument is thereafter depicted via rotation of the protractor 648.

One example method for using the exemplary A/P & lateral main display uses predetermined medial-lateral angles as described previously. The M/L angles are recorded prior to surgery and brought to the OR for reference. The C-arm may be oriented in the lateral view position and the protractor 648 aligned with the axis of the pedicle. In this position the instrument is aligned in the proper cranial-caudal position. Maintaining the cranial-caudal position, the instrument may be adjusted until the instrument angle window 668 indicates that the instrument is aligned with the predetermined medial-lateral angle. Once in this position the capture instrument trajectory button 688 may be selected. Thereafter, the instrument may be advanced into and through the pedicle using the instrument target indicator 690 to maintain the trajectory. This may be repeated for each pedicle to be instrumented.

FIGS. 37-46 illustrate, by way of example only, yet another embodiment of screen display 700 of an display screen system capable of receiving input from a user in addition to communication feedback from multiple sources (e.g. instrument 15, laser reticle 18, C-arm 20, etc). In similar fashion to the display screen 500 and 600, this example utilizes (though it is not necessary) a graphical user interface (GUI) to enter data directly on the screen displays. Screen display 700 includes a header 702 that identifies the program and indicates the current configuration as selected by the user (e.g. Navigated Guidance as illustrated in FIG. 37). Display screen 700 also consists, by way of example, test menu bar 704. From menu bar 704, the user may select and/or change multiple options of the selected configuration. Test menu bar 706, by way of example only, may open up a menu bar (not shown), from which multiple neurophysiologic test may be incorporated. In this setup screen, the user may select a pre-determined reference angle (e.g. using pre-defined angles as a reference when implementing the navigated guidance function of the current system) by pressing reference button 708 and selecting a reference option from reference menu 710. The user may also adjust the image screen of the display by selecting imaging button 712.

Figure 38:
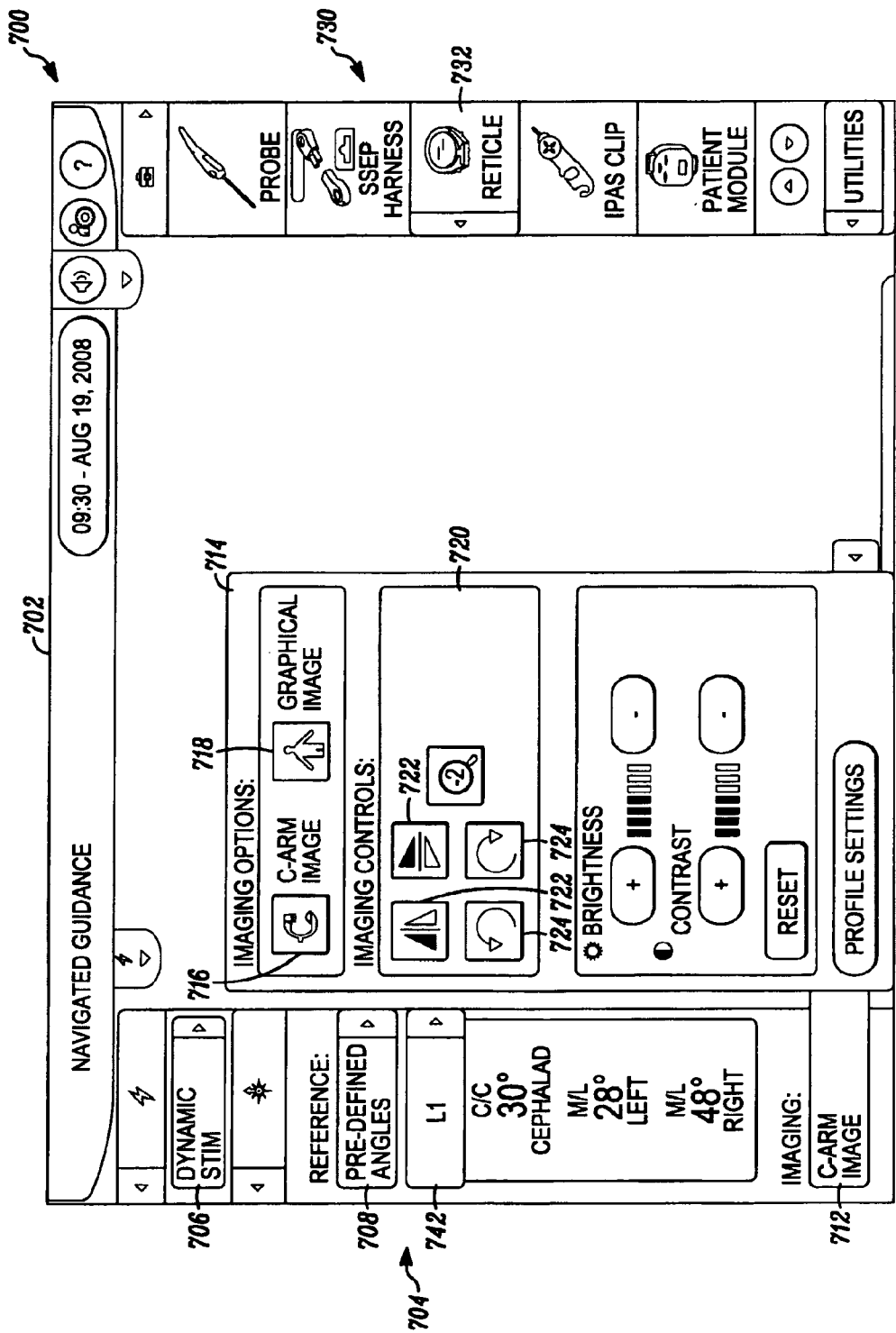
Figure 39:
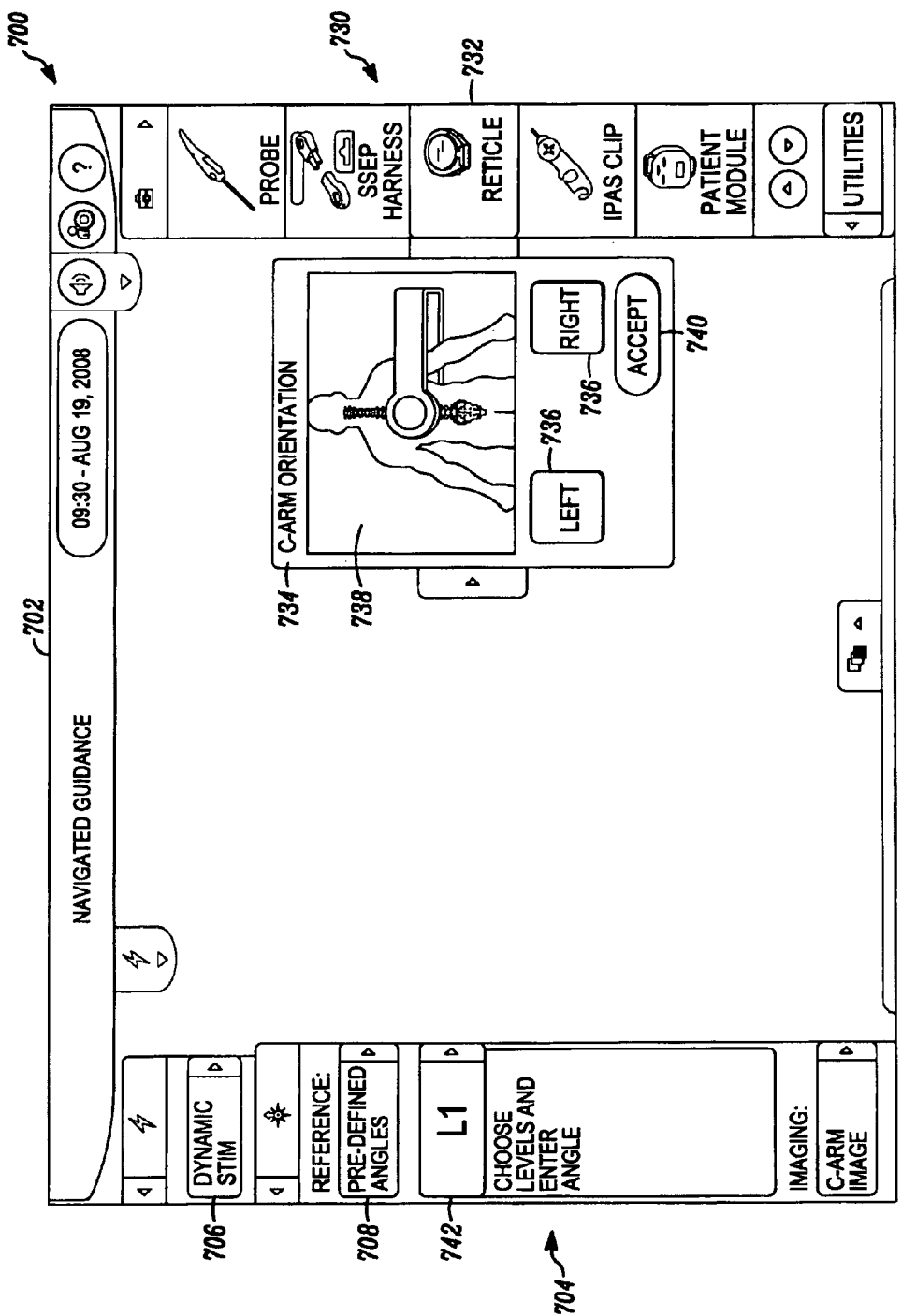

FIG. 38 illustrates the proceeding screen display from selecting imaging button 712. In the imaging field 714, buttons 716 and 718 may be touched to select between the options of integrating live fluoroscopic images from the C-arm or proceeding without integrated images, respectively. In the imaging controls field, the user may set the orientation of the image by pressing the flip and rotate button sets, 722 and 724, respectively. The user may also adjust the brightness and contrasting settings of the image by selecting the appropriate buttons. Display screen also consists of an instrument menu bar 730, capable of allowing the user to make multiple adjustments to multiple integrated feedback instruments. From instrument menu bar 730, the user may set the orientation of the C-arm (i.e. whether the C-arm is positioned on the right or left side of the patient) that is to be utilized during the procedure. The user may select C-arm button 732 labeled, by way of example only, "Reticle". FIG. 39 illustrates the screen display that follows the selection of button 732. In the C-arm orientation field 734 the user may select the desired C-arm orientation by selecting one of the directional buttons 736. C-arm orientation field 734 may also include an anatomical diagram 738 of a patient to assist the user in selecting the C-arm orientation. Although it is not described, it is appreciated that adjustments may be made for other communicatively linked instruments that may be selected from instrument menu bar 730. The accept button 740 locks in the selected configuration and advances the program. The user may then choose to input the predefined M/L and C/C angles into the system by selecting the level button 742 on menu bar 704.

Figure 40:
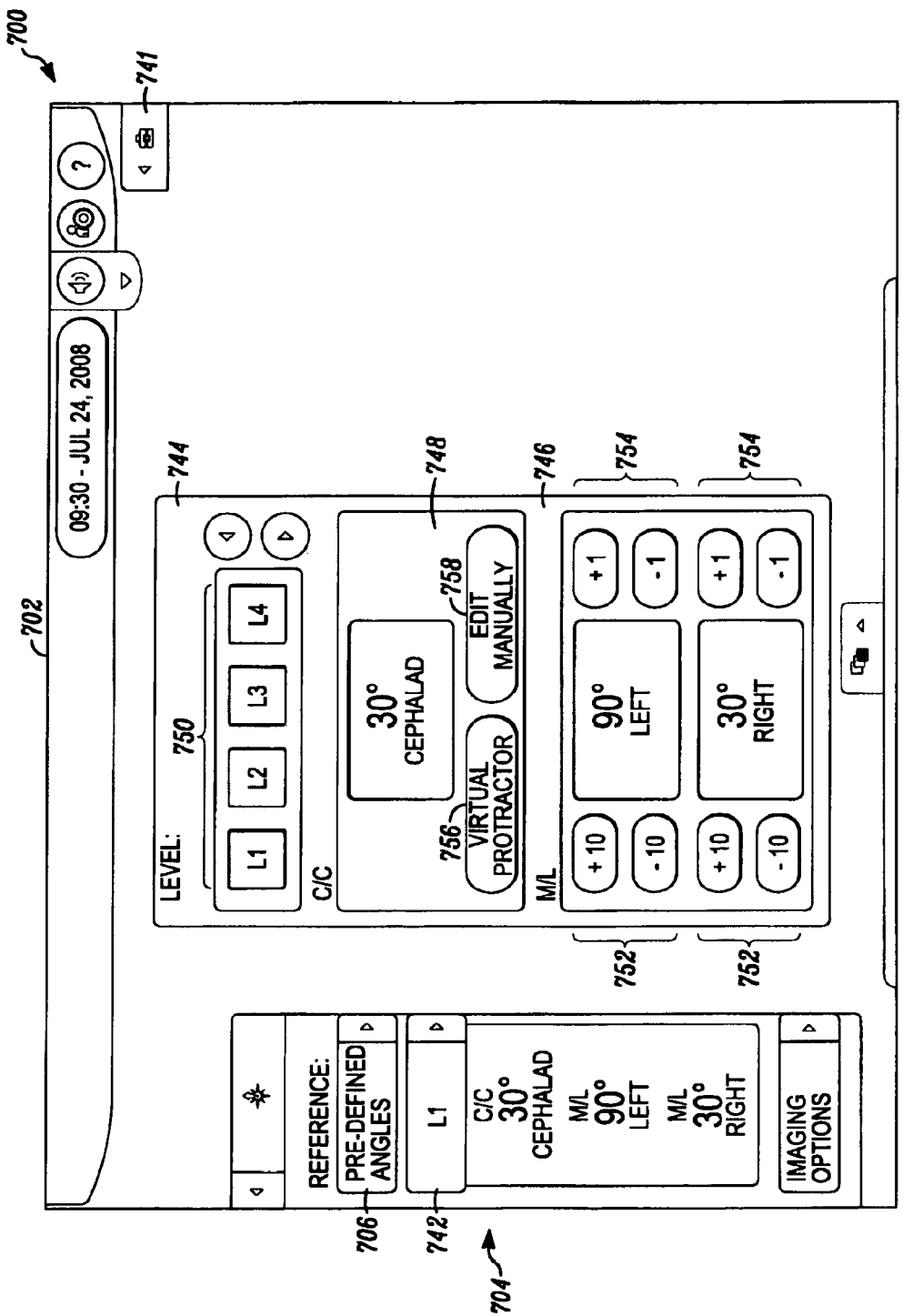

FIG. 40 illustrates, by way of example only, the advancing screen from the selection of level button 742. FIG. 40 also illustrates the user's option of hiding the instrument menu bar 730 by pressing menu hide button 741. From this screen the user may input the M/L angles (A1) and C/C angle (A2) for each pedicle level in the data management field 744. Data management field 744 may be used to view and input angle data in the integrated screen. The data management field includes an M/L window 746, a C/C window 748, and spinal level buttons 750. Spinal level buttons 750 may be used to select and indicate the spinal level which corresponds to the data being input or displayed in the M/L and C/C windows 746 and 748. As previously described, the medial-lateral angles for each pedicle to be instrumented are preferably determined preoperatively. The data may be taken to the OR and entered using the M/L window 746. From the M/L window 746, the user may input the predefined M/L angles by increasing or decreasing the right or left M-L angles in increments of 10° using the angle adjustment buttons 752 labeled (by way of example only) "+10" and "−10". More precise angle adjustments may be made by increasing or decreasing the pre-defined angle in increments of 1° using the angle adjustment buttons 754 labeled (by way of example only) "+1" and "−1". Measurements obtained for the pre-defined cranial-caudal (C-C) angle A2 may also be entered into C/C window 748. By way of example only, pre-defined C/C angle A2 may be entered though either the virtual protractor function (described in more detail below) or angle A2 may be entered manually. The user may select either of these functions by pressing the "Virtual Protractor" button 756 and the "Edit Manually" button 758, respectively.

FIGS. 41-42 illustrate, by way of example only, the subsequent virtual protractor onscreen display of the system when the user selects the "Virtual Protractor" button 756. In this screen, the user is given another opportunity to make additional adjustments to the image of the fluoroscopic image from the imaging controls field 760. It is appreciate that throughout the program, the user may make many adjustments to the system (e.g. adjust the fluoroscopic image, change the reference angles, make adjustments to instrument controls, etc). The chief purpose of this integrated screen display is to determine the angles to be used during a surgical procedure, such as pilot hole formation (i.e. the cranial-caudal and medial-lateral angles discussed elsewhere herein). Spinal level buttons 750 may be selected to input the C/C angle for each level. The C/C angles for each pedicle to be instrumented may be determined using the virtual protractor 762 superimposed on the fluoroscopic image 770. To accomplish this, the C-arm is oriented in the lateral position such that the image 770 shown on the screen is a lateral image. A zero line 764 may be rotated into alignment with the vertical reference line generated in the fluoroscopic image (as previously described) by selecting (e.g. touching) and dragging it into position. The center point 766 of the virtual protractor 762 may then be centered over the appropriate pedicle by touching the image at the desired position. The protractor 762 will then position itself, centered on the position touched. Once positioned over the center of the pedicle, the virtual protractor may be rotated using the control button 768 until it is aligned with the axis of the pedicle. Selecting the save image button 772 will input the angle determined by the rotation of the virtual protractor 762 relative to the zero line 764. With reference to FIG. 42, the user may choose to give the image a file name in save field 774. Virtual protractor screen may also consist of head and foot diagrams 776 to assist the user in understanding the orientation of the patient. The determined C/C angle may be displayed in C/C angle display window 778. Return button 780 brings the user back to the screen display illustrated in FIG. 40.

Figure 43:
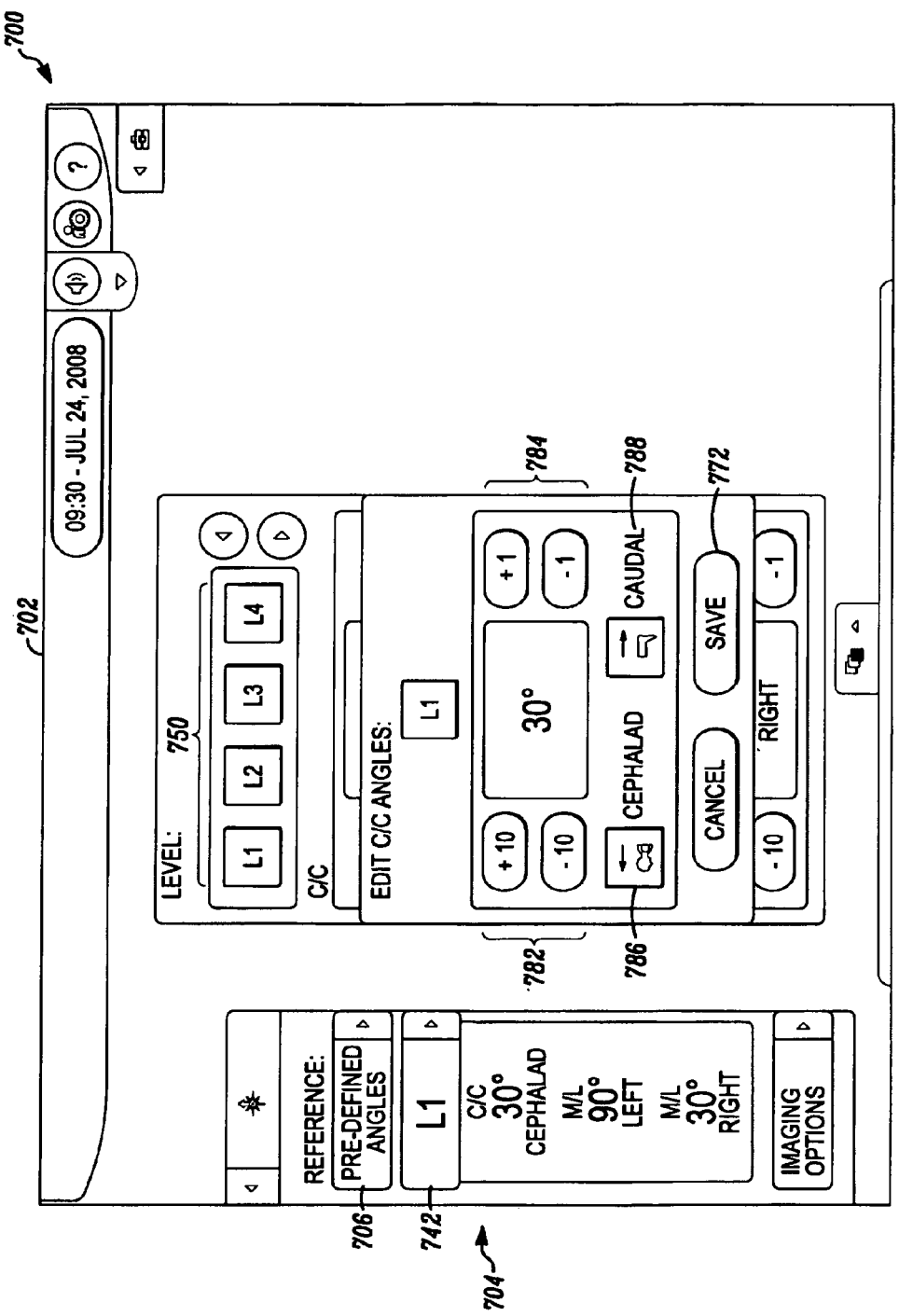

FIG. 43 illustrates, by way of example only, the subsequent onscreen display of the system when the user selects the "Edit Manually" button 758 of FIG. 40. In this example, similar to the process of adjusting the pre-defined M-L angles A1 above, the pre-defined C-C angle A2 may be increased or decreased in increments of 10° and 1° by pressing the angle adjustment buttons, 782 and 784, accordingly. Furthermore, the direction of the pre-defined C-C angle A2 may be entered by pressing the cephalad (towards the head) button 786 and caudal (towards the feet) 788. The user may also manually input the C/C angle at each spinal level by selecting one of the appropriate spinal level buttons 750. By pressing the save button 772, the entered values may be saved by the system such that during the procedure selecting the spinal level from "Reference" menu 517 automatically recalls the inputted values.

Figure 44:
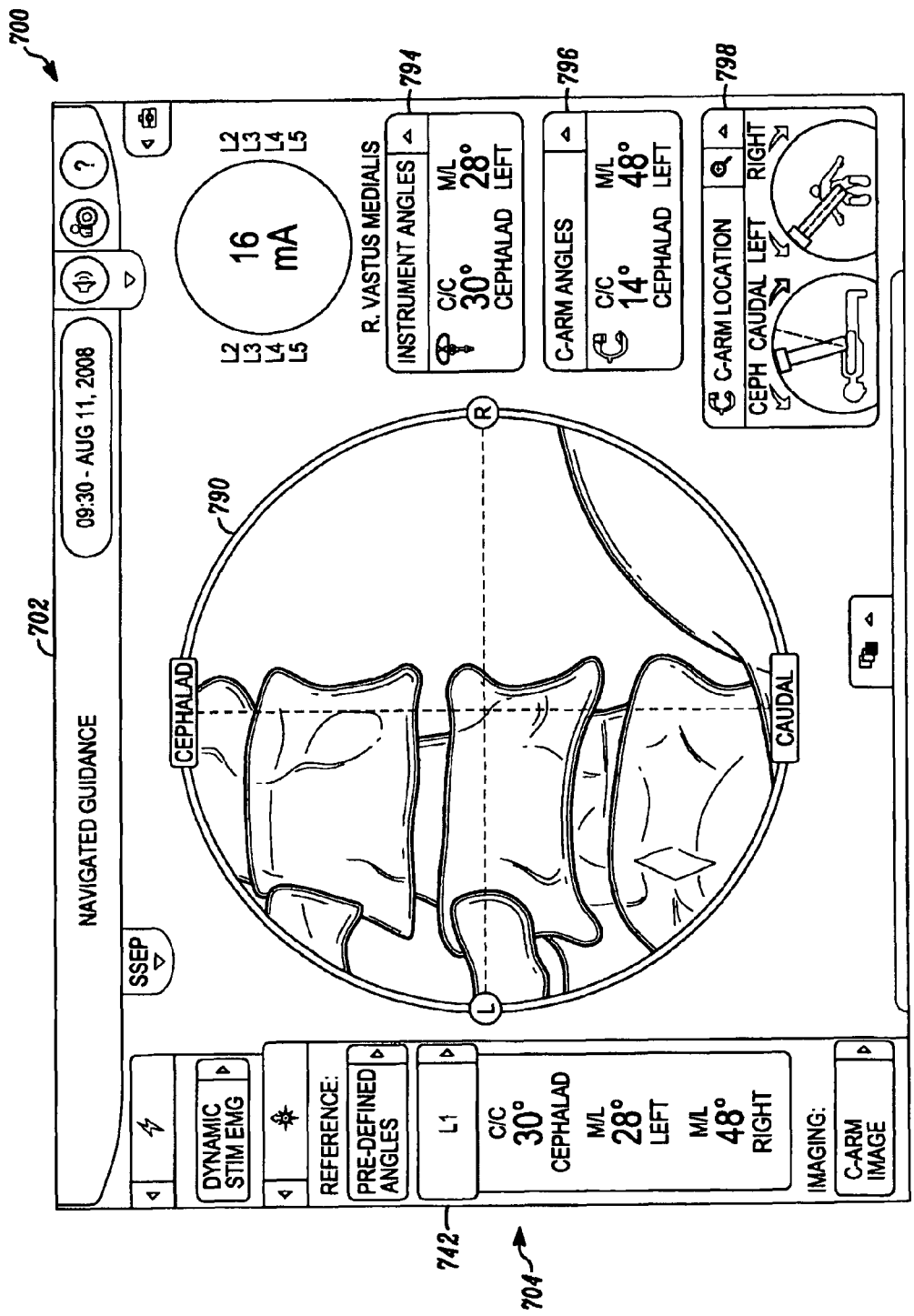
Figure 45:
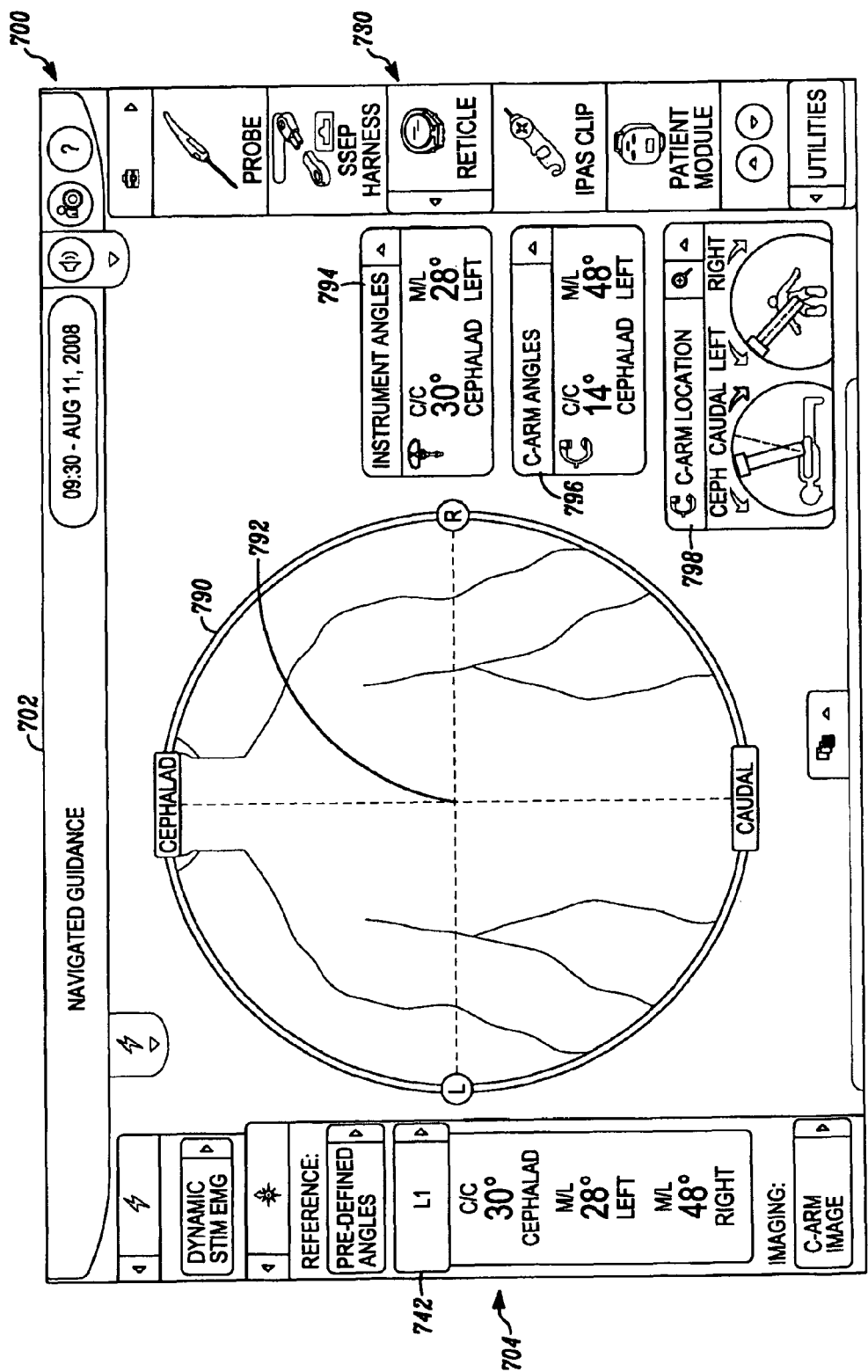
Figure 46:
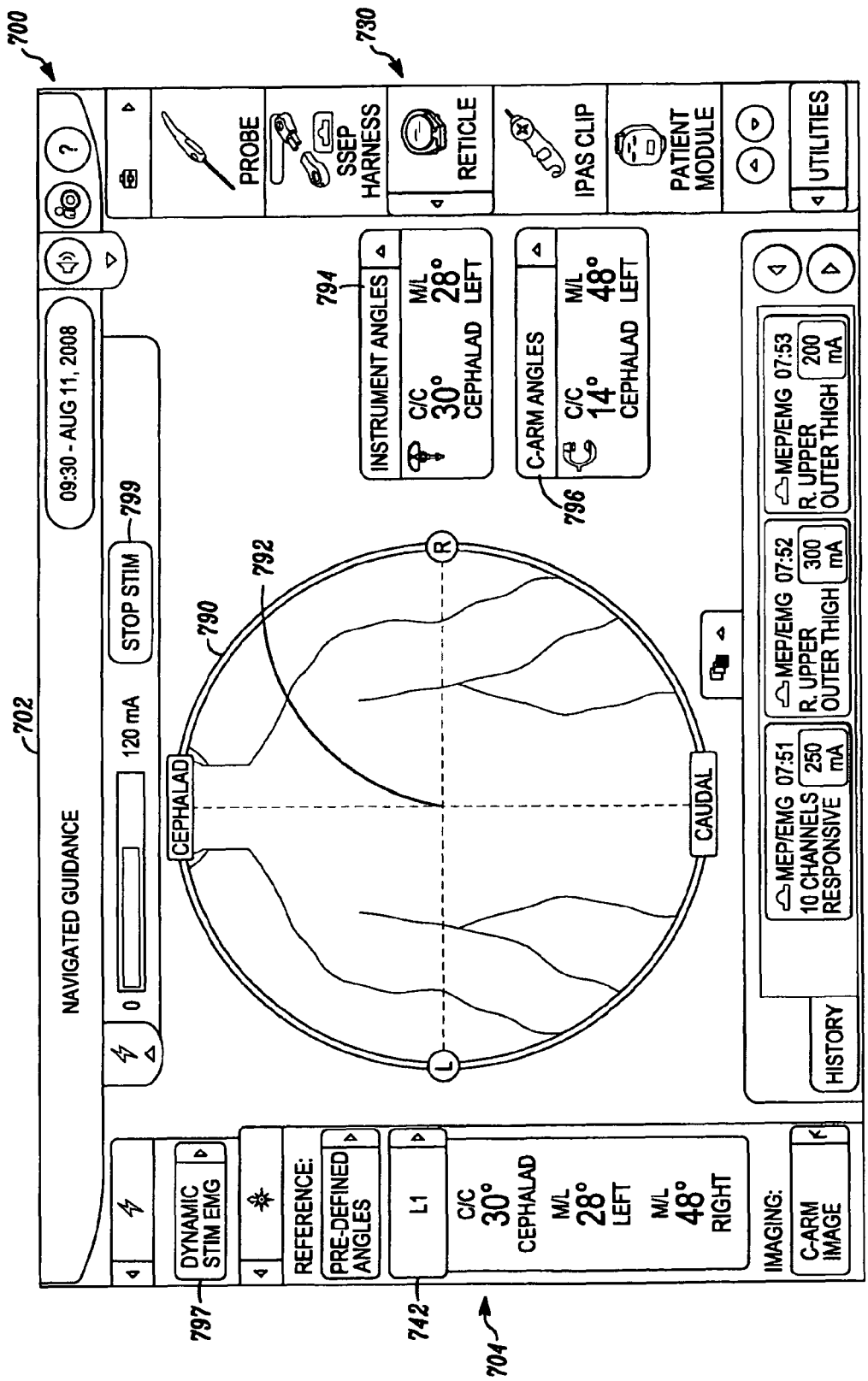
Figure 47:
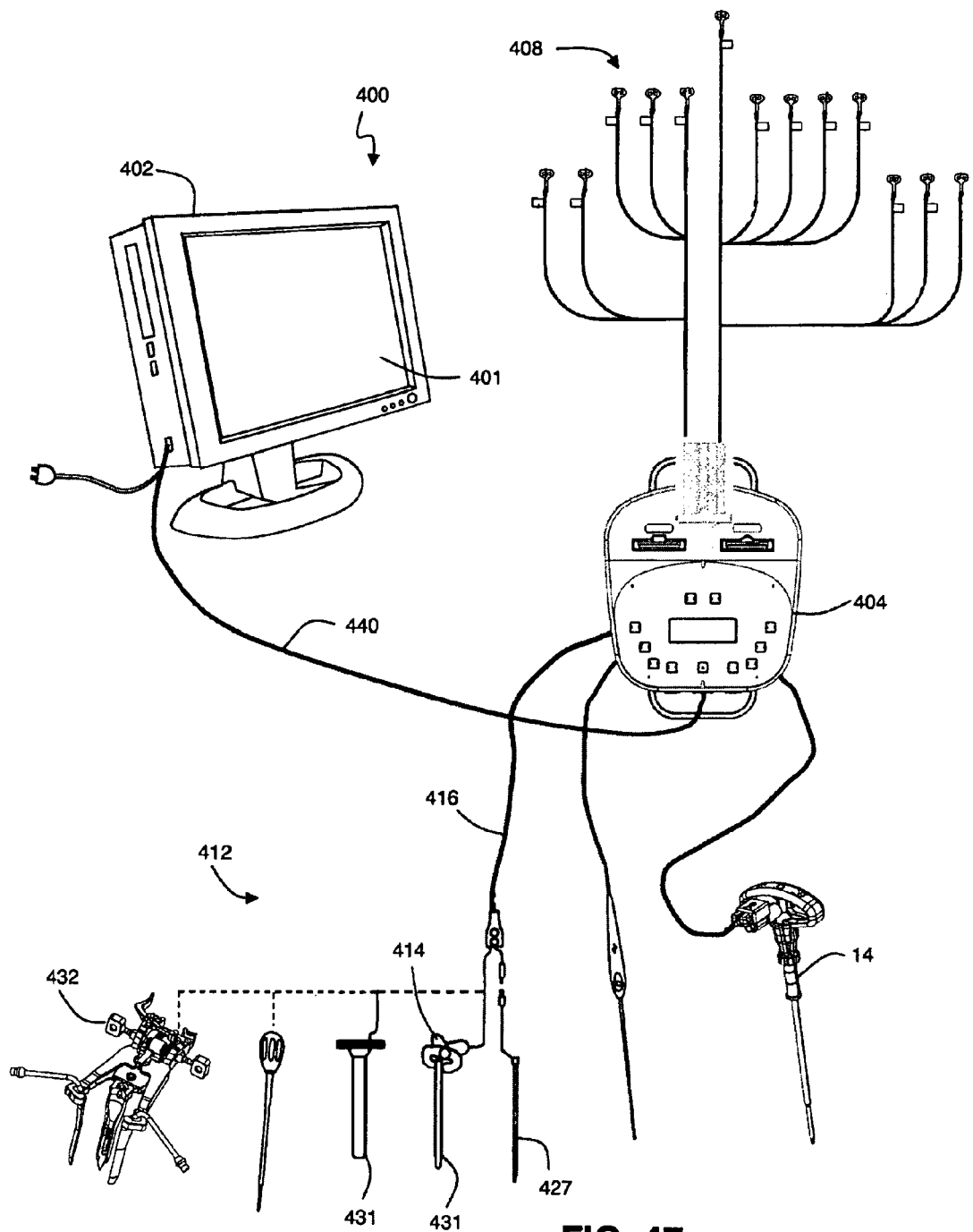
FIG. 47 is a perspective view of an exemplary neuromonitoring system for use in conjunction with the surgical trajectory system of FIG. 1, according to on embodiment of the present invention.

FIGS. 44-46 illustrate, by way of example only, onscreen displays of the system with feedback information from multiple sources. Viewing window 790 may capture a fluoroscopic image from the C-arm, as illustrated in FIG. 44, to assist the operator in determining the fixed angles of the pedicle in pedicle placement procedures. However, the user may choose not to display a fluoroscopic image, and instead utilize a graphic in its replacement, as illustrated in FIGS. 45-46. Viewing window 790 utilizes a cross-hair reference 792 (not visible in FIG. 44) to indicate the center of the image from the C-arm. Center reference 792 may assist the user in procedures which require the surgeon to operate along a desired angular trajectory to the spine. Display 700, in this embodiment, also consists of other feedback information windows to assist the surgeon during operation. Instrument window 794 provides feedback information to the user of the angular orientation of the attach instrument 14. When the angular orientation of the instrument is in accordance with the predefined angular orientation, the system may alert the user of the match. By way of example only, instrument window 794 may be saturated with a color (e.g. green) to indicate the proper alignment of the instrument. Instrument window 794 may also provide alphanumeric feedback. When the angular orientation of the instrument is properly aligned with the predefined angles, the M/L angles and the C/C angles with match accordingly (A1(i)=A1). Menu bar 704 may also provide the predefined reference angles for each level to compare with the feedback information of the various instruments. C-arm window 796 may also communicate feedback information to the user. In similar fashion to instrument window 794, feedback information from the angular orientation of the C-arm may be utilized. FIGS. 44 and 45 illustrate an additional C-arm window 798 depicted the orientation of the C-arm as in relation to the patient.

FIG. 46 illustrates, by way of example only, the onscreen display 700 of an display screen system when running neurophysiologic test. Neurophysiologic button 797 allows the user to run neurophysiologic test. By way of example only, the user may select to run a dynamic stimulated EMG test while continuing to run the navigated guidance features of the current system with feedback information from multiple sources. Stop button 799 allows the user to stop stimulation when running a test. FIG. 46 also illustrates the integrated system's ability to recall saved recordings from the history menu 795

The surgical trajectory system 10 described above may be used in combination with any number of neurophysiologic monitoring systems. These may include, but are not necessarily limited to, neurophysiologic monitoring systems capable of conducting pedicle integrity assessments before, during, and after pilot hole formation, as well as to detect the proximity of nerves while advancing and withdrawing the surgical instrument 14 from the pedicle target site. By way of example, the surgical trajectory monitoring system 10 may be used in conjunction with the neuromonitoring system 400, illustrated by way of example only in FIG. 48, which is shown and described in the commonly owned and co-pending U.S. patent application Ser. No. 12/080,630, entitled "Neurophysiology Monitoring System," and filed on April 3, the entire contents of which is hereby incorporated by reference as if set forth fully herein. Neuromonitoring system 400 may perform, by way of example, the Twitch Test, Free-run EMG, Basic Screw Test, Difference Screw Test, Dynamic Screw Test, MaXcess® Detection, and Nerve Retractor, all of which will be described briefly below. Functionality of neuromonitoring system 400 has been described in detail elsewhere and will be described only briefly herein. The Twitch Test mode is designed to assess the neuromuscular pathway via the so-called "train-of-four" test to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which is hereby incorporated by reference as if set forth fully herein. The Basic Screw Test, Difference Screw Test, and Dynamic Screw Test modes are designed to assess the integrity of bone (e.g. pedicle) during all aspects of pilot hole formation (e.g., via an awl), pilot hole preparation (e.g. via a tap), and screw introduction (during and after). These modes are described in greater detail in PCT Patent App. No. PCT/US2002/035047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004 the entire contents of which are both hereby incorporated by reference as if set forth fully herein. The MaXcess® Detection mode is designed to detect the presence of nerves during the use of the various surgical access instruments of the neuromonitoring system 400, including the k-wire 427, dilator 430, cannula 431, retractor assembly 432. This mode is described in greater detail within PCT Patent App. No. PCT/US2002/022247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/US2002/030617, entitled "System and Methods for Performing Surgical Procedures and Assessments," filed on Sep. 25, 2002, the entire contents of which are hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within PCT Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein.

With reference to FIG. 48, the neurophysiology system 400 includes a display 401, a control unit 402, a patient module 404, an EMG harness 406, including eight pairs of EMG electrodes 408 and a return electrode 410 coupled to the patient module 404, and a host of surgical accessories 412, including an electric coupling device 414 capable of being coupled to the patient module 404 via one or more accessory cables 416. To perform the neurophysiologic monitoring, the surgical instrument 14 is configured to transmit a stimulation signal from the neurophysiology system 400 to the target body tissue (e.g. the pedicle). As previously mentioned, the probe members 30 may be formed of material capable of conducting the electric signal. To prevent shunting of the stimulation signal, the probe member 30 may be insulated.

The neurophysiology system 400 performs nerve monitoring during surgery by measuring the degree of communication between a stimulation signal and nerves or nerve roots situated near the stimulation site. To do this, the surgical instrument is connected to the neurophysiology monitoring system 400 and stimulation signals are activated and emitted from the distal end. EMG electrodes 408 positioned over the appropriate muscles measure EMG responses corresponding to the stimulation signals. The relationship between the EMG responses and the stimulation signals are then analyzed by the system 400 and the results are conveyed to the practitioner on the display 401. More specifically, the system 400 determines a threshold current level at which an evoked muscle response is generated (i.e. the lowest stimulation current that elicits a predetermined muscle response). Generally the closer the electrode is to a nerve the lower the stimulation threshold will be. Thus, as the probe member or surgical access members move closer to a nerve, the stimulation threshold will decrease, which may be communicated to the practitioner to alert him or her to the presence of a nerve. The pedicle integrity test, meanwhile, works on the underlying theory that given the insulating character of bone, a higher stimulation current is required to evoke an EMG response when the stimulation signal is applied to an intact pedicle, as opposed to a breached pedicle. Thus, if EMG responses are evoked by stimulation currents lower than a predetermined safe level, the surgeon may be alerted to a possible breach. The surgical instrument 14 may be connected to the neurophysiology system 400 by through sensor clip 12. By way of example and with reference to FIGS. 2-3, an additional cable 47 may couple the clip 12 to the neurophysiology system 400. Attached to the cable 47, inside the endhook 48, is an exposed wire 49 that contact the exposed proximal portion 40 of instrument 14.

During pilot hole formation, while the trajectory of the surgical instrument is being monitored to prevent the instrument from breaching the pedicle walls, pedicle integrity assessments may be performed to alert the practitioner in the event a breach does occur. Stimulation signals are emitted from the electrode, which should be at least partially positioned within the pedicle bone during hole formation. The stimulation threshold is determined and displayed to the surgeon via the neurophysiology monitoring system 400. Due to the insulating characteristics of bone, in the absence of a breach in the pedicle wall, the stimulation threshold current level should remain higher than a predetermined safe level. In the event the threshold level falls below the safe level, the surgeon is alerted to the potential breach. When the pilot hole is fully formed, a final integrity test should be completed.

In one embodiment, the neurophysiology system 400 control unit and the surgical trajectory system 10 control unit 16 may be integrated into a single unit. Neurophysiology monitoring and trajectory monitoring may be carried out concurrently and the control unit may display results for each of the trajectory monitoring function and any of the variety of neurophysiology monitoring functions. Alternatively, the control unit 16 and control unit 402 may comprise separate systems and the sensor clip 12 may be communicatively linked directly to control unit 402 of the neurophysiology monitoring system and the control unit 16.

While the invention is susceptible to various modifications and alternative forms, (such as the drill bit, needle points, and T-handle mentioned above) specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the scope and spirit of the invention as defined herein. By way of example, the method for determining the cranial-caudal A2 has been described herein as taking place intraoperatively using lateral fluoroscopy imaging. However, the cranial-caudal angle may also be determined preoperatively employing various imaging and/or computer processing applications. For example, a 3-D model of a patient's vertebra (or other applicable body part) may be obtained using a combination of medical imaging and computer processing. From the 3-D model the angle A2 may be calculated after which the determined value may be utilized by the surgical trajectory system and methods described above. It is further contemplated that computer processing of medical images may be used to extrapolate the pedicle axis angles A1 and A2 without the need for human intervention. Finally, it will be appreciated that the intraoperative monitoring discussed herein has generally focused on the use of a C-arm fluoroscopic imager, however, orienting the C-arm with a tilt sensor and providing a trajectory oriented reticle/plumb line using the methods and systems described herein may apply to any form of intraoperative monitoring.

What is claimed is:

1. A method for cannulating a vertebral pedicle in a body comprising the steps of:
   a. coupling a first orientation sensor to an intraoperative imaging device, said first orientation sensor operable to determine a first angular relationship in a first plane between said first orientation sensor and a reference direction and operable to determine a second angular relationship in a second plane between said first orientation sensor and said reference direction, wherein said second plane is orthogonal to said first plane and said first orientation sensor is coupled to said intraoperative imaging device in a known orientation, said first orientation sensor being communicatively linked to a control unit, said control unit comprising a computer;

b. capturing an image of said vertebral pedicle with said intraoperative imaging device, said intraoperative device being positioned in a first position during said image capture;

c. using said control unit to measure a value representing an angular orientation of said vertebral pedicle;

d. coupling a second orientation sensor to a surgical instrument, said second orientation sensor operable to determine a third angular relationship in said first plane between said second orientation sensor and a reference direction and operable to determine a fourth angular relationship in said second plane between said second orientation sensor, wherein said second orientation sensor is coupled to said surgical instrument in a known orientation, said second orientation sensor being communicatively linked to a control unit;

e. adjusting the orientation of said surgical instrument until said second orientation sensor indicates that the surgical instrument is aligned with said measured value representing the angular orientation of said vertebral pedicle; and f. advancing a distal end of said surgical instrument through said body tissue and into said vertebral pedicle.

2. The method of claim 1, comprising the additional step of rotating said imaging device into a second position prior to advancing said surgical instrument into said vertebral pedicle.

3. The method of claim 2, wherein said first position is a lateral position.

4. The method of claim 3, wherein said second position is an oblique position.

5. The method of claim 2, comprising the additional step of directing a laser beam from said intraoperative imaging device to a preferred entry site for said surgical instrument on said body.

6. The method of claim 5, wherein said laser beam creates a cross pattern over said preferred entry site.

7. The method of claim 6, wherein said laser beam is directed from a reticle coupled to the intraoperative imaging device.

8. The method of claim 1, wherein said second orientation sensor indicates alignment with said measured value via at least one light emitting diode (LED) light coupled to said orientation sensor.

9. The method of claim 8, wherein said second orientation sensor includes multiple LED lights that light according to the direction the instrument must travel to align with said value representing the angular orientation of said vertebral pedicle.

10. The method of claim 8, wherein said second orientation sensor couples to a handle of said surgical instrument and said LED light is adjacent to said handle.

11. A system for use during spinal surgery, comprising:
a control unit comprising a computer, said control unit configured to direct the advancement of a pedicle access instrument;

said control unit being communicatively linked to a first orientation sensor operable to determine a first angular relationship in a first plane between said first orientation sensor and a reference direction and operable to determine a second angular relationship in a second plane between said first orientation sensor and said reference direction, wherein said second plane is orthogonal to said first plane and said first orientation sensor is coupled to an imaging device in a known orientation, said control unit operable to define a first trajectory setting based on the determined first angular relationship and second angular relationship when said imaging device is oriented in a desired position;

said control unit further being communicatively linked to a second orientation sensor operable to determine a third angular relationship in said first plane between said second orientation sensor and a reference direction and operable to determine a fourth angular relationship in said second plane between said second orientation sensor and said reference direction, wherein said second orientation sensor is coupled to said pedicle access instrument; and a display communicatively linked to said control unit, said display configured to display alpha-numeric, graphic, and color indicia related to said first trajectory setting, said display being further configured to display alpha-numeric, graphic, and color indicia related to said second orientation sensor, said alpha-numeric, graphic, and color indicia, indicating a trajectory of said pedicle access instrument is aligned with said first trajectory.

12. The system of claim 11, wherein said display is further configured to show at least one of live video and a still image.

13. The system of claim 12, wherein at least one of said live video and said still image is a fluoroscopic image.

14. The system of claim 11, wherein at least one of said first orientation sensor and said second orientation sensor comprises at least one accelerometer and said reference direction is gravity.

15. The system of claim 11, wherein said second orientation sensor is further configured to transmit a stimulation signal to said pedicle access instrument.

16. The system of claim 15, wherein said stimulation signal is part of said neurophysiologic a pedicle integrity test.

17. The system of claim 11, wherein said color indicia includes at least one of a green color indicative of an optimal variance between said trajectory of said surgical instrument and said first trajectory, a red color indicative of an unacceptable variance between said trajectory of said surgical instrument and said first trajectory, and a yellow color indicative of an acceptable yet not optimal variance between said trajectory of said surgical instrument and said first trajectory.

* * * * *